US012036142B1

(12) United States Patent
Fried et al.

(10) Patent No.: US 12,036,142 B1
(45) Date of Patent: Jul. 16, 2024

(54) BODY BRACE AND METHOD OF USE

(71) Applicants: Scott Fried, Gwynedd Valley, PA (US);
Doran Edwards, Franklin, TN (US)

(72) Inventors: Scott Fried, Gwynedd Valley, PA (US);
Doran Edwards, Franklin, TN (US)

(73) Assignee: Scott Fried, Gwynedd, PA (US)

( * ) Notice: Subject to any disclaimer, the term of this patent is extended or adjusted under 35 U.S.C. 154(b) by 1027 days.

(21) Appl. No.: 16/938,056

(22) Filed: Jul. 24, 2020

Related U.S. Application Data

(63) Continuation-in-part of application No. 16/101,771, filed on Aug. 13, 2018, now abandoned.

(60) Provisional application No. 62/545,736, filed on Aug. 15, 2017.

(51) Int. Cl.
*A61F 5/00* (2006.01)
*A61F 5/02* (2006.01)

(52) U.S. Cl.
CPC .............. *A61F 5/022* (2013.01); *A61F 5/024* (2013.01); *A61F 5/026* (2013.01); *A61F 5/028* (2013.01)

(58) Field of Classification Search
USPC ...................................... 602/7, 19
See application file for complete search history.

(56) References Cited

U.S. PATENT DOCUMENTS

| 4,708,130 | A | * | 11/1987 | Grudem | A61F 5/028 602/19 |
| 5,334,134 | A | * | 8/1994 | Saunders | A41D 13/0525 128/100.1 |
| 5,843,008 | A | * | 12/1998 | Gerhard | A61F 5/03 602/5 |
| 9,107,738 | B2 | * | 8/2015 | Kilbey | A61F 5/028 |
| 2010/0204630 | A1 | * | 8/2010 | Sandifer | A61F 5/026 602/19 |

FOREIGN PATENT DOCUMENTS

EP  0507513 A1 * 7/1992

OTHER PUBLICATIONS

Poulson, Marissa, Methods of Molding Kydex, eHow (Year: 2014).*

* cited by examiner

*Primary Examiner* — Kim M Lewis
(74) *Attorney, Agent, or Firm* — GARCIA-ZAMOR INTELLECTUAL PROPERTY LAW, LLC; Ruy Garcia-Zamor

(57) ABSTRACT

A body brace and/or body brace kit to facilitate the recovery of a person from an injury, to provide additional support, or to prevent further injury from being done to one or more body parts. The body brace may provide customizable and changeable embodiments to better assist a person in healing and may provide additional support or massage action for one or more preferred body parts.

5 Claims, 46 Drawing Sheets

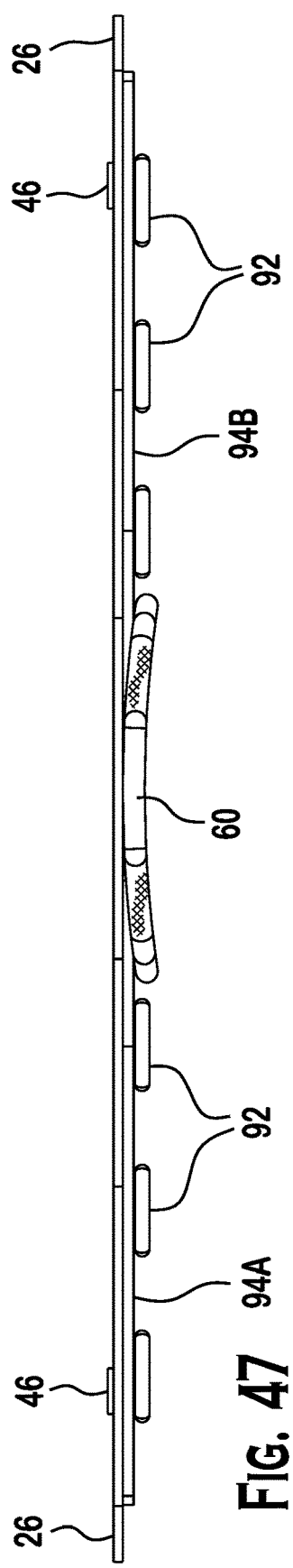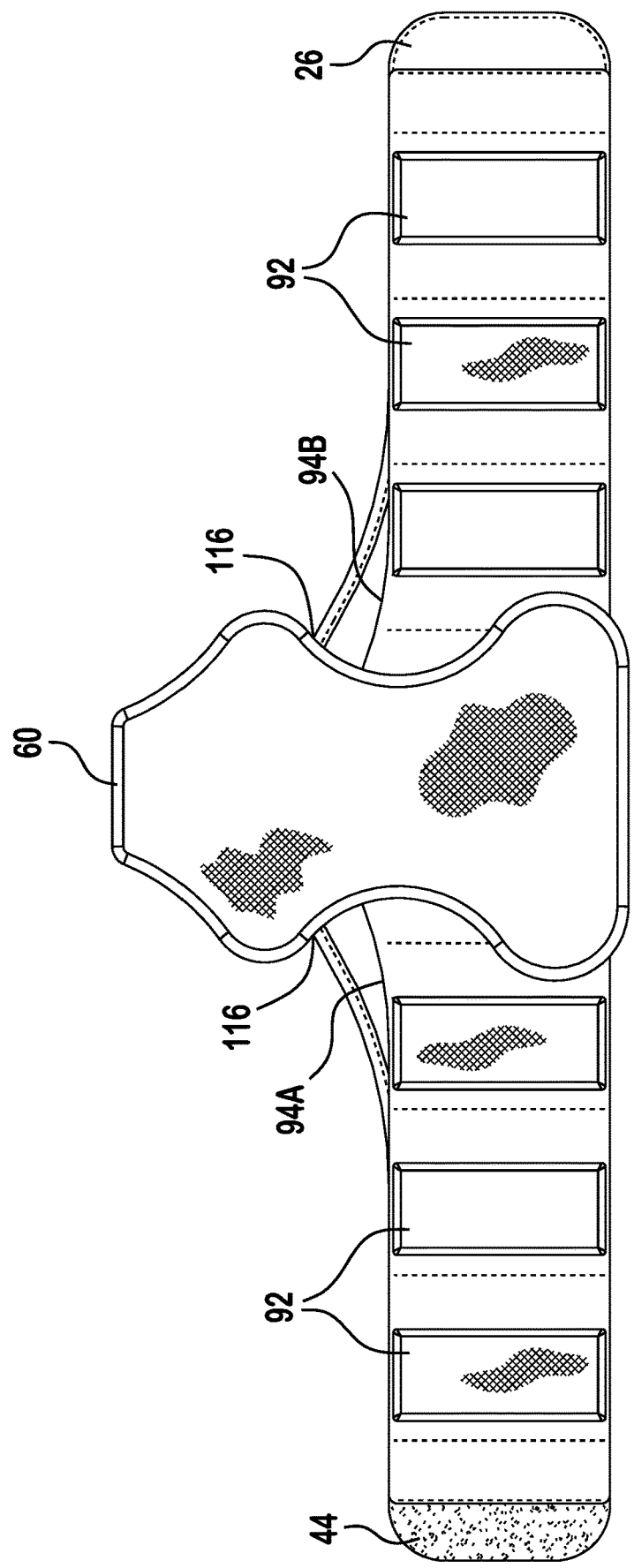

BODY BRACE AND METHOD OF USE

CROSS REFERENCE TO RELATED APPLICATIONS

This application claims priority to and is a continuation-in-part of U.S. patent application Ser. No. 16/101,771, filed Aug. 13, 2018, which claims priority to and benefit of U.S. provisional patent application 62/545,736, filed Aug. 15, 2017, each of which is hereby incorporated by reference in its entirety as if fully set forth herein.

BACKGROUND

The present invention relates generally to devices used for the support and immobilization of the body, and, more specifically, to a brace for immobilizing portions of the torso to provide increased support and stability to the core of a person's body.

Braces are commonly used to immobilize a person's body by preventing movement. In many cases, this support may serve to immobilize or limit movement of a broken bone, damaged joint, or injured muscle. A back brace traditionally provides immobilization to the body, but can cause atrophy, slower healing, and other complications due to its excessive rigidity.

It may be advantageous to provide a body brace which is customizable to a user's specific shape and movement; may conform to a desired orientation or shape; may provide additional support; may allow for therapeutic movement during use; may provide gentle massaging action and heat application; may provide adjustable support; may allow for quick and efficient use; can be easily manufactured; and/or is preferably efficient to manufacture.

SUMMARY

In one aspect, one preferred embodiment of the present invention is directed to a body brace that may be customizable to better provide support to at least a portion of a torso of a person, such as a person's back, spine, ribs, abdomen, or other portions of the body. The body brace may include a first brace body configured to wrap around a portion of a torso of a person and a support pocket therein. This support pocket may be configured to allow a support member to be inserted therein, the support member being configured to provide a contoured configuration to the first brace body and to provide resistance against bending the torso in a manner to drive the first brace body out of the contoured configuration.

In another aspect, one embodiment of the present invention is directed to a body brace which may comprise a support member, the shape of which may be adjusted via heating and cooling to allow the support member to provide customized, contoured support specific to the user.

In another aspect, one embodiment of the present invention is directed to a body brace which includes both a first brace body configured to wrap around a portion of a torso of a person and a second brace body configured to wrap around a second portion of the torso of the person. The first brace body may include a support pocket configured to hold a support member therein, and the second brace body may include a guide pocket therein configured to hold the support member in place while allowing it to pass therethrough.

In another aspect, one embodiment of the present invention is directed to a body brace which includes both a first brace body and a second brace body, where the first brace body and second brace body may be detachably connected. In some embodiments, at least one strap may be used to detachably connect the first brace body and the second brace body via hook and loop material. In some other embodiments, one linkage block may be used to connect the first brace body and the second brace body via hook-and-loop material or other connective means.

In another aspect, one embodiment of the present invention is directed to a body brace which includes both a first brace body and a second brace body and a support member, wherein the first brace body may include a support pocket, and the second brace body may include a guide pocket. The support member may be positioned in both the support pocket and the guide pocket. In some embodiments, the support member may be removeable from and insertable into the support pocket and/or the guide pocket.

In another aspect, one embodiment of the present invention is directed to a body brace which includes both a first brace body, a second brace body, and at least one support member, wherein the first brace body does not overlap the second brace body. The first brace body may include at least one support pocket and the second brace body may include at least one guide pocket. The at least one support member may be positioned in one of both the at least one support pocket and the at least one guide pocket. The first and second brace bodies may be connected only by at least one of the support member. In other embodiments, the first and second brace bodies may be connected only by at least one support member and by at least one linkage block.

In another aspect, one embodiment of the present invention is directed to a body brace which includes both a first brace body, a second brace body, and at least two support members, wherein the first brace body does not overlap the second brace body. The first brace body may include at least two support pockets and the second brace body may include at least two guide pockets. The first of the at least two support members and the second of at least two support members each being secured in one of the at least two support pockets and one of the at least two guide pockets respectively such that the first support member and the second support member provide the desired configuration to both the first brace body and the second brace body while not being parallel to each other nor overlapping each other.

In another aspect, one embodiment of the present invention is directed to a body brace which includes both a first brace body, a second brace body, and at least two support members, wherein the first brace body does not overlap the second brace body. The first brace body may include at least two support pockets and the second brace body may include at least two guide pockets. The support members may be positioned in mirror-image angles from each other along a vertical axis of the body brace in a V-shape. These may be include along with other support members not held in a V-shape, to provide varying configurations for support.

In another aspect, one embodiment of the present invention is directed to a body brace that may be customizable to better provide support to at least a portion of a torso of a person, such as a person's back, spine, ribs, abdomen, or other portions of the body. The body brace may include a first brace body configured to wrap around a portion of a torso of a person and a shell positioned thereon which may extend above and below the first brace body.

In another aspect, one embodiment of the present invention is directed to a body brace that may be customizable to better provide support to at least a portion of a torso of a person, such as a person's back, spine, ribs, abdomen, or other portions of the body. The body brace may include a first brace body configured to wrap around a portion of a torso of a person and a shell positioned thereon. Shoulder straps may be attachable to the shell to facilitate wearing and reduce fatigue during use.

In another aspect, one embodiment of the present invention is directed to a body brace that may be customizable to better provide support to at least a portion of a torso of a person, such as a person's back, spine, ribs, abdomen, or other portions of the body. The body brace may include a first brace body configured to wrap around a portion of a torso of a person and a shell and side supports positioned thereon. Shoulder straps may be attachable to the shell to facilitate wearing and reduce fatigue during use.

In another aspect, one embodiment of the present invention is directed to a body brace that may be customizable to better provide support to at least a portion of a torso of a person, such as a person's back, spine, ribs, abdomen, or other portions of the body. The body brace may include a first brace body configured to wrap around a portion of a torso of a person and a shell and side supports positioned thereon.

In another aspect, one embodiment of the present invention is directed to a body brace that may be customizable to better provide support to at least a portion of a torso of a person, such as a person's back, spine, ribs, abdomen, or other portions of the body. The body brace may include shoulder straps may be attachable to the shell to facilitate wearing and reduce fatigue during use.

In another aspect one embodiment of the present invention is directed to a body brace that is customizable for use in supporting at least a portion of a torso of a person. The body brace includes a first brace body configured to wrap around a portion of a torso of the person to provide support to the torso. A shell is positionable on the first brace body and is configured to contact a greater portion of the person's back than the first brace body. The shell being configured to maintain the person's torso in a contoured configuration and to provide resistance against bending the torso in a manner that does not conform with the contoured configuration.

In another aspect, one embodiment of the present invention is directed to a body brace that is customizable for use in supporting at least a portion of a torso of a person. The body brace includes a first brace body configured to wrap around a portion of a torso of the person to provide support to the torso. A shell is positionable on the first brace body and is configured to contact a greater portion (i.e., a greater surface area) of the person's back than the first brace body. The shell is configured to maintain the person's torso in a contoured configuration and to provide resistance against bending the torso in a manner that does not conform with the contoured configuration. The shell having an arcuate upper edge and an arcuate lower edge. The arcuate upper edge being shorter than the arcuate lower edge. A plurality of shoulder straps are positioned on the shell such that the body brace encircles the person's torso while also being supported on the person's shoulders to further secure the shell in a proper position on the person's back.

In another aspect, one embodiment of the present invention is directed to a body brace that is customizable for use in supporting at least a portion of a torso of a person. The body brace includes a first brace body configured to wrap around a portion of a torso of the person to provide support to the torso. A shell is positionable on the first brace body and is configured to contact a greater portion (i.e., a greater surface area) of the person's back than the first brace body. The shell is configured to maintain the person's torso in a contoured configuration and to provide resistance against bending the torso in a manner that does not conform with the contoured configuration. A plurality of shoulder straps are positioned on the shell such that the body brace encircles the person's torso while also being supported on the person's shoulders to further secure the shell in a proper position on the person's back.

In another aspect, one embodiment of the present invention is directed to a body brace that is customizable for use in supporting at least a portion of a torso of a person. The body brace includes a shell configured to maintain the person's torso in a contoured configuration and to provide resistance against bending the torso in a manner that does not conform with the contoured configuration. A plurality of shoulder straps are positioned on the shell such that the body brace encircles the person's torso while also being supported on the person's shoulders to further secure the shell in a proper position on the person's back.

In another aspect, one embodiment of the present invention is directed to a body brace that is customizable for use in supporting at least a portion of a torso of a person. The body brace includes a shell configured to maintain the person's torso in a contoured configuration and to provide resistance against bending the torso in a manner that does not conform with the contoured configuration. A plurality of shoulder straps are positioned on the shell such that the body brace encircles the person's torso while also being supported on the person's shoulders to further secure the shell in a proper position on the person's back. Wherein the shell includes a flexible vertical rib positioned generally along a longitudinal axis thereof such that left and right sides of the shell can fold with a hinge axis formed by the vertical rib and/or wherein the shell includes upper and lower portions which can twist relative to each other about the longitudinal axis.

In another aspect, one embodiment of the present invention is directed to a body brace that is customizable for use in supporting at least a portion of a torso of a person. The body brace includes a shell configured to maintain the person's torso in a contoured configuration and to provide resistance against bending the torso in a manner that does not conform with the contoured configuration. Wherein the shell includes a flexible vertical rib positioned generally along a longitudinal axis thereof such that left and right sides of the shell can fold with a hinge axis formed by the vertical rib and/or wherein the shell includes upper and lower portions which can twist relative to each other about the longitudinal axis.

In another aspect, the present invention is directed to a body brace kit that is customizable for use in supporting at least a portion of a torso of a person. The kit may include at least three components. One of the at least three components is a first brace body configured to wrap around a portion of a torso of the person to provide support to the torso and generally define a central in-use axis. The at least three components further comprise two components from the following list of detachable members: (1) a first torso support wing and a second torso support wing, each including: a plurality of encased struts aligned generally side-to-side and each having a longitudinal side facing the longitudinal side of an adjacent one of the plurality of encased struts. The first torso support wing and the second torso support wing are configured to encircle the torso of a person to provide resistance against lateral bending of the person; (2) a lower back support pad is configured to be located along a back of the person when used with the first brace body wrapped around the person; (3) a side support member is configured to be located along a side of the torso when used with the first brace body wrapped around the person. The side support member may be greater in length than a portion of the first brace body so that when in use the side support member protrudes past at least one of a lower edge and an upper edge of the first brace body; (4) a non-protruding side support member configured to be located along a side of the torso when used with the first brace body wrapped around the person. The non-protruding side support member not being greater in length than a portion of the first brace body so that when in use the non-protruding side support member does not protrude past either one of a lower edge and an upper edge of the first brace body; (5) a shell positionable on the first brace body and configured to contact a greater portion of a back of the person than the first brace body. The shell being configured to maintain the back in a contoured configuration and to provide resistance against bending in a manner that does not conform with the contoured configuration; (6) a back support member configured to be detachably positioned on a side of the shell which faces the person's back; and (7) a chest support member positionable on the first brace body and configured to contact a greater portion of the chest of the person than the first brace body. The chest support being configured to maintain the chest in a second contoured configuration and to provide resistance against bending in a manner that does not conform with the second contoured configuration. Wherein all of the at least three components, except for the first body brace, are: (1) detachably attachable to the first brace body; and (2) can be adjusted via heating and cooling thereof to allow a shape to be changed to provide the contoured configuration customized for the person.

In another aspect, the present invention is directed to a body brace kit that is customizable for use in supporting at least a portion of a torso of a person including at least three components. One of the at least three components is a first brace body configured to wrap around a portion of a torso of the person to provide support to the torso and generally define a central in-use axis. Two of the at least three components are formed by detachable components which are detachably connectable to the first brace body such that the detachable components are located between the first brace body and the person when the first brace body is wrapped around the person to provide additional support to the torso of the person to facilitate maintaining the torso in a contoured configuration. The detachable components can be adjusted via heating and cooling thereof to allow a shape to be changed to provide the contoured configuration customized for the person.

In another aspect, the present invention is directed to a body brace kit that is customizable for use in supporting at least a portion of a torso of a person including at least three components. One of the at least three components is a first brace body configured to wrap around a portion of a torso of the person to provide support to the torso and generally define a central in-use axis. Two of the at least three components are formed by detachable components which are detachably connectable to the first brace body such that the detachable components are located between the first brace body and the person when the first brace body is wrapped around the person to provide additional support to the torso of the person to facilitate maintaining the torso in a contoured configuration.

In another aspect, the present invention is directed to a body brace that is customizable for use in supporting at least a portion of a torso of a person. The kit may include at least three components. One of the at least three components is a first brace body configured to wrap around a portion of a torso of the person to provide support to the torso and generally define a central in-use axis. The at least three components further comprise two lower back support pads which are configured to be located along a back of the person when used with the first brace body wrapped around the person. Wherein all of the at least three components, except for the first body brace, are: (1) detachably attachable to the first brace body; and (2) can be adjusted via heating and cooling thereof to allow a shape to be changed to provide the contoured configuration customized for the person.

In another aspect, the present invention is directed to a body brace that is customizable for use in supporting at least a portion of a torso of a person. The body brace may include at least three components. One of the at least three components is a first brace body configured to wrap around a portion of a torso of the person to provide support to the torso and generally define a central in-use axis. The at least three components further comprise two lower back support pads which are configured to be located along a back of the person when used with the first brace body wrapped around the person.

In another aspect, the present invention is directed to a body brace that is customizable for use in supporting at least a portion of a torso of a person. The body brace may include at least three components. One of the at least three components is a first brace body configured to wrap around a portion of a torso of the person to provide support to the torso and generally define a central in-use axis. The at least three components further comprise a first torso support wing and a second torso support wing, each including: a plurality of encased struts aligned generally side-to-side and each having a longitudinal side facing the longitudinal side of an adjacent one of the plurality of encased struts. The first torso support wing and the second torso support wing are configured to encircle the torso of a person to provide resistance against lateral bending of the person. Wherein all of the at least three components, except for the first body brace, are: (1) detachably attachable to the first brace body; and (2) can be adjusted via heating and cooling thereof to allow a shape to be changed to provide the contoured configuration customized for the person.

In another aspect, the present invention is directed to a body brace that is customizable for use in supporting at least a portion of a torso of a person. The body brace may include at least three components. One of the at least three components is a first brace body configured to wrap around a portion of a torso of the person to provide support to the torso and generally define a central in-use axis. The at least three components further comprise a first torso support wing and a second torso support wing, each including: a plurality of encased struts aligned generally side-to-side and each having a longitudinal side facing the longitudinal side of an adjacent one of the plurality of encased struts. The first torso support wing and the second torso support wing are configured to encircle the torso of a person to provide resistance against lateral bending of the person.

In another aspect, the present invention is directed to a body brace that is customizable for use in supporting at least a portion of a torso of a person. The body brace may include at least three components. One of the at least three components is a first brace body configured to wrap around a portion of a torso of the person to provide support to the torso and generally define a central in-use axis. The at least three components further comprise a shell positionable on the first brace body and configured to contact a greater portion of a back of the person than the first brace body. The shell being configured to maintain the back in a contoured configuration and to provide resistance against bending in a manner that does not conform with the contoured configuration. The at least three components further comprise a chest support member positionable on the first brace body and configured to contact a greater portion of the chest of the person than the first brace body. The chest support being configured to maintain the chest in a second contoured configuration and to provide resistance against bending in a manner that does not conform with the second contoured configuration. Wherein all of the at least three components, except for the first body brace, are: (1) detachably attachable to the first brace body; and (2) can be adjusted via heating and cooling thereof to allow a shape to be changed to provide the contoured configuration customized for the person.

In another aspect, the present invention is directed to a body brace that is customizable for use in supporting at least a portion of a torso of a person. The body brace may include at least three components. One of the at least three components is a first brace body configured to wrap around a portion of a torso of the person to provide support to the torso and generally define a central in-use axis. The at least three components further comprise a shell positionable on the first brace body and configured to contact a greater portion of a back of the person than the first brace body. The shell being configured to maintain the back in a contoured configuration and to provide resistance against bending in a manner that does not conform with the contoured configuration. The at least three components further comprise a chest support member positionable on the first brace body and configured to contact a greater portion of the chest of the person than the first brace body. The chest support being configured to maintain the chest in a second contoured configuration and to provide resistance against bending in a manner that does not conform with the second contoured configuration.

In another aspect, the present invention is directed to a body brace kit that is customizable for use in supporting at least a portion of a torso of a person. The body brace kit may include at least two components, one of the at least two components being a first brace body configured to wrap around the at least a portion of the torso of the person to provide support to the torso. One of the at least two components may be formed by a detachable component which is detachably connectable to the first brace body such that the detachable component is located between the first brace body and the person when the first brace body is wrapped around the person to provide additional support to the torso of the person to facilitate maintaining the torso in a contoured configuration. The detachable component can be adjusted via heating and cooling thereof to allow a shape to be changed to provide the contoured configuration customized for the person.

In another aspect, the present invention is directed to a body brace kit that is customizable for use in supporting at least a portion of a torso of a person. The body brace kit may include at least two components, one of the at least two components being a first brace body configured to wrap around the at least a portion of the torso of the person to provide support to the torso. One of the at least two components may be formed by a detachable component which is detachably connectable to the first brace body such that the detachable component is located between the first brace body and the person when the first brace body is wrapped around the person to provide additional support to the torso of the person to facilitate maintaining the torso in a contoured configuration.

In another aspect, the present invention is directed to a body brace for use in supporting at least a portion of a torso of a person. The body brace may include at least two components, one of the at least two components being a first brace body configured to wrap around the at least a portion of the torso of the person to provide support to the torso. One of the at least two components may be formed by a component that is located between the first brace body and the person when the first brace body is wrapped around the person to provide additional support to the torso of the person to facilitate maintaining the torso in a contoured configuration. The component can be adjusted via heating and cooling thereof to allow a shape to be changed to provide the contoured configuration customized for the person.

In another aspect, the present invention is directed to a body brace for use in supporting at least a portion of a torso of a person. The body brace may include at least two components, one of the at least two components being a first brace body configured to wrap around the at least a portion of the torso of the person to provide support to the torso. One of the at least two components may be formed by a component that is located between the first brace body and the person when the first brace body is wrapped around the person to provide additional support to the torso of the person to facilitate maintaining the torso in a contoured configuration.

In another aspect, the present invention is directed to a body brace that is customizable for use in supporting at least a portion of a torso of a person. The body brace comprising a lower brace body which is configured to allow the detachable securing of additional components thereto. The lower brace body including handles on an outer surface such that when wrapping the body brace around the person, the person can pull the lower body brace snugly around the person's torso prior to detachably securing the lower brace in the closed/operational position.

BRIEF DESCRIPTION OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 36 more clearly shows the underarm straps attaching to the shell which is preferably done using hook and loop material but may be done using any appropriate means. Although the straps are shown in an underarm configuration, a user can place one or more of the straps over a shoulder as desired.

FIG. 47 is a top plan view of the body brace kit in FIG. 45 illustrating the varying lengths (and thus, circumferences when wrapped) of the brace body and torso wings. The first and second torso wings are attached to the interior face of the brace body.

FIG. 48 is a front elevational view of the body brace kit in FIG. 45 illustrating the side supports do not extend beyond either the upper or lower edge of the brace body and are thus non-protruding.

DETAILED DESCRIPTION OF THE PREFERRED EMBODIMENTS

Figure 1:
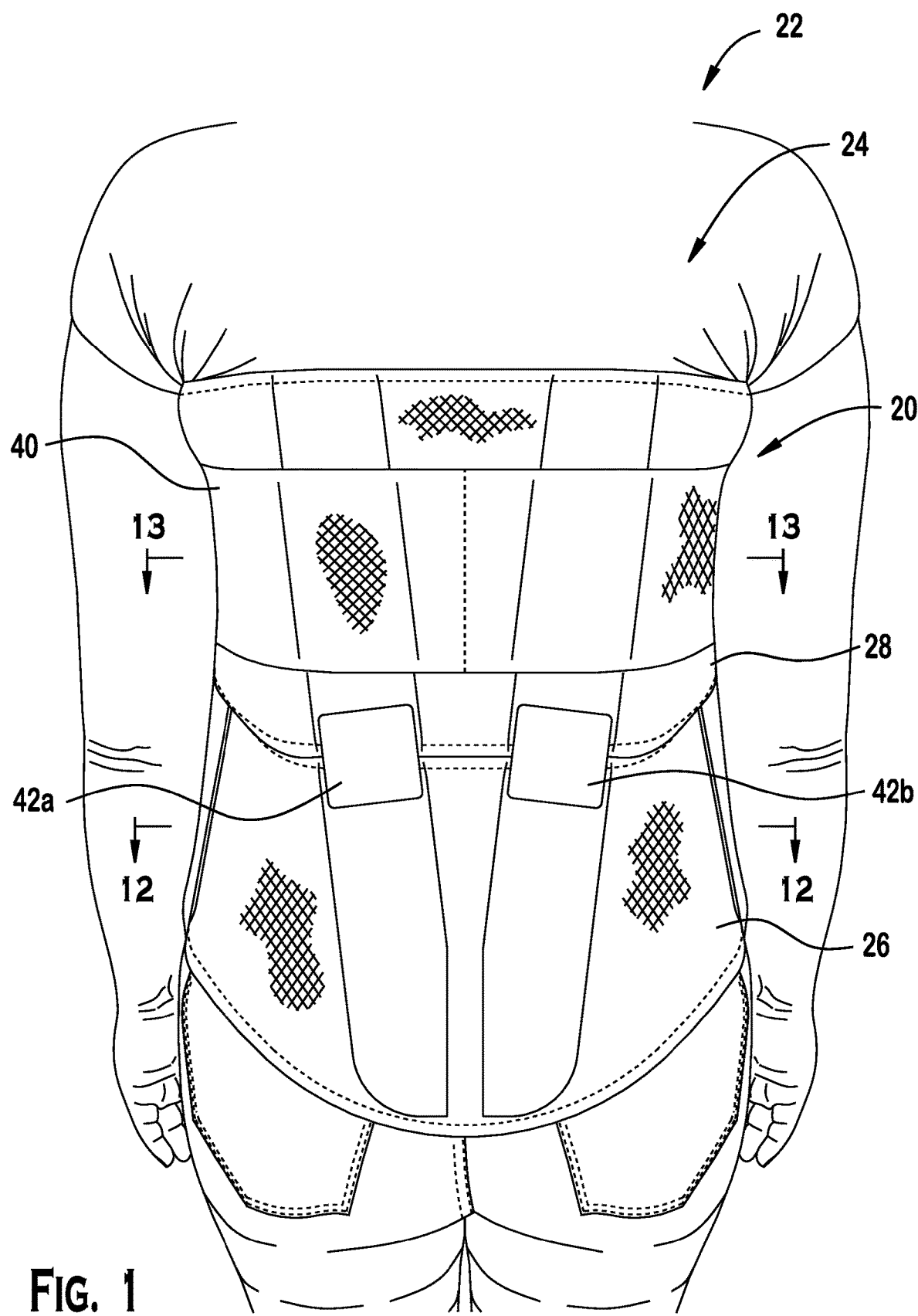
FIG. 1 is a rear perspective view of a preferred embodiment of the body brace according to the present invention. The body brace is shown being worn by a person on a portion of the person's torso. Those of ordinary skill in the art will appreciate from this disclosure, however, that the body brace may be worn differently and over different parts of the torso by different users, such as being worn as low as the hips and as high as the shoulders, without departing from the scope of the invention.

Certain terminology is used in the following description for convenience only and is not limiting. The words "right", "left", "top", "bottom", designate directions in the drawings to which reference is made. The term "brace" as used in the claims and associated portions of the specification is defined as meaning "any therapy, splint, medical, or aid device used for the support and/or immobilization of body parts." "Vertical" refers to a generally up and down position, while "horizontal" refers to a position which generally bisects a vertical and horizontal axis if each were to continue in infinitum. The language "at least one of 'A', 'B', and 'C'," as used in the claims and in corresponding portions of the specification, means "any group having at least one 'A'; or any group having at least one 'B'; or any group having at least one 'C'; —and does require that a group have at least one of each of 'A', 'B', and 'C'." More specifically, the language 'at least two/three of the following list' (the list itemizing items '1', '2', '3', '4', etc.), as used in the claims, means at least two/three total items selected from the list and does not mean two/three of each item in the list. The term "interior", as used in the claims and corresponding portions of the specification means the area proximate to the center of the invention. The term "exterior" similarly defines the area not in proximity to the center of the invention. Additionally, the words "a" and "one" are defined as including one or more of the referenced items unless specifically stated otherwise. The terminology includes the words above specifically mentioned, derivatives thereof, and words of similar import.

Figure 59:
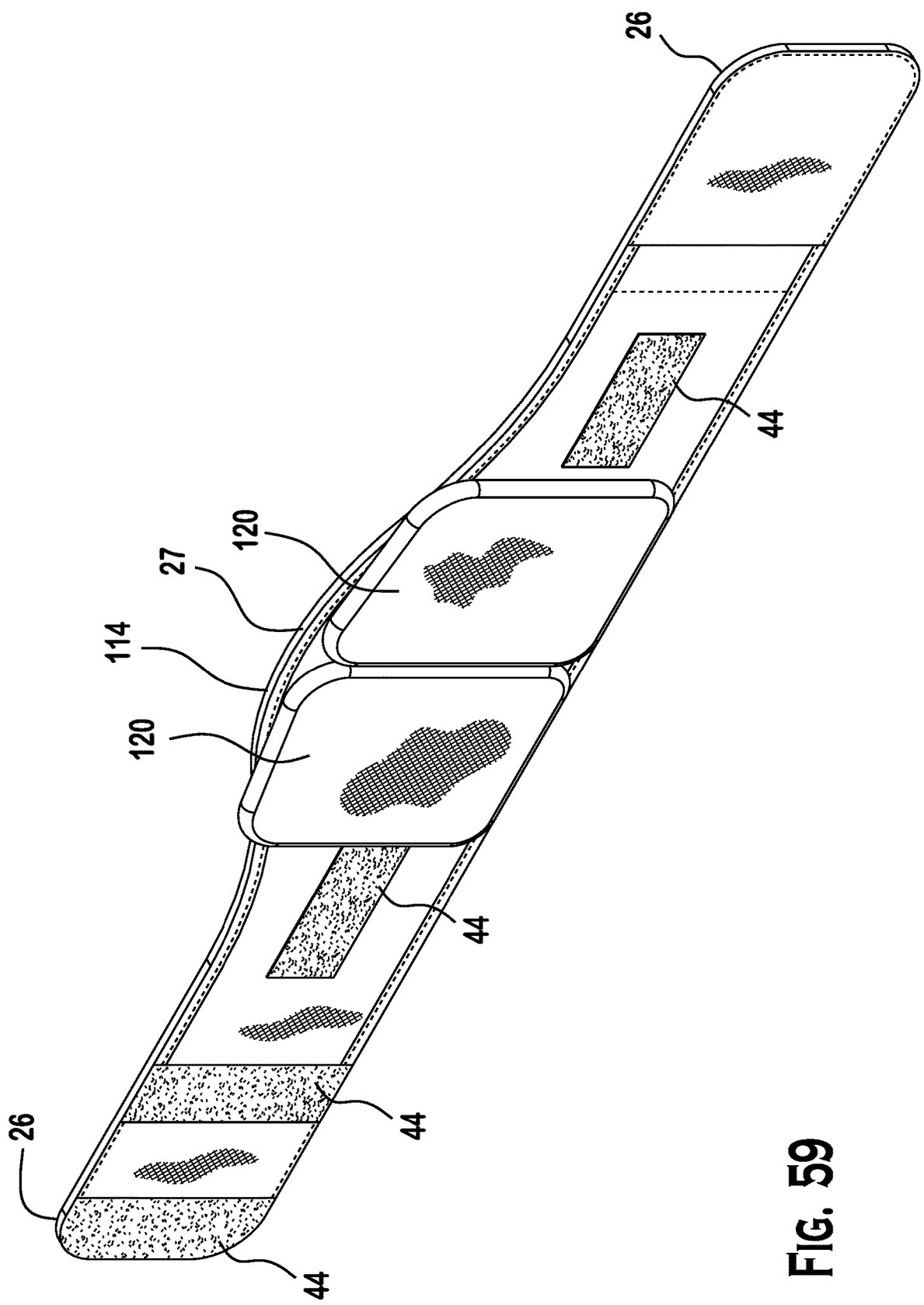
FIG. 59 is a front, top, right, perspective view of a body brace kit according to an eighth preferred embodiment. The Figure illustrates a brace body with two lower back support pads attached to the interior. It is preferred, but not necessary that there be an additional panel of hook and loop or connecting material to allow for a tighter connection.

Referring to FIGS. 1-59, wherein like numerals indicate like elements throughout, preferred embodiments of a body brace and/or body brace kit according to the present invention are shown and generally designated as 20. Briefly speaking the body brace 20 can be worn around a person's torso when he or she is looking to provide additional support and/or immobilization to promote health and recovery.

Referring now to FIG. 1, the body brace 20 is preferably formed from a flexible, synthetic material such that the body brace 20 may contour to the shape of the torso 24 of a person 22. However those of ordinary skill in the art will appreciate from this disclosure that any material, such as a cloth, bandage wrap, or the like, may be used without exceeding the scope of the invention. The body brace 20 is shown fully wrapped around a portion of the torso 24 of the person 22. However, those of ordinary skill in the art will appreciate from this disclosure that the body brace 20 need only cover a portion of the person's torso 24, and so may not fully wrap around a person's torso 24.

Figure 2:
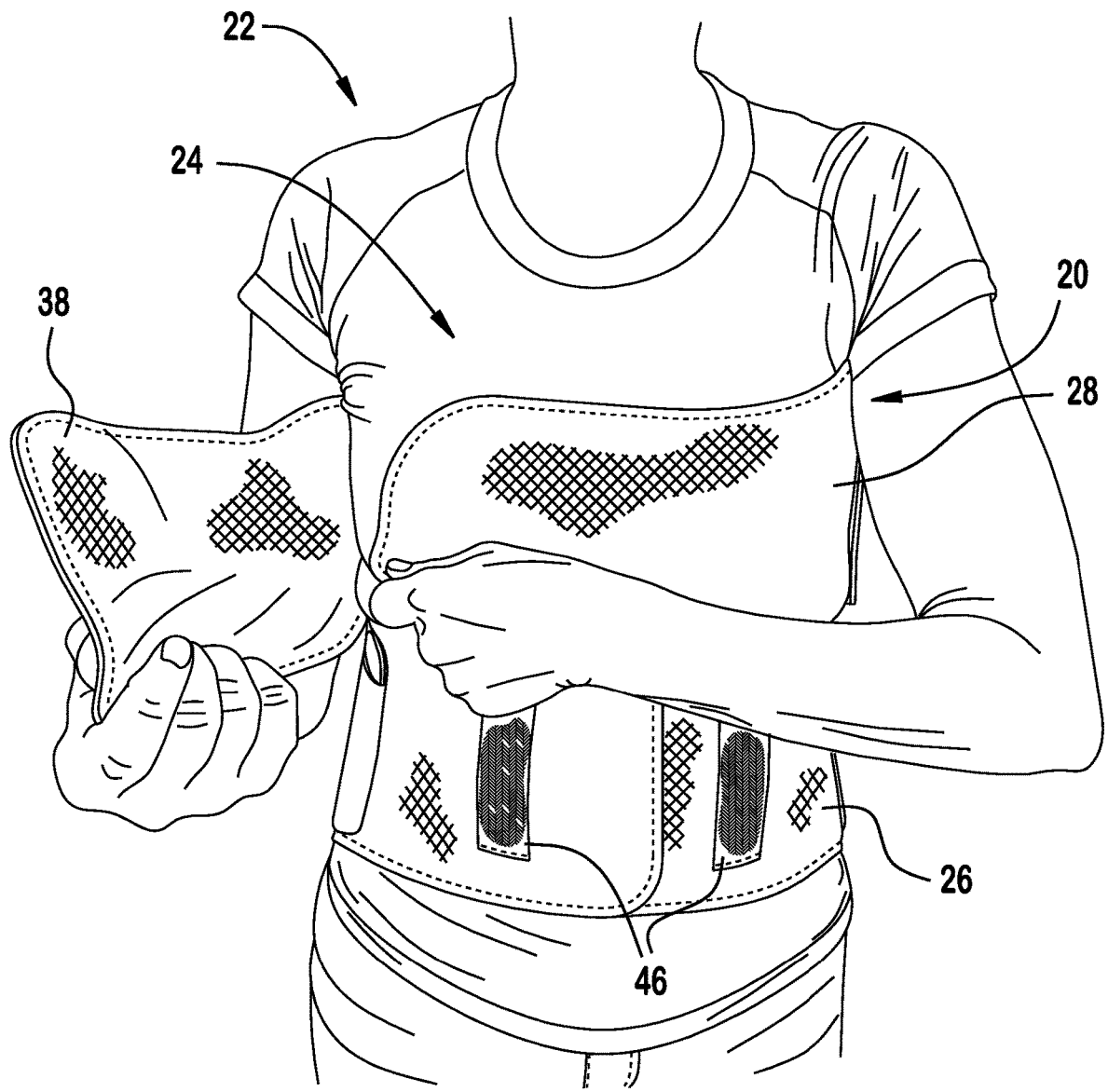
FIG. 2 is a front perspective view of a body brace according to a preferred embodiment of this invention. The body brace is shown with the first brace body being already wrapped around a first portion of the person's torso and the second brace body being partially fastened by a person to cover a second portion of the person's torso. Those of ordinary skill in the art will appreciate from this disclosure, however, that the body brace may be worn or fastened differently without departing from the scope of the invention.

Referring to FIG. 2, the body brace 20 may include a first brace body 26 which may fasten about the wearer's front using a first fastening element 36. In some embodiments, the body brace 20 may include both a first brace body 26 and second brace body 28 which may each fasten about the wearer's front using a first fastening element 36 and second fastening element 38 respectively. Preferably, the first and second fastening elements 36, 38 are formed of hook-and-loop material, such as VELCRO®-brand hook-and-loop fastener. However, those of ordinary skill in the art will appreciate from this disclosure that the fastening elements 36, 38 may be formed of any suitable fastening, means such as buttons, snaps, zippers, magnets, and more without exceeding the scope of this disclosure. Those of ordinary skill in the art will further appreciate from this disclosure that the first and second fastening elements 36, 38 may be formed of different fastening means from each other without exceeding the scope of this disclosure.

Referring to FIGS. 3-5 and 12, a first preferred embodiment of the body brace 20 of the present invention is shown. Preferably, the body brace 20 is customizable for use in supporting at least a portion of a torso 24 of a person 22. The body brace 20 may include a first brace body 26 configured to wrap around and/or cover at least a portion of a torso 24 of the person 22 to provide additional support to the torso 24 to help portions of the body heal. The first brace body 26 preferably includes at least one support pocket 32 therein, into which a support member 30 may be placed, and may be held therein. The support pockets 32 are preferably formed between layers of the first brace body 26 but may be affixed to the exterior or interior thereof. Those of ordinary skill in the art will appreciate from this disclosure that the first brace body 26 may include multiple support pockets 32, that these support pockets 32 may each be formed separately between the layers of the first brace body 26, or affixed to the exterior or interior sides thereof, without exceeding the scope of this disclosure.

The first brace body 26 may include as few as one support member 30 and one support pocket 32 or as many as ten or more support members 30 and corresponding support pockets 32 therein. These support members 30, and their corresponding support pockets 32, are preferably spaced apart along the first brace body 26. Those of ordinary skill in the art will appreciate from this disclosure that any number or configuration of support pockets 32 and support members 30 may be provided without exceeding the scope of this disclosure.

Preferably, the support member 30 provides significant rigidity to the body brace 20. The support member 30 is preferably configured to be inserted into the support pocket 32 to provide a contoured configuration to the first brace body 26. In this way, the support member 30 may provide resistance against bending the torso 24 in a manner which might drive the first brace body 26 out of the contoured configuration. In some embodiments, the support member 30 may be removeable from and insertable into the support pocket 32. In other words, in some embodiments the support member 30 may be inserted or removed from the support pocket 32 at will, even when in use.

Referring to FIGS. 3-9, in some embodiments the first brace body 26 may alternatively include one or more V-shape support pockets 33 into which V-shape support members 31 may be removably positioned. In such embodiments, it is important to note that the V-shape support pockets 33 and V-shape support members 31 are not actually themselves V-shapes. Nor are these elements necessarily distinct from support pockets 32 or support members 30 generally. Rather, the V-shape support pockets 33 and V-shape support members 31 are terms used for convenience to refer to support pockets 32 or support members 30 which may be positioned in a V-shape 52 along a vertical axis 50 of the body brace 20. It is preferred that this mirror image angles from the vertical axis 50 at less than 45 degree angles. However, those of ordinary skill in the art will appreciate from this disclosure that minor image angles may be any degree less than 90 degrees from the vertical axis without exceeding the scope of this disclosure. In some embodiments, the V-shape support pockets 33 and V-shape shape support members 31 may also have a single beveled edge 39 to be positioned at a diagonal angle from an imaginary vertical axis 50. It is preferred that two V-shape support pockets 33 and V-shape support members 31 be provided, with the first V-shape support pocket 33a and V-shape support member 31a being positioned in a roughly minor-image position about the vertical axis 50 compared to the second V-shape support pocket 33b and V-shape support member 31b.

In summary, the body brace 20 may be customizable for use in supporting at least a portion of a torso 24 of a person 22. The body brace 20 may include a first brace body 26 configured to wrap around a portion of a torso 24 of the person 22 to provide support thereto, and a second brace body 28 configured to wrap around a second portion of the torso 24 of the person 22. The first brace body 26 and second brace body 28 preferably do not overlap, and instead may be connected by at least one linkage block 42 connected to the first brace body 26 and the second brace body 28 via hook and loop material 44. The lateral ends of the first brace body 26 may be detachably connected to each other by one or more linkage block 42, preferably via hook-and-loop material 44, to detachably secure the first brace body 26 around a first portion of the torso 24 of the person 22. Similarly, lateral ends of the second brace body 28 may alternatively or also be detachably connected by at least one linkage block 42, preferably via hook-and-loop material 44, to detachably secure the second brace body 28 around a second portion of the torso 24 of the person 22. The first brace body 26 may include at least two support pockets 32 therein, with two of the support pockets 32 being positioned on the first brace body 26 in minor-image angles from each other along a vertical axis 50 of the body brace 20. These may be called V-shape support pockets 31. Similarly, the second brace body 28 may include at least two guide pockets 34 therein, with two of the at least two guide pockets 34 positioned on the second brace body 28 in mirror-image angles from the vertical axis 50 of the body brace 20. The first brace body 26 and second brace body 28 may be detachably connected to one another. The body brace 20 may include at least two support members 30, with two of the at least two support members 30 being positionable in the V-shape support pockets 31 and the two guide pockets 34 such that the two support members 30 may be held in mirror image angles from the vertical axis 50. These are a sub-set of support members 30 and may be called V-shape support members 31. Through such a configuration, the V-shape support members 31 may provide a contoured configuration to the first brace body 26 and provide resistance against bending the torso in a manner to drive the first brace body 26 and/or the second brace body 28 out of the contoured configuration. In some embodiments, the two of the at least two support members 30 (also known as the V-shape support members 31) and the two of the at least two support pockets 32 (also known as the V-shape support pockets 33) may also include one beveled edge 39 along a corner of each, positionable parallel to the vertical axis. In other embodiments, third and fourth support pockets 32a, 32b may be positioned along separate lateral ends of the first brace body 26, with third and fourth support members 30a, 30b being removably positionable within the third and fourth support pockets 32a, 32b. In such an embodiment, the third and fourth support members 30a, 30b would preferably be of a short enough height that the do not overlap the second brace body 28 and thus do not fit into guide pockets 34. This allows the person 22 to retain a greater range of movement in his or her arms when wearing the body brace 20. In some embodiments, the shape of any or all of the at least two support members 30 (including any or all of the V-shape support members 31) may be adjusted via heating and cooling thereof to allow the support member to provide the contoured configuration customized for the person. The second brace body 28 may also include a lateral support accessory 40 which may be detachably secured there, extending laterally to cover at least the two guide pockets 24. This can better ensure the V-shape 52 in maintained. The lateral support accessory 40 is preferably attached to the exterior of the second brace body 28. However, those of ordinary skill in the art will appreciate from this disclosure that the lateral support accessory 40 may be included on either the exterior or interior of the second brace body 28, or even on the first brace body 26 in the place of or in addition to the second brace body 28, without exceeding the scope of this disclosure. The shape of the any of the support members are preferably adjustable via microwave heating, donning/wearing to mold directly on the person, and cooling thereof to allow the support member to provide the desired contoured configuration customized for the person It is preferred that the beveled edges 39 are parallel to the vertical axis 50, forming the bottom portion of the V-shape. However, those of ordinary skill in the art will appreciate that the V-shape support pockets 33 and V-shape support members 31 need not mirror each other about the vertical axis 50 or have a beveled edge 39. Those of ordinary skill in the art will appreciate from this disclosure that any number of V-shape support pockets 33 and V-shape support members 31 may be provided in the place of, or in addition to support members 30 and support pockets 32 without exceeding the scope of this disclosure. In some embodiments, the V-shape support member 31 may be removeable from, and insertable into, the V-shape support pocket 33 such that the V-shape support member 31 may be inserted or removed from the V-shape support pocket 33 at will, even when in use.

The angle generally formed between the longitudinal axis 52 of each of the first and second the V-shaped supports 31a, 31b and the vertical axis 50 is preferably, but not necessarily equal. In some embodiments it is preferred that that the angles of the between the longitudinal axis 52 of each of the first and second the V-shaped supports 31a, 31b and the vertical axis 50 are different. It is preferred that the angles between the longitudinal axis 52 of each of the first and second the V-shaped supports 31a, 31b and the vertical axis 50 is in the range of between approximately eighty degrees and approximately five degrees. It is more preferable that the angles are in the range of approximately sixty degrees and five degrees. It is more preferable still that the angles are in the range of approximately forty degrees and five degrees. It is yet more preferable that the angles are in the range of approximately thirty degrees and ten degrees.

Figure 12:
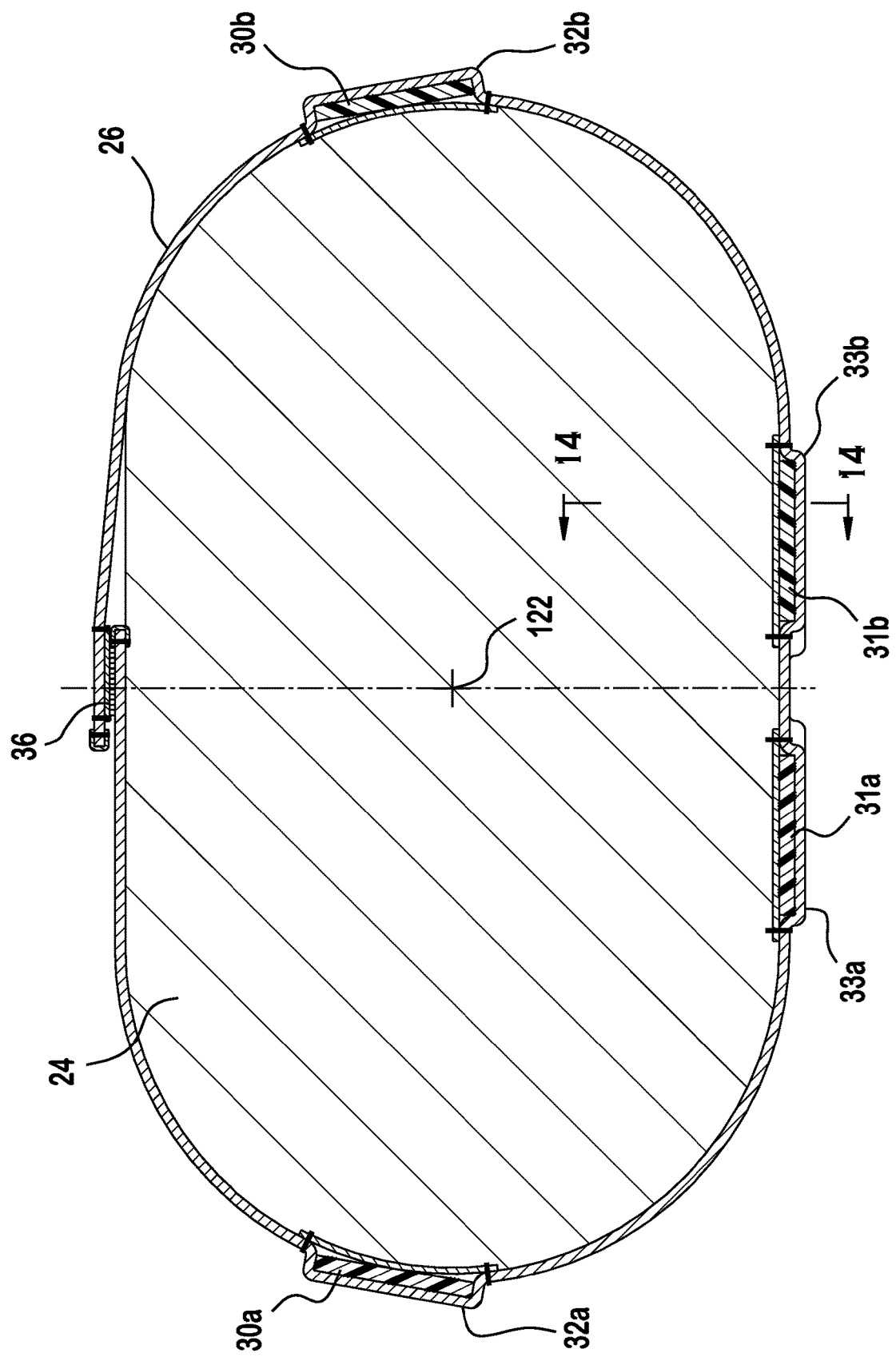
FIG. 12 is a cross-sectional view of the first brace body of the body brace of FIG. 1 as taken along Lines 12-12 of FIG. 1, demonstrating the relative position of several support members in relation to the wearer, where the first fastening element is positioned along the person's front. The evenly spaced, parallel, diagonal lines represent anything inside the inner most edge of the body brace that form no part of the invention.
Figure 13:
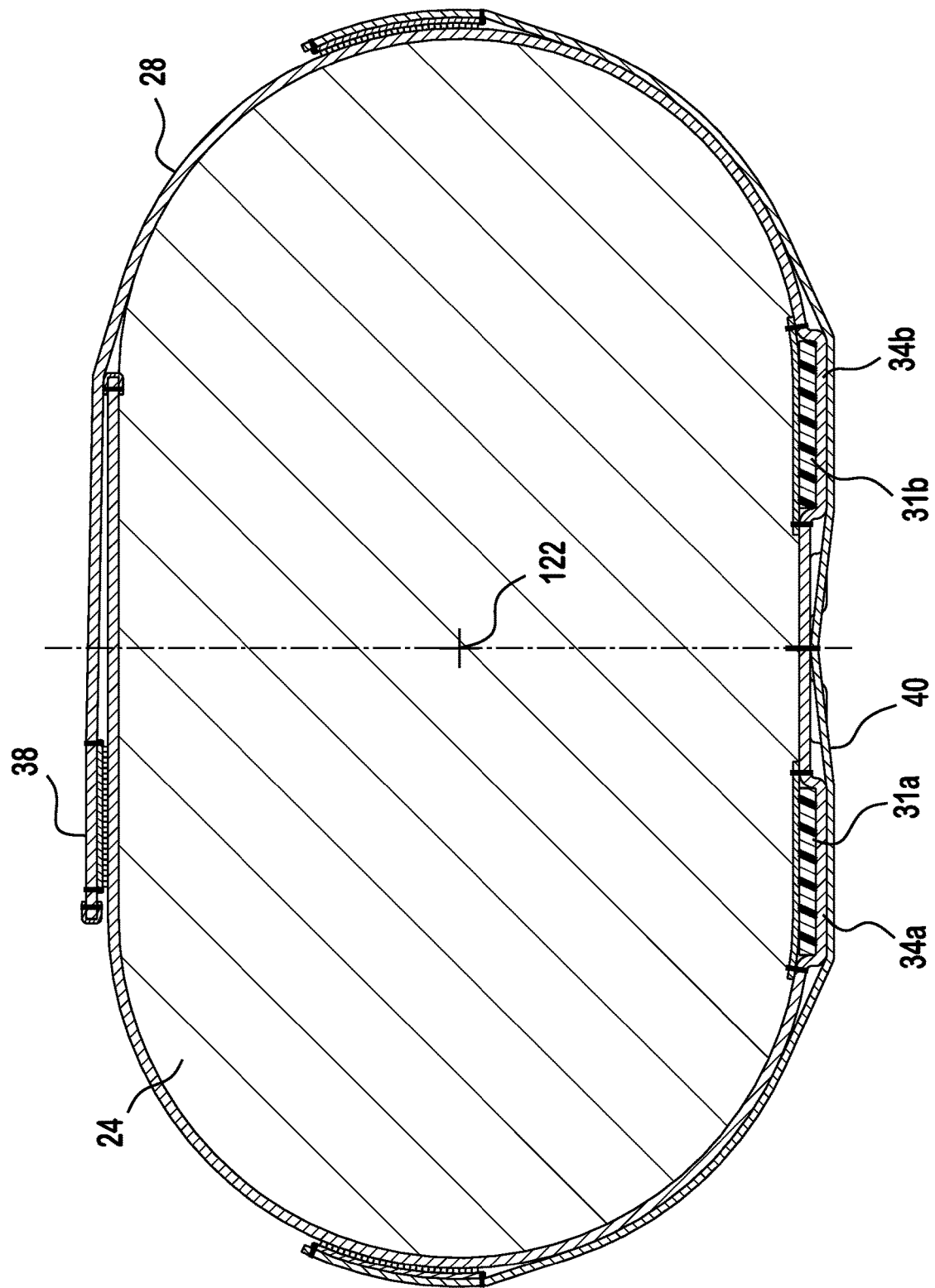
FIG. 13 is a cross-sectional view of the second brace body of the body brace of FIG. 1 as taken along Lines 13-13 of FIG. 1 demonstrating the relative position of several support members and the lateral support accessory in relation to the person, where the second fastening element is positioned along the person's front. The evenly spaced, parallel, diagonal lines represent anything inside the inner most edge of the body brace that form no part of the invention.

Referring to FIG. 12, it is preferred that some of the support members 30 or V-shape support members 31 be positioned proximate to the center of the person's torso 24, with the first fastening element 36 being positioned antipodal to said support members 30 or V-shape support members 31. Such a configuration may provide the best support to the person's torso 24, particularly the spine. In other preferred embodiments, additional support members 30 or V-shape support members 31 may be included along the front or sides of the person's torso 24, to provide additional support. Those of ordinary skill in the art will appreciate from this disclosure that the support members 30 or V-shape support members 31 may be positioned anywhere along the person's torso 24 without exceeding the scope of this disclosure.

Referring to FIGS. 6-11, in some embodiments, the shape of the support member 30 or V-shape support member 31 may be adjusted via heating and cooling. This may allow the support member 30 or V-shape support member 31 to provide a contoured configuration customized for the person 22, being perfectly fit to the person's torso. In embodiments with two or more support members 30 or V-shape support members 31, two or more of the support members 30 or V-shape support members 31 shapes may be adjusted via heating and cooling thereof to allow the support members 30 and/or V-shape support members 31 to provide a contoured configuration customized for the person 22, conforming to more than one area of the person's torso 24.

Figure 6:
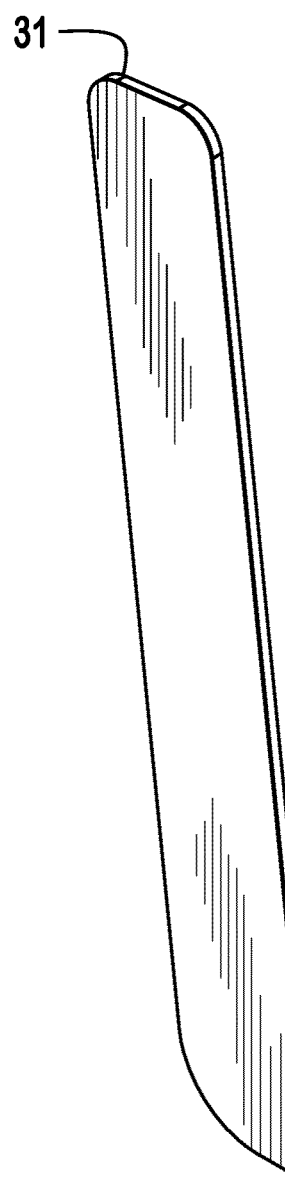
FIG. 6 is a front perspective view of a support member of a preferred embodiment, showing the preferred shape of the support member suitable for being positioned in a V-shape configuration which may be called a V-shape support member. Preferably, the V-shape support member may be generally roughly rectangular, and may have a single beveled corner to allow for better placement within non-parallel support pockets.
Figure 7:
FIG. 7 is a right side elevational view of a V-shape support member of a preferred embodiment, showing the preferred shape of the customizable support member. Preferably, the support member may be straight when no heat has been applied to it. Depending on the desired contour the support member can preferably be reconfigured to have another profile shape to allow customization of the body brace.
Figure 8:
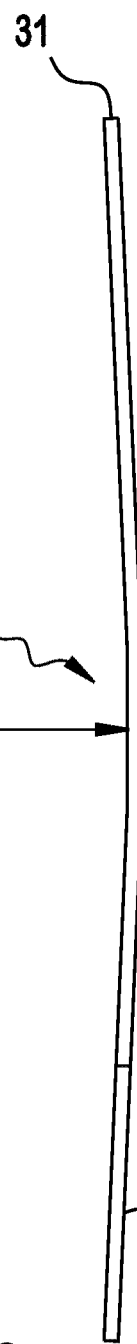
FIG. 8 is a right side elevational view of a V-shape support member of a preferred embodiment, showing the preferred shape of the customizable V-shape support member. Preferably, the V-shape support member, as with all of the support members, may have heat applied to allow it to be bent into a customized shape. The support members preferably retain such a shape when cooled.
Figure 9:
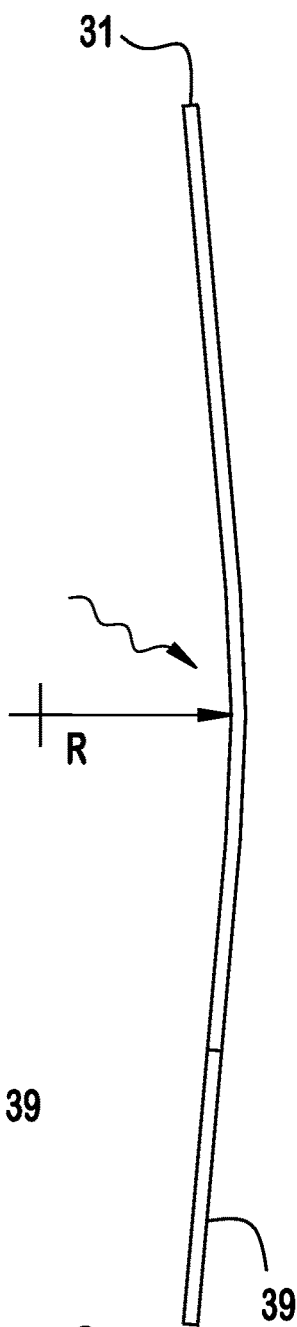
FIG. 9 is a right side elevational view of a V-shape support member of a preferred embodiment, showing a different bent shape into which the support member may be bent into.
Figure 10:
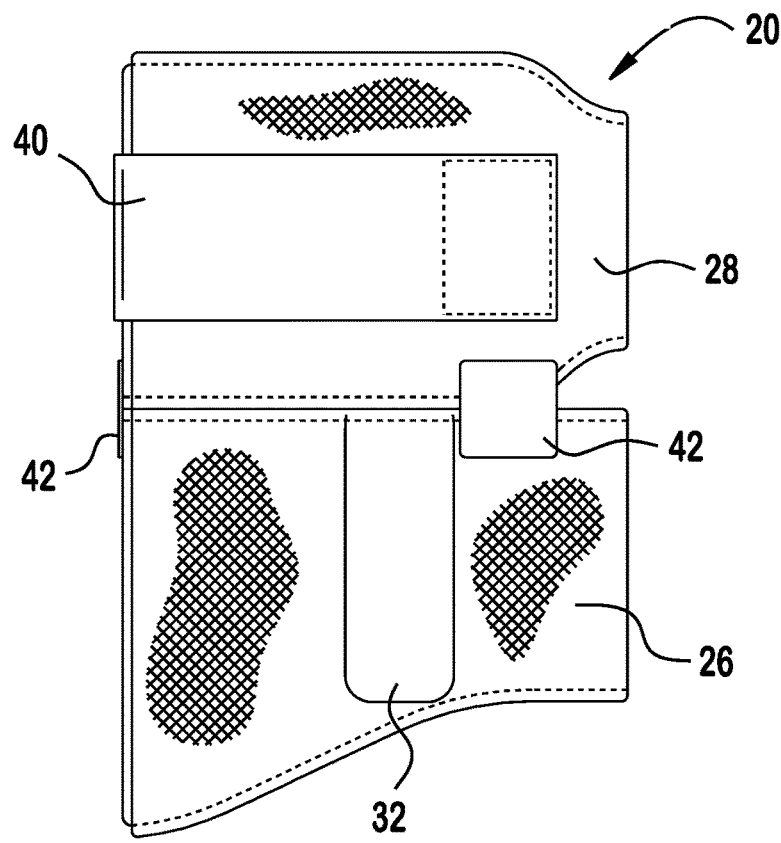
FIG. 10 is a right side elevational view of the body brace of a preferred embodiment, wherein both the first brace body and second brace body have been wrapped around separate portions of the person's torso. The figure demonstrates the shape of the body brace when straight support member has been provided.
Figure 11:
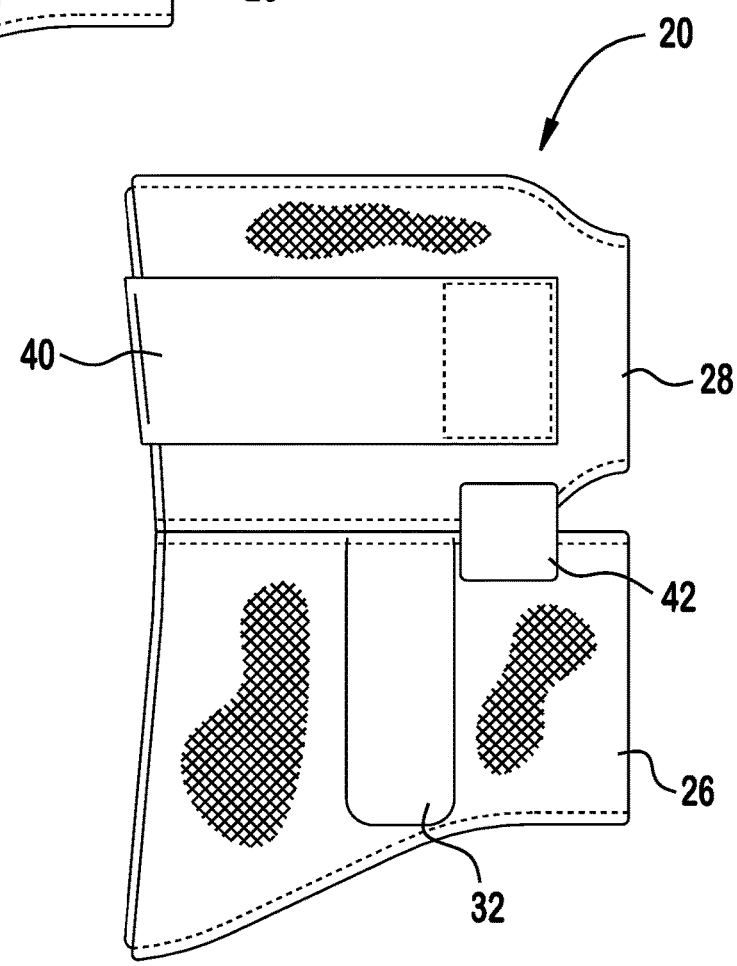
FIG. 11 is a right side elevational view of the body brace of a preferred embodiment, wherein both the first brace body and second brace body have been wrapped around separate portions of the person's torso. The figure demonstrates the shape of the body brace when one or more support member have been provided which have been shaped into customized, curved shapes.

FIG. 10 demonstrates an embodiment in which the support members 30 and/or V-shape support members 31 are provided in a standard, straight up-down-configuration, such as the configuration in FIG. 6. FIG. 11 demonstrates an embodiment in which the support members 30 and/or V-shape support members 31 are provided in a customized contoured configuration, having been shaped to fit a person such as the configuration in FIG. 9. This demonstrates the greater range of support afforded by the customized contoured configuration.

Figure 3:
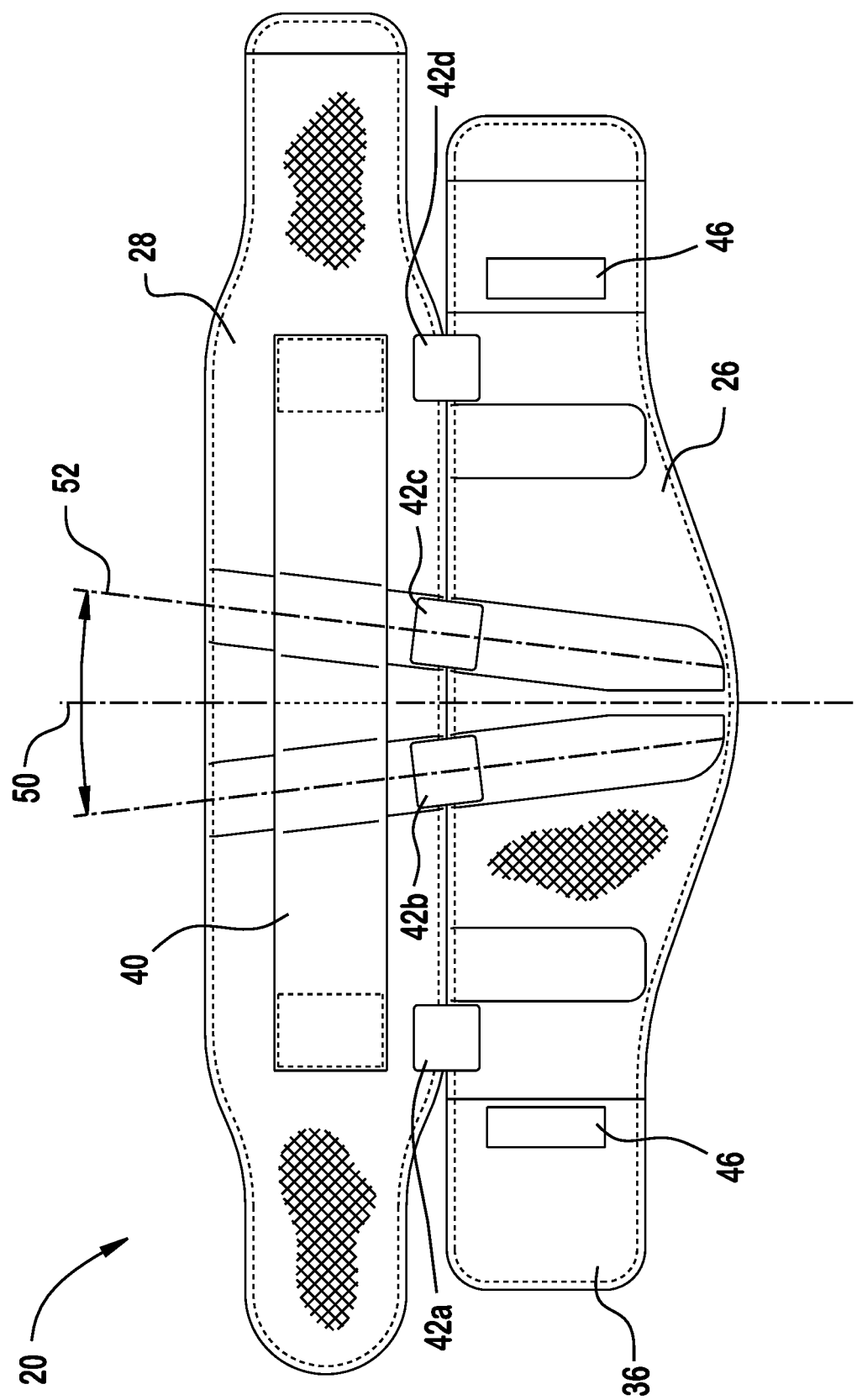
FIG. 3 is top elevational view of a body brace according to a preferred embodiment of this invention. The figure shows the first brace body is positioned below, and does not overlap with, the second brace body. The two brace bodies are preferably connected by at least one linkage block, which is preferably detachable. However, the two bodies may be connected only by the support member(s).
Figure 4:
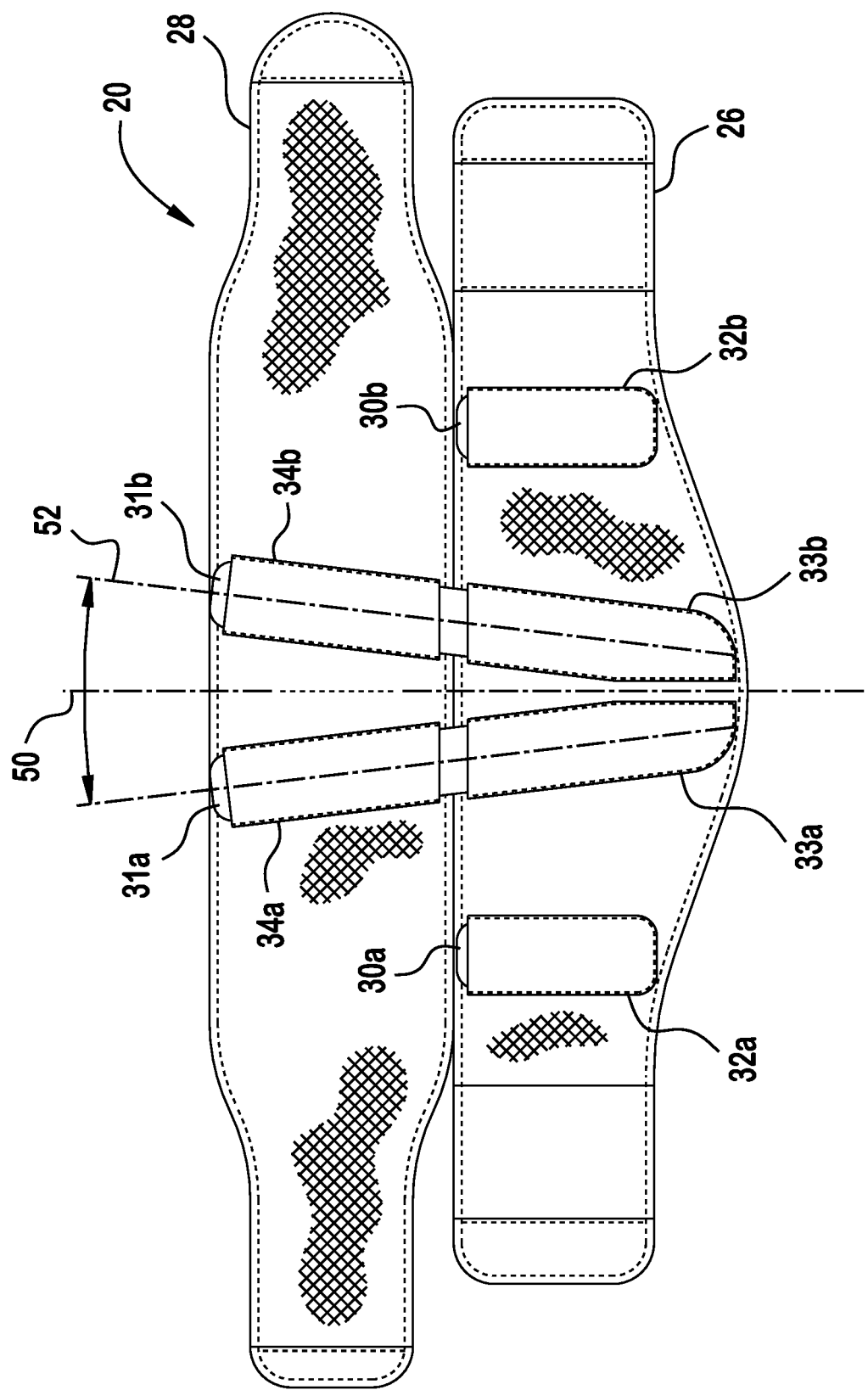
FIG. 4 is a bottom plan view of the body brace according to a preferred embodiment of this invention. The figure demonstrates that the support members may be positioned within a support pockets and a guide pocket, or only within a support pocket, depending on the size of the support member.
Figure 5:
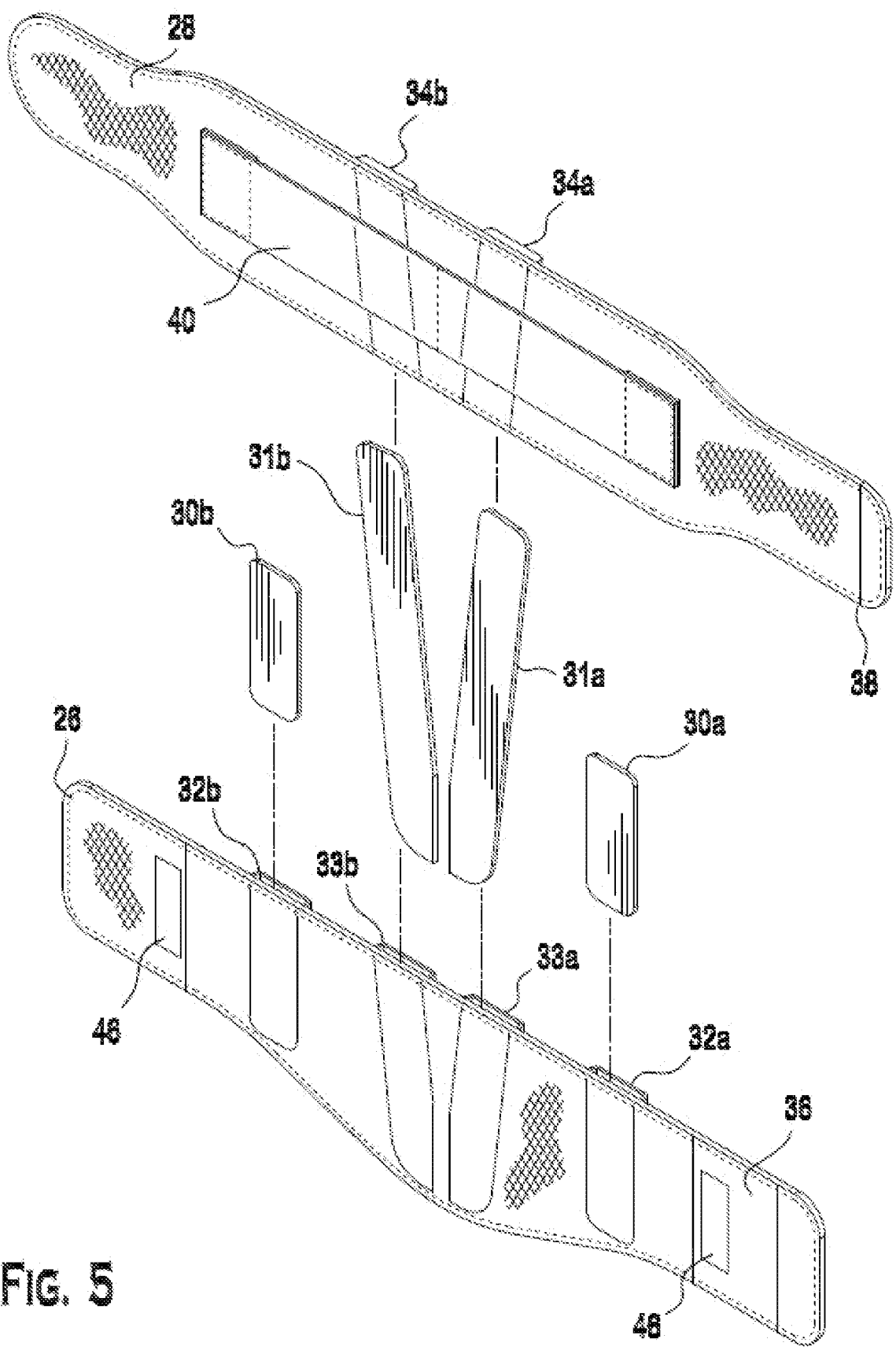
FIG. 5 is an exploded perspective view of the body brace according to a preferred embodiment of this invention, demonstrating how the support members may be inserted into the support pockets in the first brace body. The second brace body may then be lowered such that the support member may be inserted into the guide pockets.

Referring to FIGS. 3-5, in the preferred embodiment, the body brace 20 may also include a second brace body 28 configured to wrap around a second portion of the torso 24 of the person 22. The second brace body 28 preferably further includes at least one guide pocket 34 therein configured to hold the support member 30 or V-shaped support member 31 to the second brace body 28 while allowing it to pass fully through the guide pocket 34. Preferably, this may allow the support member 30 or V-shape support member 31 to be positioned in both the support pocket 32 and V-shape support pocket 33 of the first brace body and the guide pocket 34 of the second brace body 28. Such a configuration may allow the support member 28 to provide support to both higher and lower portions of the torso 24 of the person 22. In some embodiments, the guide pocket 34 may allow a V-shape support member 31 to pass therethrough. The second brace body 28 may include as few as one guide pocket 34 or as many as ten or more guide pockets 34. The guide pockets 34 are preferably spaced apart along the second brace body 28. Those of ordinary skill in the art will appreciate from this disclosure that any number or configuration guide pockets 34 can be incorporated into the body brace 20 without exceeding the scope of this disclosure. The guide pockets 34 are preferably formed between layers of the second brace body 28, but may be affixed to the exterior, interior, or some combination of all three. Those of ordinary skill in the art will appreciate from this disclosure that the second brace body 28 may include multiple guide pockets 34, that these guide pockets 34 may each be formed separately between the layers of the second brace body 28, or affixed to the exterior or interior sides thereof, without exceeding the scope of this disclosure Referring to FIGS. 3-5 and 13, the second brace body 28 may further include a lateral support accessory 40. The lateral support accessory 40 is preferably formed of a rigid or semi-rigid material to ensure that the second brace body 28 maintains its horizontal shape. However, those of ordinary skill in the art will appreciate from this disclosure that any suitable material may be used. The lateral support accessory 40 is preferably generally rectangular, and may cover any portion of the second brace body 28. It is preferred that the guide pocket 34 be affixed to the exterior of the second brace body 28 and the lateral support accessory 40 to be affixed to the interior of the second brace body 28. However, those of ordinary skill in the art will appreciate from this disclosure that the guide pockets 34 and the lateral support accessory 40 may be included on either side of the second brace body 28, including on the same side as one another, or between the layers of the second brace body 28 without exceeding the scope of this disclosure. The lateral support accessory 40 may be detachably or permanently affixed to the second brace body 40 using such affixing means as hook-and-loop material, stitching, buttons, snaps, or any other suitable affixing means.

Referring to FIGS. 3 and 14-18, it is preferred that the first brace body 26 does not overlap the second brace body 28. In one preferred embodiment, the support member 30 or V-shape support member 31 may be positioned in both the support pocket 32 (or, alternatively, the V-shape support pocket 33) of the first brace body 26 and the guide pocket 34 of the second brace body 28. In such an embodiment, the first brace body 26 and second brace body 28 may be only connected by the support member 32 (or the V-shape support pocket 33). In other preferred embodiments, the first brace body 26 may be detachably connected to the second brace body 28 through various affixing means. In one such embodiment, at least one strap may be used to detachably connect the first brace body 26 to the second brace body 28 via hook and loop material. Those of ordinary skill in the art will appreciate from this disclosure that other attachment means may be provided, such as buttons, snaps, and other attachment means, without exceeding the scope of this disclosure.

In a separate preferred embodiment, the first brace body 26 may be detachably connected to the second brace body 28 using at least one linkage block 42. The linkage block 42 is preferably rectangular in shape and formed of any suitable material, from hard materials such as molded plastic to softer materials such as fabric or synthetic fibers. Those of ordinary skill in the art will appreciate from this disclosure that the linkage block 42 may be formed of any shape and of any suitable material without exceeding the scope of this disclosure. The linkage block 42 preferably also includes an affixing means on one side which may connect the first brace body 26 to the second brace body 28. It is preferred that the linkage block 42 include at least one panel of hook-and-loop fastener 44 on one side, and a hand loop 46 on the other which facilitate removal. The linkage block 42 may further include raised edges 48. Those of ordinary skill in the art will appreciate from this disclosure that the linkage block 42 need not include the hook-and-loop fastener 44, hand loop 46, or raised edges 48. The linkage 42 may be detachably or permanently affixed to the body brace 20 using any suitable affixing in the place of or in addition to the hook-and-loop material, stitching, buttons, snaps, or any other suitable means.

Figure 14:
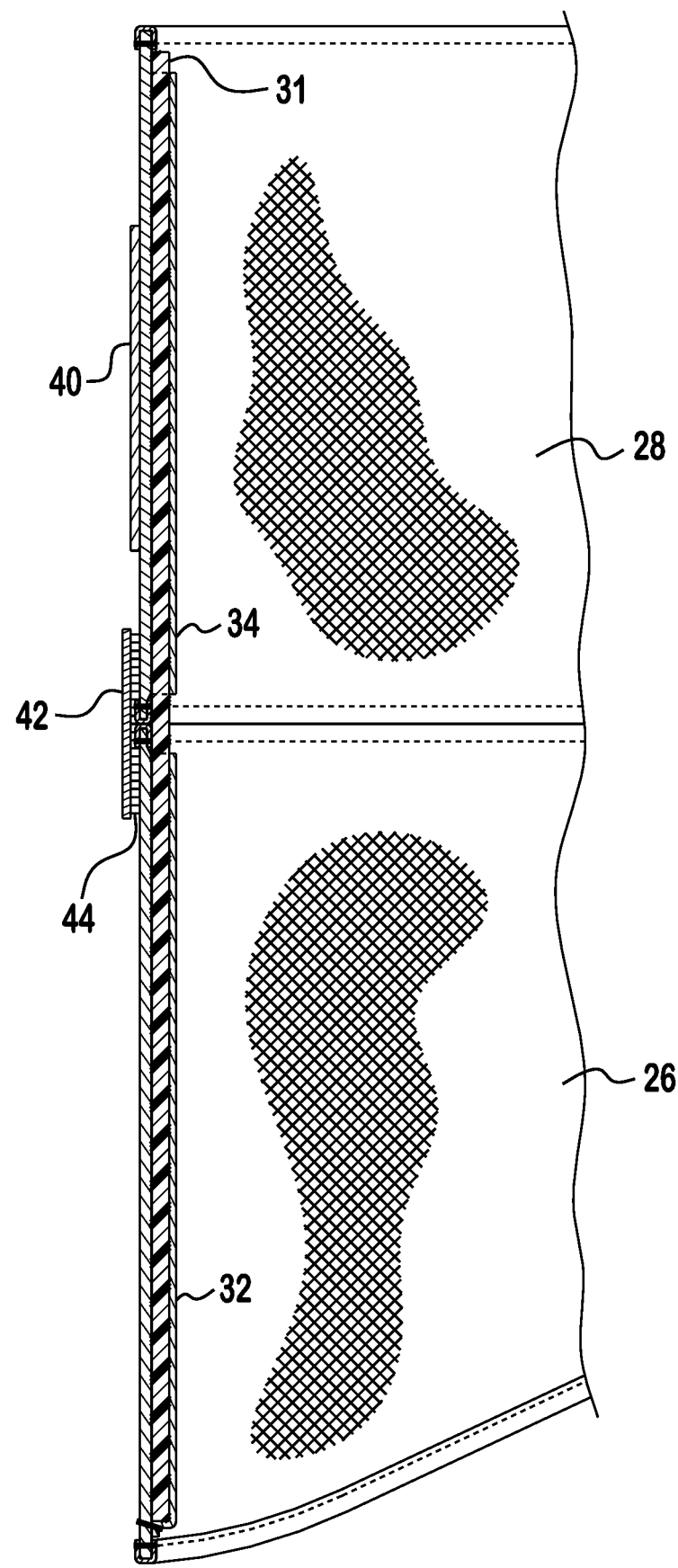
FIG. 14 is a cross-sectional view of the first and second brace bodies of the body brace as taken along Lines 14-14 of FIG. 12, showing a cross sectional view of a support member inserted into both the guide pocket and support pocket, with a linkage block connecting the first and second brace bodies.
Figure 15:
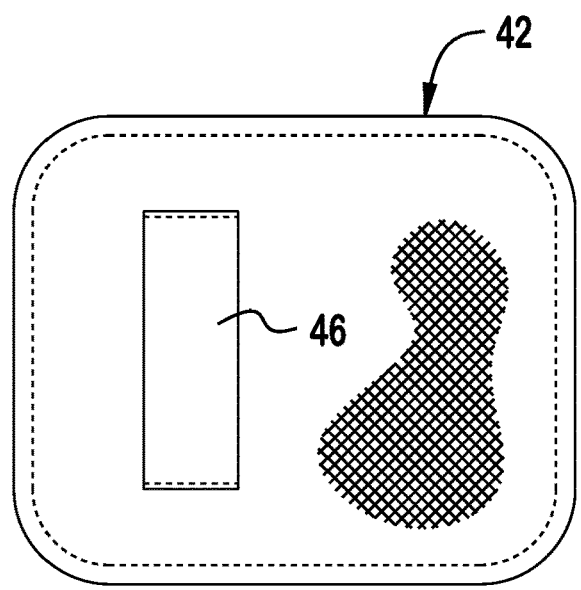
FIG. 15 is front view of the linkage block according to a preferred embodiment, showing an embodiment including raised edges and a hand loop on the front of the linkage block. These elements are optional, and one or both may be excluded in other preferred embodiments which are not pictured.
Figure 16:
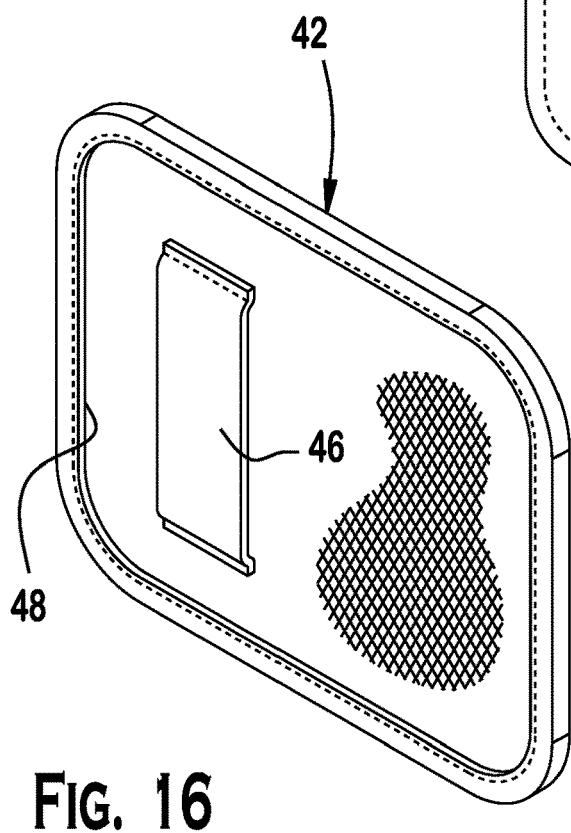
FIG. 16 is front perspective view of the linkage block according to a preferred embodiment, showing the edges and the hand loop on the front of the linkage block. The figure further demonstrates that the edges may be raised from the surface of the linkage block, and that the linkage block preferably includes slack under the hand loop for a person to hold when removing the linkage block. These elements are optional, and may be excluded in other preferred embodiments which are not pictured.
Figure 17:
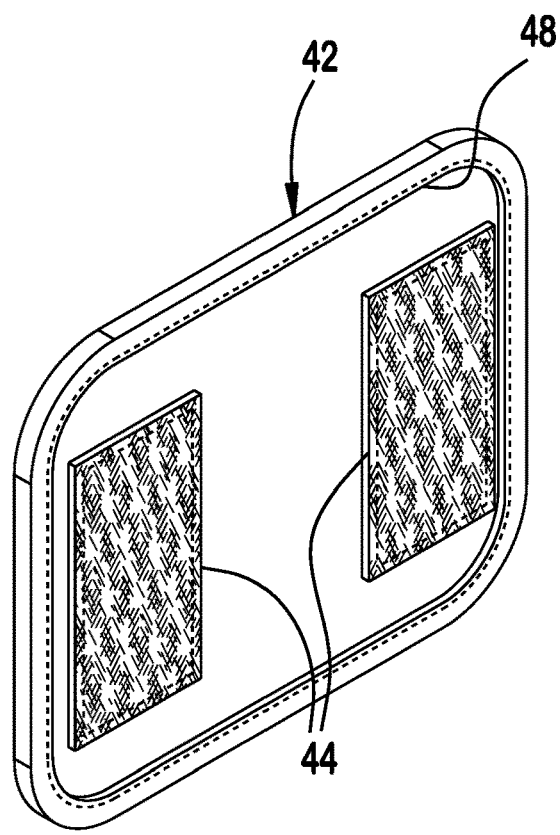
FIG. 17 rear perspective view of the linkage block according to a preferred embodiment, showing the linkage block preferably includes one or more sections of hook-and-loop fastener to allow the linkage block to connect to the first and second brace bodies. Other preferred elements of the linkage blocks which are not pictures include magnets, snaps, buttons, or any other suitable fastening means which may be included in the place of, or in addition to, the hook-and-loop fastener. The figure further demonstrates that the edges of the linkage block may also extend outward from the inner surface of the linkage block.
Figure 18:
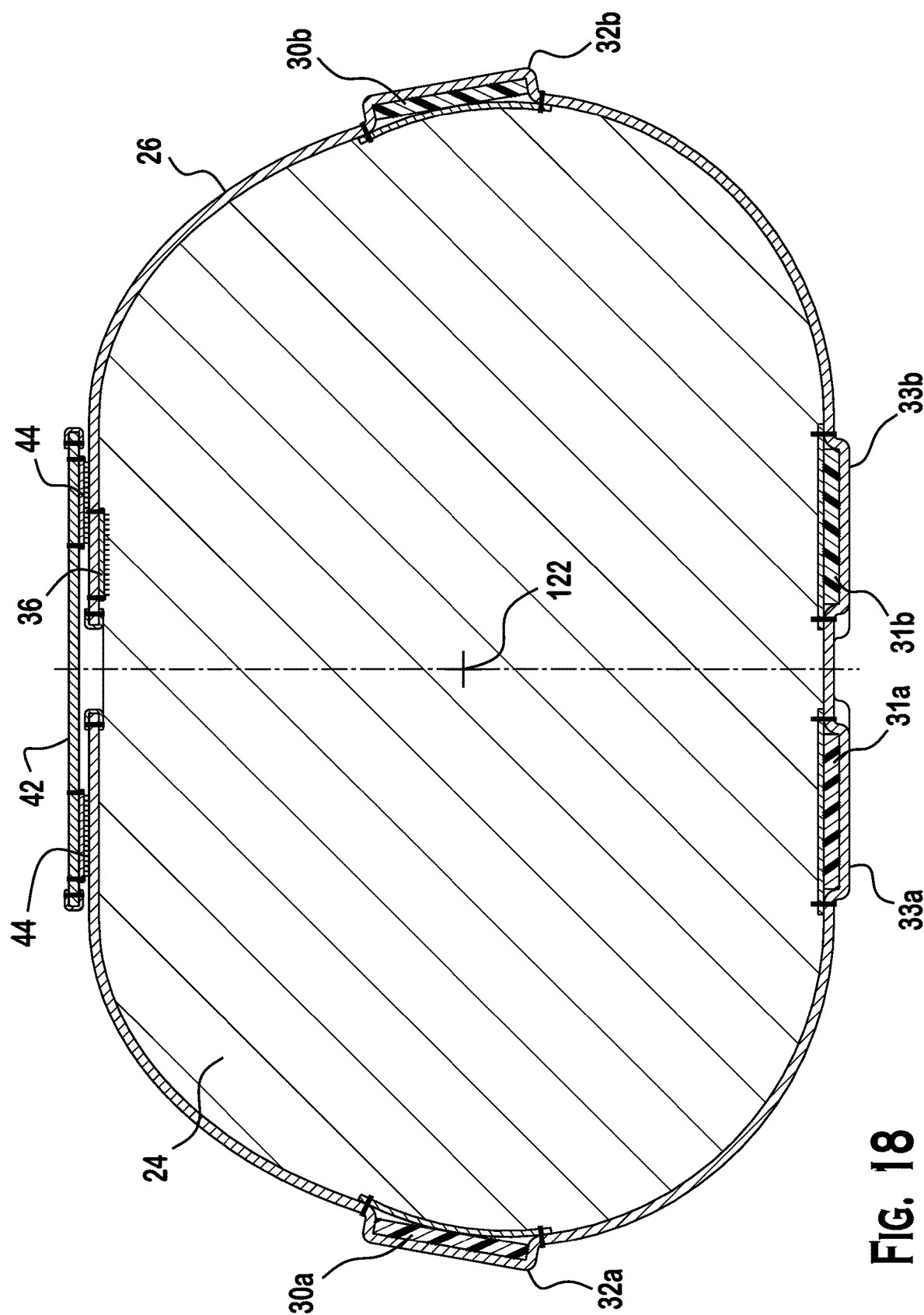
FIG. 18 is an alternate cross sectional view of the first brace body of a preferred embodiment demonstrating that a linkage block may be use in the place of the first fastening element. Those of ordinary skill in the art will appreciate from this disclosure that a linkage block may also be used in the place of the second fastening element without exceeding the scope of this disclosure.
Figure 36:
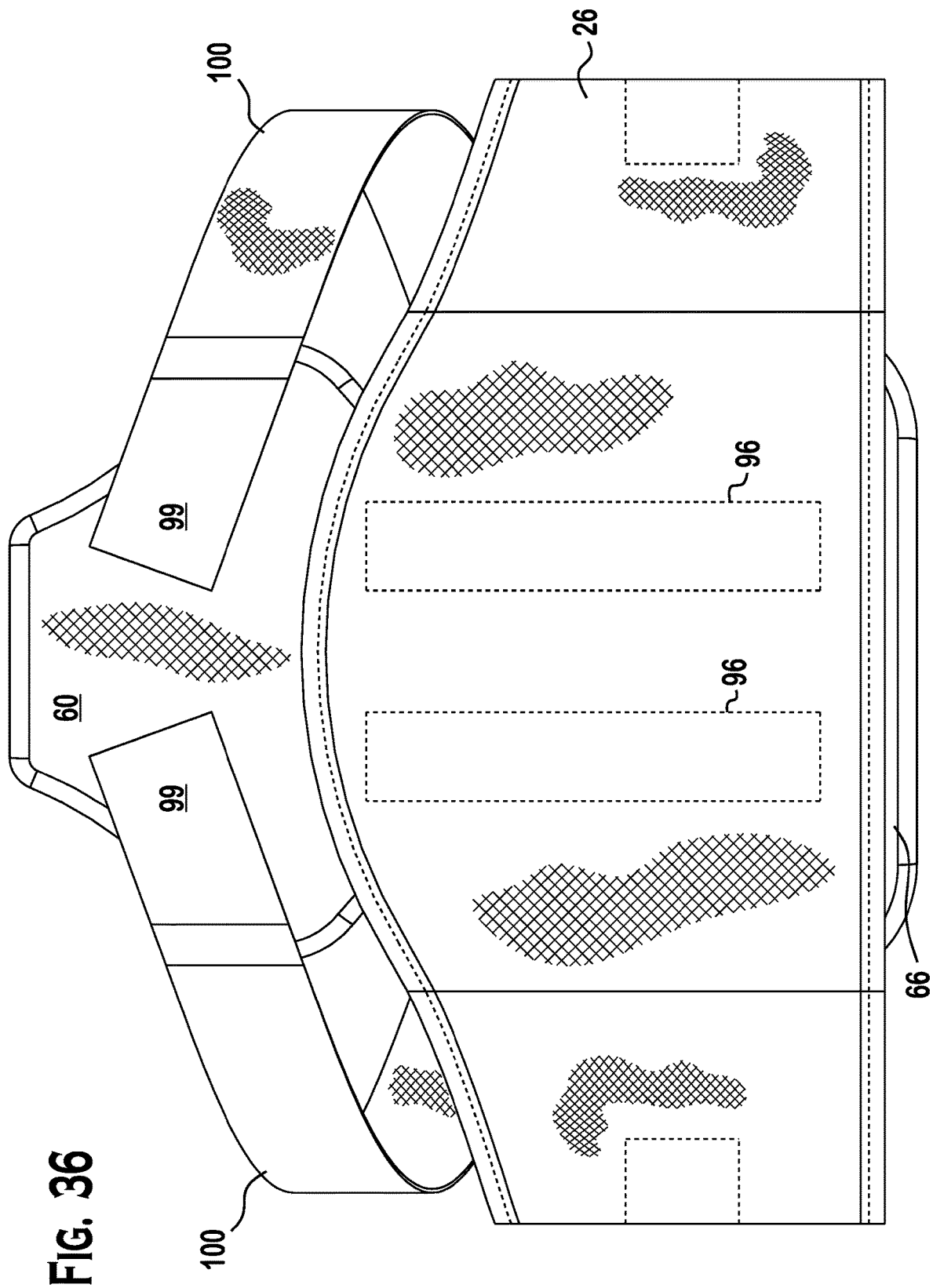
FIG. 36 is a rear elevational view of the body brace kit of FIG. 35.
Figure 37:
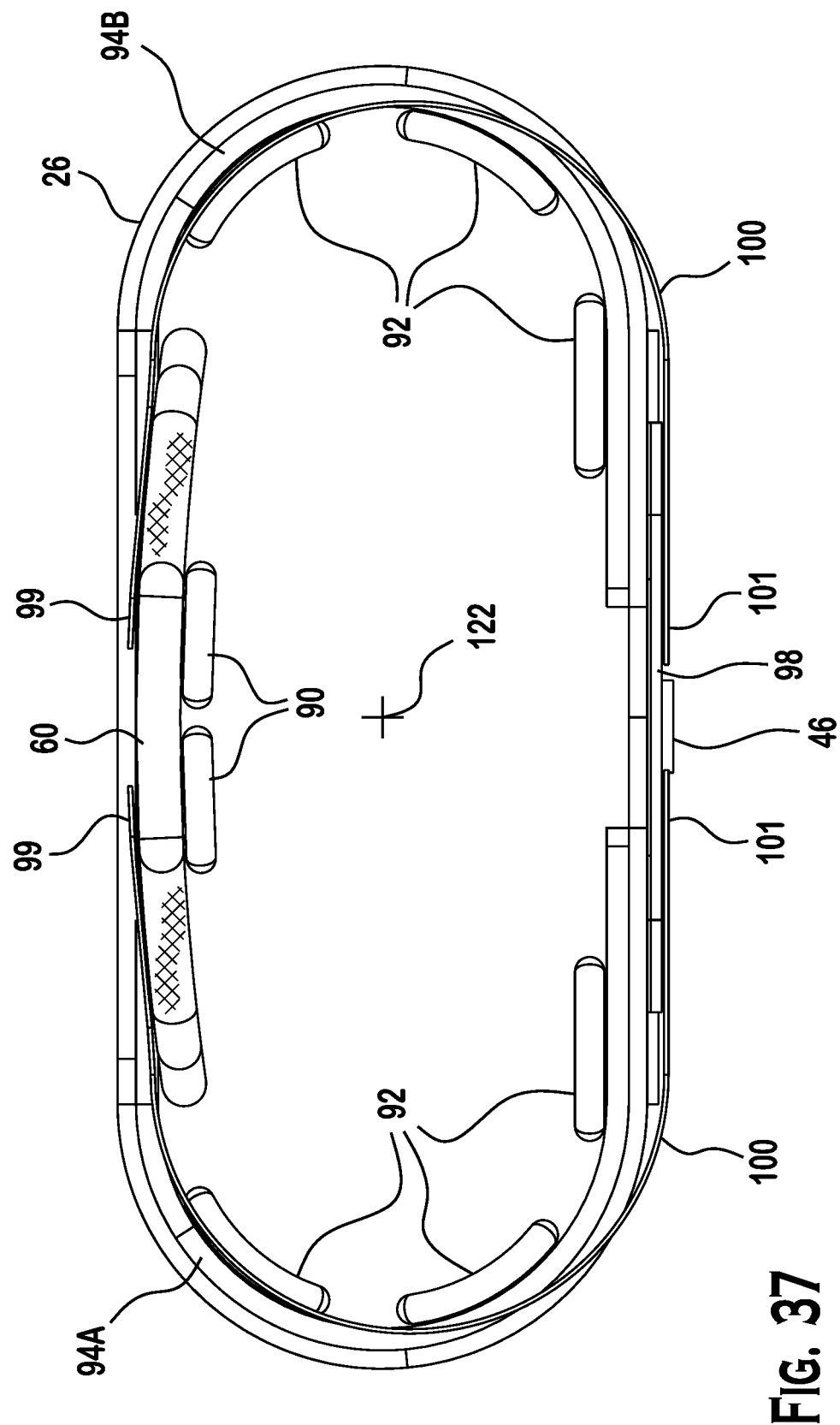
FIG. 37 is a top plan view of the body brace kit of FIG. 35. This more clearly shows the layering of the back-support members to the shell over the first and second torso wings which are attached to the brace body. This also shows the non-protruding side support members.
Figure 38:
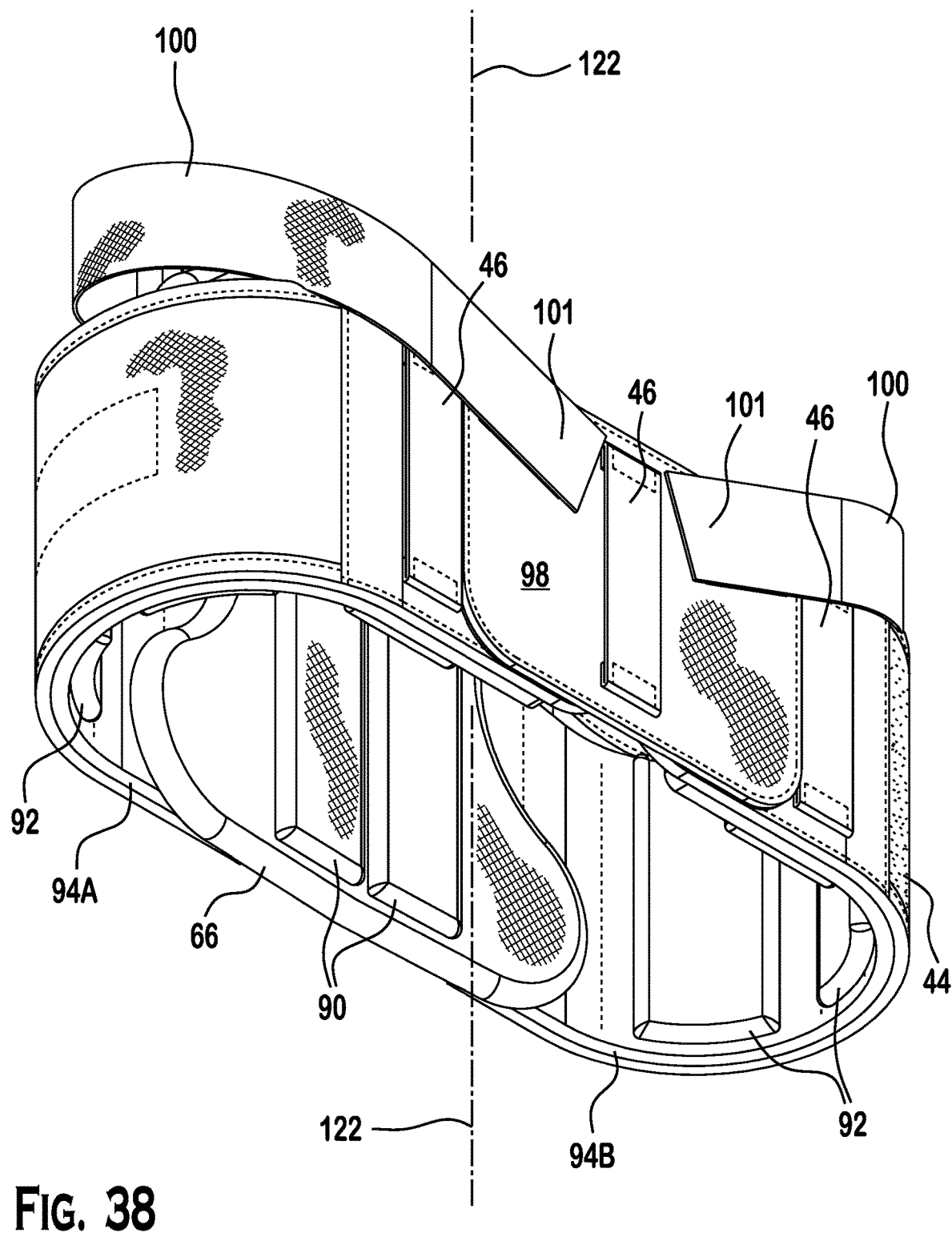
FIG. 38 is a front, bottom, left perspective view of the brace body kit of FIG. 35 illustrating the underarm straps attaching to the optional over abdomen connecting member which is shown with a hand loop.
Figure 39:
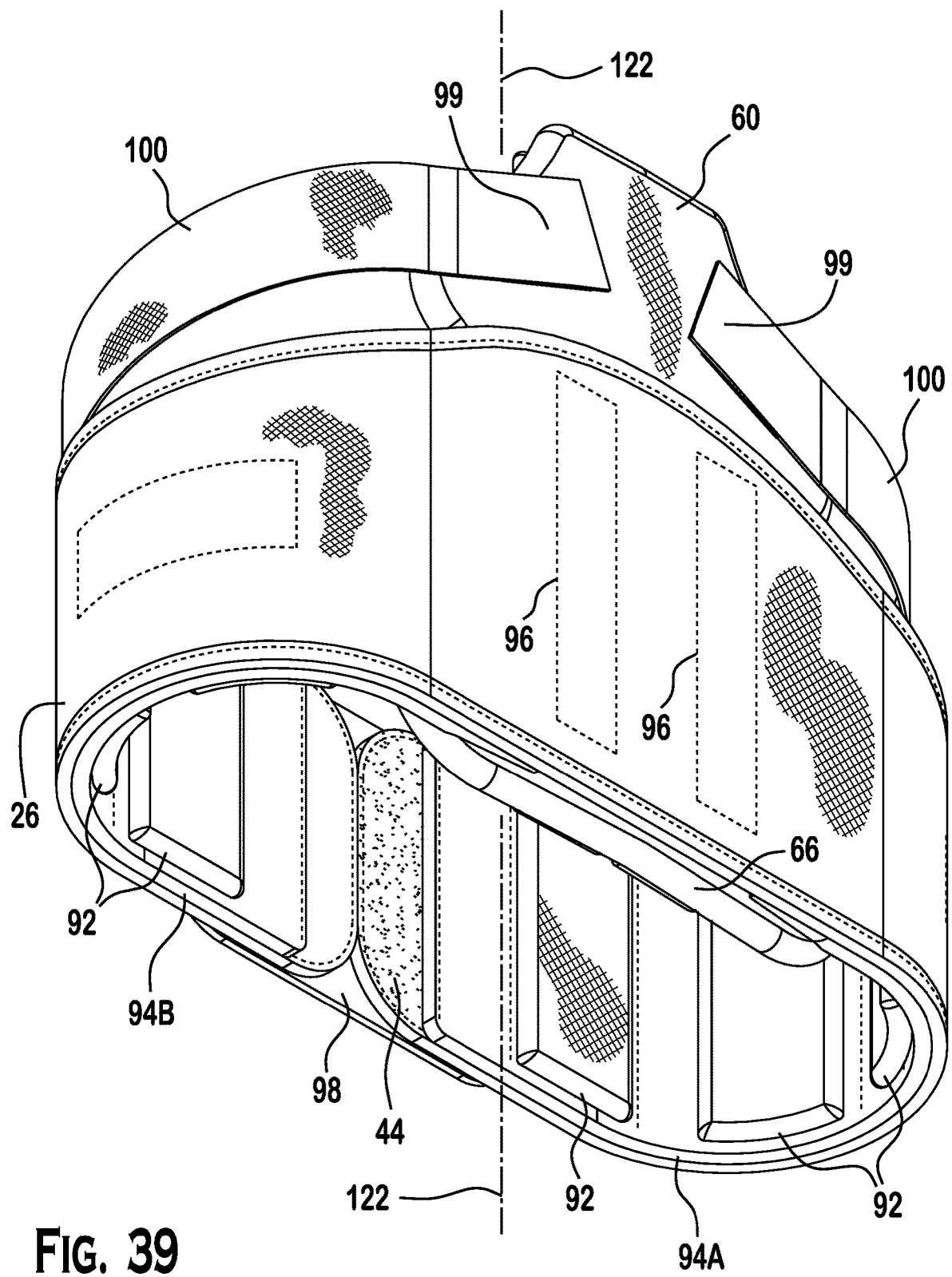
FIG. 39 is a rear, bottom, right perspective view of the body brace kit of FIG. 35 illustrating the need for the over abdomen connecting member by showing that the brace body ends preferably do not extend enough to overlap. The over abdomen extending member may only be necessary when the brace body is not wide enough to connect around the portion of the torso it is required to support.

Referring to FIGS. 14 and 18, the linkage block 42 preferably overlaps the seam between the first brace body 26 to the second brace body 28, such that the two may be secured. Any number of linkage blocks 42 may be provided, including as few as one and as many as ten or more. The linkage block 42 may be placed anywhere along the seam between the first brace body 26 to the second brace body 28, including taking the place of the first fastening element 36 and/or second fastening element 38. The former configuration may best been seen in FIG. 36. The linkage block 42 preferably includes hook-and-loop fastener 44 and raised edges 48. However, the linkage blocks 42 may include any suitable fastening element, such as magnets, snaps, buttons, and the like.

Referring again to FIG. 14, in one preferred embodiment the first brace body 26 may be detachably connected to the second brace body 28, with which it does not overlap, using at least one linkage block 42 and at least one support member 30, including the V-shape support members. In similar preferred embodiments, the first brace body 26 may comprise at least two support pockets 32, or V-shape support pockets 33*a* and 33*b*, and the second brace body 28 may comprise at least two guide pockets 34, the support members 30, or V-shape support members 31a and 31b, each being secured in one of the at least two support pockets and one of the at least two guide pockets. Through such a configuration, the V-shaped support members 31 may provide the desired configuration to both the first brace body 26 and the second brace body 28 while not being parallel to each other nor overlapping each other. Those of ordinary skill in the art will appreciate from this disclosure that the support members 30 and V-shape support members 31, and the support pockets 32 and V-shape support pockets 33, respectively, may be used interchangeably without exceeding the scope of this disclosure. Those of ordinary skill in the art will appreciate from this disclosure that any fastening means may be used in connection with any configuration of support members 30 (including V-shape support members 31) without exceeding the scope of this disclosure.

Figure 19:
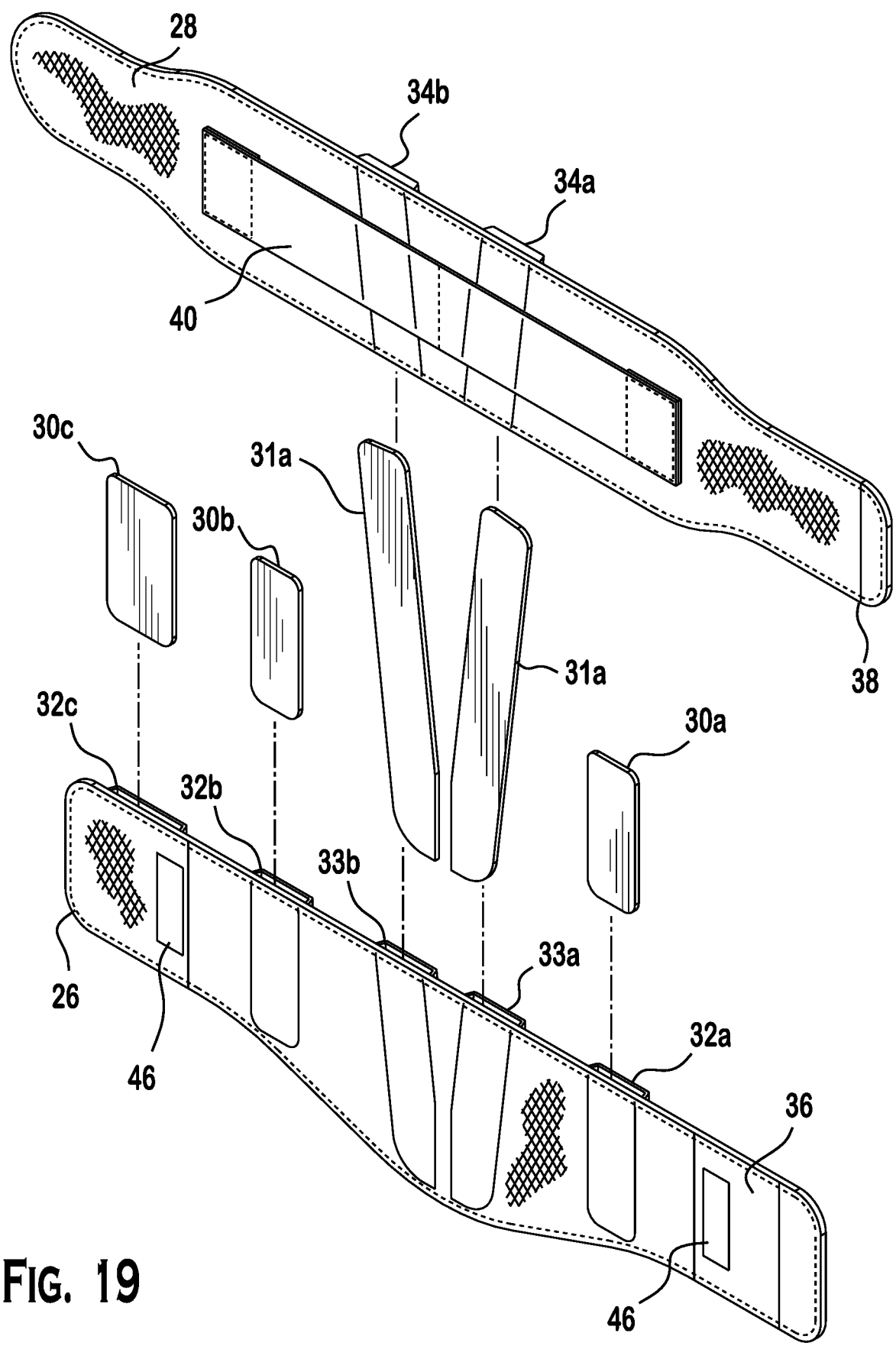
FIG. 19 is an exploded perspective view of an alternate embodiment of the body brace wherein the body brace includes three support pockets, two V-shape support pockets, two guide pockets, 2 V-shape support members, and three support members. In such an embodiment, support may be provided along the person's front in addition to person's sides and back.

Referring to FIG. 19, an alternate embodiment of the body brace 20 may include a first brace body 26 and a second brace body 28, with the first brace body 26 including five support pockets 32 therein. Two of the support pockets 32 may be V-shape support pockets 31a, 31b, being positioned on the first brace body 26 in minor-image angles from each other along a vertical axis 50 of the body brace 20. The body brace 20 may further include five support members 30, with two V-shape support members 33a, 33b being positionable in the V-shape support pockets 33. The third and fourth support pockets 32a, 32b may be positioned along separate lateral ends of the first brace body 26, with third and fourth support members 30a, 30b being removably positionable within the third and fourth support pockets 32a, 32b. The fifth support pocket 32c is preferably positioned at the furthest left lateral end of the first brace body 26 with the fifth support member 30c being positionable therein. Such an embodiment may provide additional support by positioning support members 31 along the person's front, sides, and back. Those of ordinary skill in the art will appreciate from this disclosure that the third, fourth, and fifth support pockets 32a, 32b, 32c may be positioned in any configuration along the first brace body 26, thus allowing the body brace 20 to cover different portions of the torso, without exceeding the scope of this disclosure. Those of ordinary skill in the art will further appreciate from this disclosure that any number of support pockets 32 and corresponding support members 31 may be provided without exceeding the scope of this disclosure.

In additional preferred embodiments, the first brace body 26 and second brace body 28 may be permanently affixed to one another. Suitable affixing means may include adhesive, meltable polymer, stitching, or any other means for permanently affixing two bodies. Such affixing means may also be present on one or more linkage blocks 42. Those of ordinary skill in the art will appreciate from this disclosure that the first brace body 26 may be permanently connected to the second brace body 28 using at least one linkage block 42 configured to include a permanent affixing means.

It is preferred that the support and guide pockets are formed, sewn, glued, or otherwise permanently attached to the first and second brace bodies. However, those of ordinary skill in the art will appreciate from this disclosure that the body brace may be configured to allow the support and guide pockets to be moveable without departing from the scope of the present invention. For example, the pockets could be temporarily positioned using a glue/wax/adhesive that could be removed by a solvent for repositioning. Additionally, the support and guide pockets could be connected via hook and loop material or other fastening means to allow removal and reattachment in different locations or to allow removal and replacement by differently sized pockets. This can allow the body brace to use support members having different thicknesses or sizes.

Figure 20:
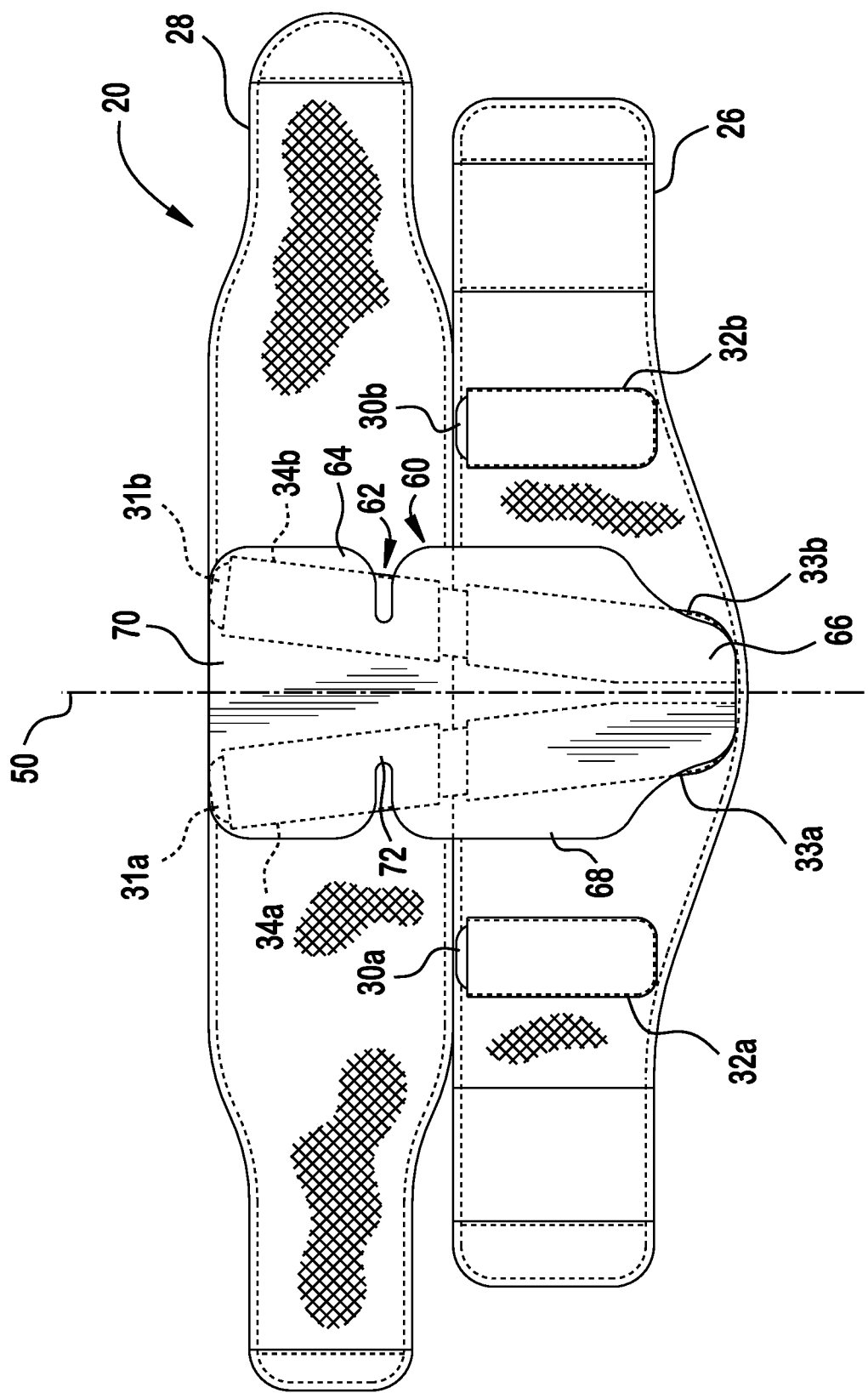
FIG. 20 is top elevational view of a body brace according to an alternate preferred embodiment of this invention. The figure shows that the body brace may include an outer shell which may overlay the outer surface of the brace body to provide additional support. The outer shell may have top and bottom portions which may be separated by a connecting region defined by a cutaway portion. The top portion may have an upper edge closest to the person's neck. The bottom portion may taper to define an apron portion, forming the preferred shape as shown and described. The outer shell may overlap support members, including the V-shape support members, along the back or sides of the body brace.

Referring to FIG. 20, some preferred embodiments of the body brace 20 may include an outer shell 60 which may cover at least a portion of the outer surface of the first body brace 26 and/or the second brace body 28. The outer shell 60 is preferably formed of a single sheet of rigid or semi-rigid plastic which may provide additional support for the torso 24 of a portion 22. However, those of ordinary skill in the art will appreciate from this disclosure that any suitably rigid or semi-rigid material, such as wood, metal, rubber, fiber glass, composite, or multiple sheets of plastic or any other suitable material may be provided without exceeding the scope of this disclosure. The outer shell 60 may be detachably affixed to the body brace 20 using hook-and-loop fastener, magnets, snaps, buttons, or any suitable affixing means, or may be permanently affixed to the body brace 20 using adhesive, stitching, or being sewn between the layers of the body brace 20. Alternatively, the outer shell 60 may be placed into a corresponding pocket (not picture) or may be affixed to the top of one or more support members 30 which may be positioned into one or more support pocket 32, including V-shape support members 31 inserted into V-shape support pockets 33. The outer shell 60 may overlay a portion of one or both of the first brace body 26 and second brace body 28, including the entire outer layer of the body brace 20.

The outer shell 60 may further include a top portion 64 and a bottom portion 68 which may be joined by a connecting region 72 defined by a cutaway portion 62. The top portion may further have an upper edge 70 which may run horizontally to provide additional support to the support members 30, particularly when overlaying the V-shape 52. The bottom portion 68 may taper to define an apron portion 66, with the sides thereof preferably forming diagonal lines to form a narrow bottom portion 68. Any or all of the outer shell 60 may be perforated to decrease weight and/or to increase flexibility. It is preferred that the outer shell 60 may overlay at least a portion of the body brace 20 along its vertical axis 50. However, those of ordinary skill in the art will appreciate from this disclosure that one or more outer shells 60 may be positioned or positionable over any portion of the body brace 20 or in any configuration without exceeding the scope of this disclosure.

In summary, to emphasize the medical effects and capabilities of the body brace 20 of the present invention, the support members 30 are preferably, but not necessarily formed using heatable and/or moldable semi-rigid or rigid orthoplastic struts or the like. Many of the remaining components of the body brace 20 are preferably formed of a neoprene/nylex shell, nylon, and hook-and-loop fastener straps and closures.

The body brace 20 is preferably formed of a flexible Postural Extension Truncal Orthosis which provides extension support with dual abdominal and thoraco-lumbosacral and coccygeal compression. The support provided by the body brace 20 may extend from the coccyx cephalad incorporating the sacrum, lumbar and thoracic spine to the scapular spine proper, which aids in the rotational control and postural extension through the rigid posterior panels.

The body brace 20 is preferably configured to allow control of protected motion while applying comfortable structural support for acute as well as chronic upper (thoracic) and lower (lumbar and sacral) back, thoracic, and spinal pain. Additionally, the body brace 20 may provide anterior/posterior support, and may be used to restrict and control rotation and side bending deformity in the saggital plane, which results from paraspinal spasm experienced due to nerve root compression, compression fractures, osteoporosis, disc desiccation as well as herniation, spinal stenosis, rib fractures, sternochondral/costochondral fracture-dislocations, scoliosis, excessive kyphosis and thoracolumbar musculoligamentous injury.

The preferred dual thoracolumbar compression provided by the first and second brace bodies 26, 28 along with the structural truncal postural extension allows increased intracavitary pressure unloading the vertical load on the intervertebral discs allowing relief from nerve root compression and foraminal narrowing.

The body brace 20 may be applied and/or customized by an orthopedic surgeon to help patients heal from back injuries without surgery and to help rehabilitate post-operative back patients to optimal health and lifestyle. The support members 30 are preferably heatable and moldable orthoplastic struts that can allow the body brace 20 to fit a person 22 closely while providing flexible yet rigid posterior thoraco-lumbar-sacral lumbar support. The support members 30 may provide direct sacral and lumbosacral support and then further rigid support from the sacrococcygeal junction through the thoracic spine, up to the scapular spine proper.

The body brace 20 may be configured to provide optimal trunk support, focusing support lateral to vertebrae, over the paraspinal musculature to allow optimal lateral support directly on the transverse processes as well as the large paraspinal muscles. This can allow a more comfortable and livable exoskeleton that takes the pressure off the spine directly while maintaining optimal alignment and resisting torque and compression on the discs proper.

By its preferred dynamic nature, even with possible rigid support of the entire spine the body brace 20 may allow gentle massaging action and passive heat to give further comfort and aids in healing the soft tissues surrounding the spine and discs proper or other affected body area.

With customizable rigidity due to the removable and customizable support members 30, the body brace 20 may produce abdominal intracavitary pressure to decrease the load on the spine, intervertebral discs and nerve roots. The preferred body brace 20 configuration may allow for the pressure on the upper torso thoracic and thoracolumbar portion to be adjusted according to chest contour and may still provide the necessary circumferential compression from coccyx and sacrum to thoracic spine as well as optimizing pressure according to the patient's desire and comfort.

The body brace 20 with first and second fastening elements 36, 38 (possibly formed via a hook-and-loop material forming an abdominal control frontal support piece) and lateral support accessory 40 (also referable to as an optional extension/reinforcing panel). Multiple support members 30 (possibly formed by heatable/moldable ortho-plastic struts) mau allow the rigid posterior panel support portion of the first and second brace bodies 26, 28 along with interior of the first and second brace bodies 26, 28 possibly including soft apron padding for semi-rigid/rigid anterior support, lateral and support members 30 allow further support as well as rotational control of the sacral, lumbar and thoracic spine and para-spinal musculature. The first brace body 26 and second brace body 28 may include soft inner interfaces and neoprene outer shells which may allow for the generation of heat with appropriate ventilation and firm, conforming support.

The first and second brace bodies 26, 28 may comprise adjustable outer shells to allow optimal conformity for individual chest and abdominal differences allowing an intimate fit to support abdomen, chest and thorax as well as the spinal column proper and the para-spinal musculature to address bony structural issues as well as muscular spasm and nerve root disc compression, fractures, dislocations and spinal stenosis.

Some, but not all, indications identifiable by physicians for use of the body brace 20 include but are not limited to: compression fractures of the thoracic and lumbar spine; transverse process and vertebral body fractures; thoracic and lumbar spine fractures, strain, or sprain; sacrum and coccygeal fractures and strains; sacrococcygeal ligament injury and fractures/dislocations; Ilipsoas strain; lumbago and lumbar back pain with lumbosacral instability; osteoporosis; thoracic kyphosis and scoliosis lumbar inter-segmental instability; spondylosis, spondylitis, and spondylolisthesis; post-operative lumbar and thoracic spine surgery; thoracic and lumbar disc herniation; spinal nerve root compression; thoracic and lumbar disc desiccation; spinal stenosis; rib fractures; sternochondral/costochondral ligament injury; fracture-dislocations costochondritis; thoracolumbar musculoligamentous injury; spinal fusion surgery; osteoarthritis and rheumatoid arthritis sacroiliitis; intractable back pain; metastatic spine lesions; spinal tumor stabilization osteomyelitis of the spine; and the like.

A variety of combinations/configurations of the body brace 20 may be used by removing or adding the support members 30 to produce the desired rigidity and immobilization as well as any modification in placement of the support members 30 throughout the course of the healing. The body brace 20 is preferably fully adjustable, allowing for reshaping, removing, adding, and/or changing the various components for maximum adaptation by the patient. The body brace 20 preferably provides rigid posterior support with flexible support offered through the inclusion of multiple support members 30.

The body brace 20 preferably supports both the thoracic and lumbosacral spine, but may also provide a unique, V-shaped support to the paraspinal musculature further limiting and balancing rotational deformity of the spine and thorax along with the rib cage. This can result in even greater comfort during healing from fractures and discogenic disease along with its associated muscle spasm.

The body brace 20 can preferably treat many orthopedic and neurological conditions associated with the sacrum, lumbar and thoracic spine. The body brace 20 may be designed to allow protected motion and or rigid immobilization. The orthosis may be physiologic, adaptable, dynamic and static and can be used to help correct multiple spine and back disorders and may be modified for a user's specific needs. This orthosis may also allow for the institution of dynamic protected motion which is especially helpful in the post-operative care of disc herniation and fracture stabilization surgery.

The support members 30 and body brace 20 can preferably be easily adjusted to the patient's wishes and condition, with progressive modifications being necessitated by treatment throughout the healing and treatment process. The body brace 20 can be specifically designed to immobilize the spine and thorax to a variety of positions and rigidities according to the nature of the injury and the stage the patient has reached in the healing process. This orthosis may be specifically designed to allow versatility not previously available for maximum adaptation to the patient for optimal control and comfort It should be noted that those of ordinary skill in the art will appreciate from this disclosure that the present invention may further be used in accordance with any medical device used for the support and/or immobilization of any body part without departing from the scope of the invention.

Referring to FIGS. 1-20, one preferred embodiment of the present invention operates as follows. A user places one or more support member 30 into the corresponding support pocket 32. The user then places the first brace body 26 along a portion of his or her torso 24 with interior of the first brace body 26 contacting the user's body. The user may then pull on the lateral ends of the first brace body 26 to allow the first fastening element 36 to connect along the user's front, detachably securing the first brace body 26 around the user's torso 24.

In a separate preferred embodiment, the user places one or more support member 30 into the corresponding support pocket 32. The user then places the second brace body 28 along the first brace body 26 such that the lower edge of the second brace body 28 abuts the upper edge of the first brace body 26 without overlapping it. In so doing, the user is careful to allow all support members to slide into any corresponding guide pocket 34. The user may then connect the first brace body 26 to the second brace body 26, if desired. It is preferred that the user connect the first brace body 26 to the second brace body 26 using a linkage block 42 or strap. However, those of ordinary skill in the art will appreciate from this disclosure that any suitable connecting means may be used without exceeding the scope of this disclosure. The user then places the body brace 20 along a portion of his or her torso with interiors of both the first brace body 26 and second body brace 28 contacting the user's body. The user may then pull on the lateral ends of the first brace body 26 and second brace body 28 to allow the first fastening element 36 to connect along the user's front and to allow the second fastening element 38 to connect along the user's front. This allows the user to detachably secure the body brace 20 around the user's torso 44.

In some preferred embodiments, prior to use of the body brace 20, the user may heat the support members 30 to induce a suitable heat-forming temperature. Once the support members 30 are heat-formable, the user may then place support members into the body brace 20 and secure the body brace 20 using the methods described above. Once in place, the support members 30 will contour to the shape of the person's torso 24 and solidify upon cooling, such that support of the torso 24 is provided in a customized and personalized manner.

Figure 34:
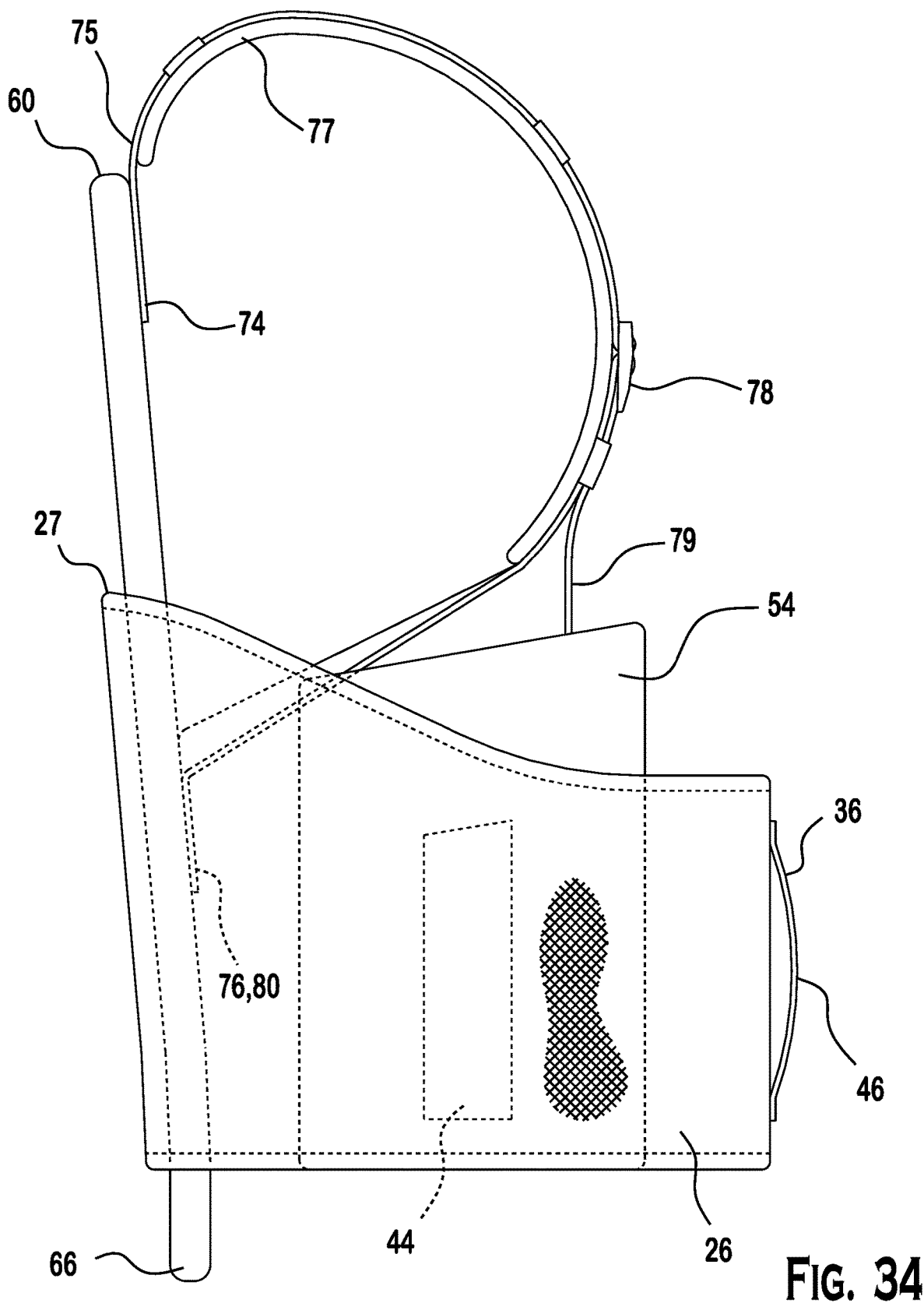
FIG. 34 is a side elevational view of the body brace of FIG. 30 positioned in a worn configuration.

Referring to FIG. 34, another embodiment of the present invention is directed to a body brace that is customizable for use in supporting at least a portion of a torso of a person. The body brace includes a shell 60 configured to maintain the person's torso in a contoured configuration and to provide resistance against bending the torso in a manner that does not conform with the contoured configuration.

Wherein the shell may include a flexible vertical rib 82 positioned generally along a longitudinal axis thereof such that left and right sides of the shell can fold with a hinge axis formed by the vertical rib and/or wherein the shell includes upper and lower portions which can twist relative to each other about the longitudinal axis.

The first brace body 26 is preferably configured to wrap around a portion of a torso of the person to provide support to the torso. The shell 60 is preferably positionable on the first brace body 26 and is configured to contact a greater portion (i.e., greater surface area) of a back of the person than the first brace body 26. The shell 60 is preferably configured to maintain the torso in a contoured configuration and to provide resistance against bending the torso in a manner that does not conform with the contoured configuration.

It is preferred, but not necessary, that the shell 60 can be adjusted via heating and cooling thereof to allow the support member to provide the contoured configuration customized for the person. For example, a patient can be laying down and the shell positioned over the patient's back after being heated such that the shell 60 can be adjusted for any particular medical conditions of the patient. Then, the shell 60 can be allowed to cool and retainer the customized, adjusted, contoured configuration.

Referring to FIGS. 30-34, a plurality of shoulder straps 75 may be positioned on the shell 60 and/or the body brace 26 such that the first brace body 26 encircles a waist of the person while also being supported on at least one shoulder 25 of the person. The shoulder straps 75 may include padding 77 and may also include strap adjustment mechanisms 78.

It is preferred, but not necessary that a first end 74 of the straps 75 is connected to an upper portion of the shell 60 and that a lower end 76 of the straps 75 is connected to a lower portion of the shell 60. Any excess straps 79 can be tucked inside of the first brace body 26 and snuggly positioned against the torso of the person.

The shell 60 and side supports 54 can include an extra outer layer of hardened material such as thin metal or hardened plastic or composite to act as a protective shell in the event of a person being struck during day to day activities by people or objects. It is preferred that the first brace body 26 is detachably connected to the shell 60 via snaps, buttons, adhesive, hook and loop material, magnets, or the like.

Figure 22:
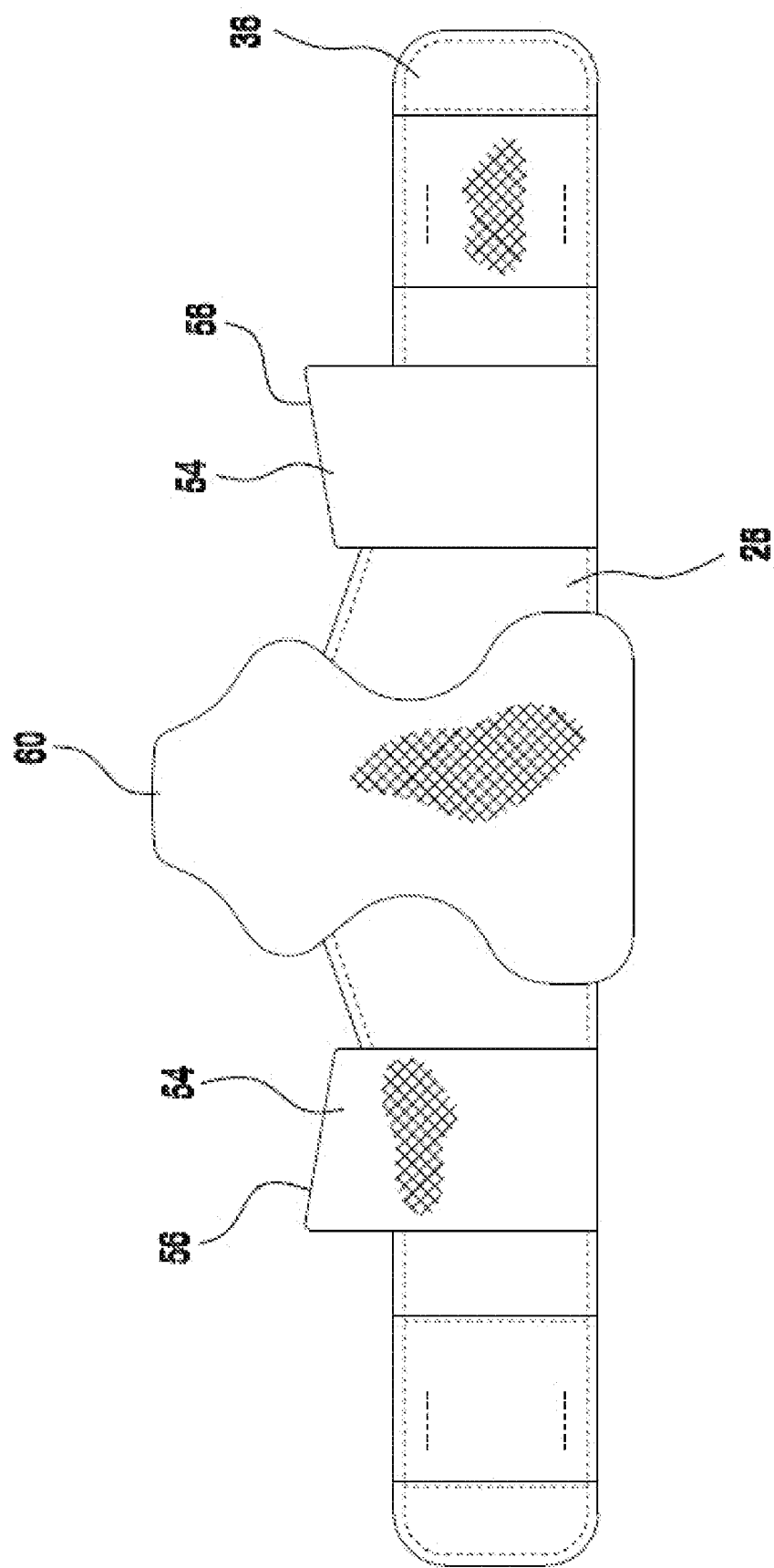
FIG. 22 is directed to a front elevational view of the body brace of FIG. 21 and more clearly illustrates a preferred configuration of the side supports and the shell. It is preferred, but not necessary, that the side supports have a generally trapezoidal shape with an upper edge that is beveled (or angled) so as to decrease in height as one moves generally rearwardly along the side of a person's body after the first brace support is in position on the person. This preferably helps support the body and maintain good posture and prevents leaning forward too much. The shell preferably has a narrow rounded upper edge that scallops down to a widened wing section which may overlay portions of a person's upper back/shoulder blades and then has a connecting region which necks inwardly in an hourglass fashion before expanding again outwardly to form an apron section (or lower section) of the shell.
Figure 23:
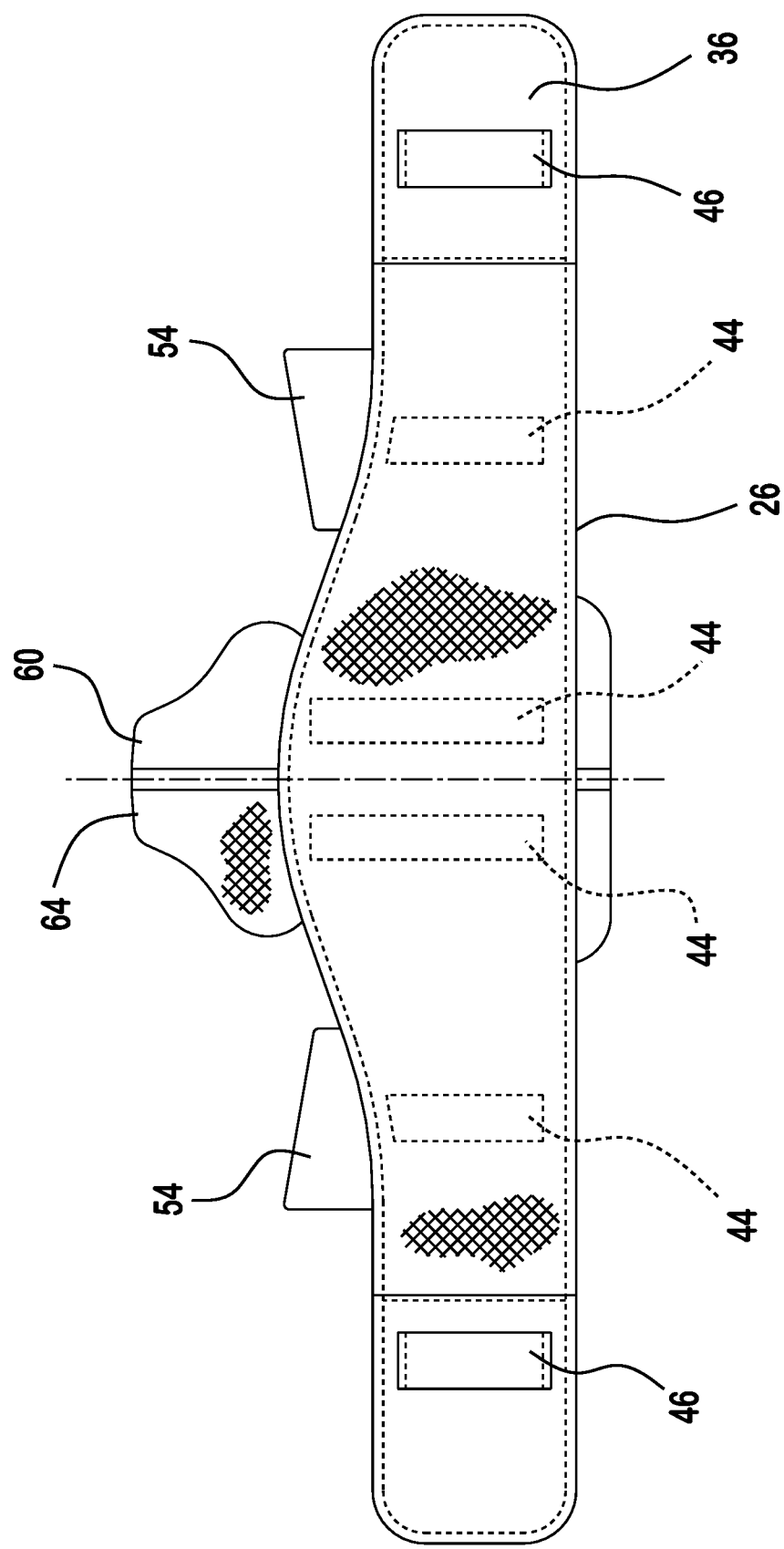
FIG. 23 is a rear elevational view of the body brace of FIG. 21 modified to include a vertical rib which is positioned centrally along a vertical axis of the shell. This provides some flexibility and further allows the shell to be wrapped around a person's body with increased comfort. The vertical rib preferably divides the shell into two symmetrical halves (or wing portions). The vertical rib can be formed of elastomer, ribbed/corrugated plastic, fabric, neoprene or the like. Alternatively, the shell can be custom adjusted and curved to precisely fit a person's back. This can be done by heating the shell, placing the shell along a person's back, and molding the shell and allowing it to cool once the configuration is determined.
Figure 24:
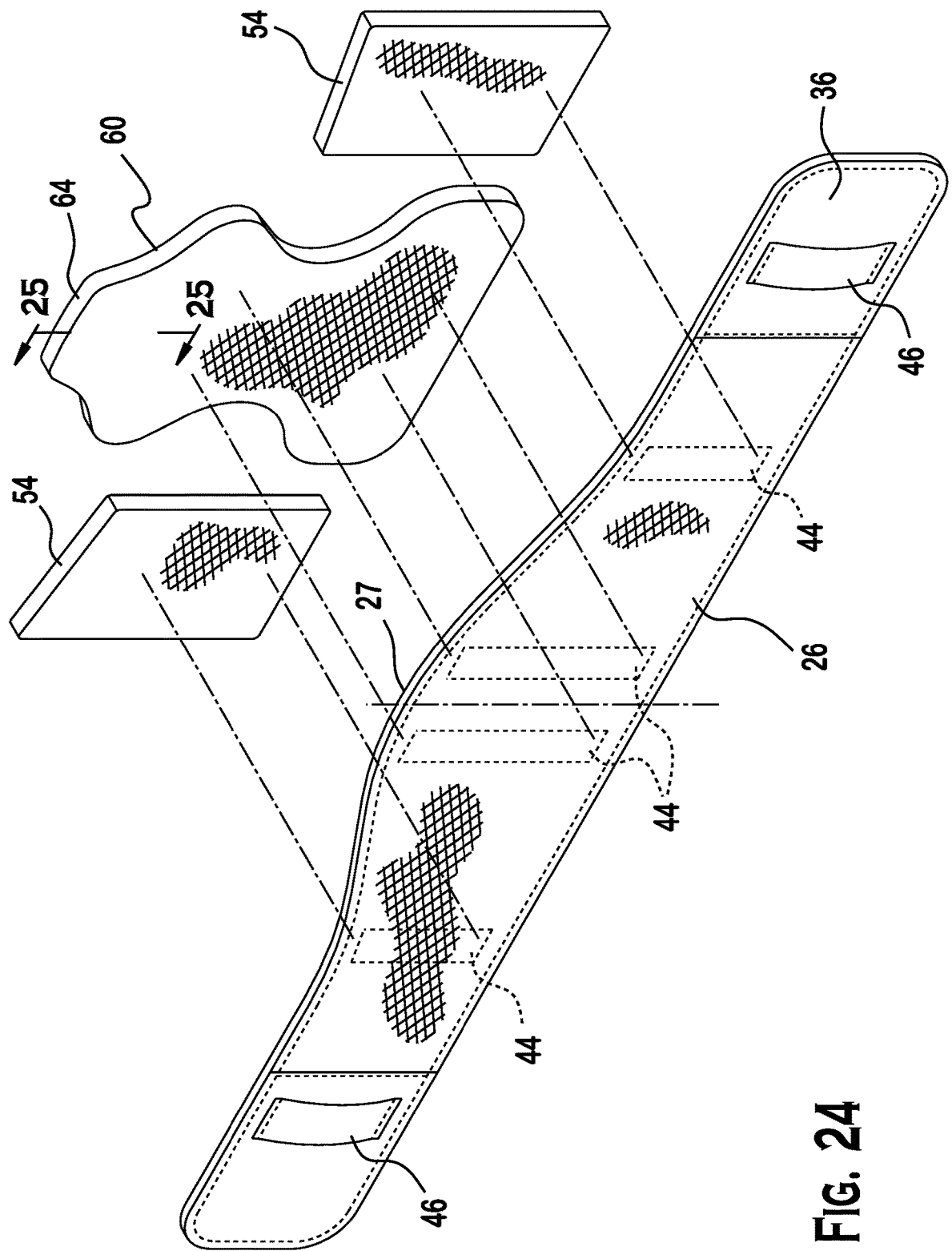
FIG. 24 is an exploded perspective view of the body brace of FIG. 21 illustrating the preferred attachment of the shell and the side supports to the first brace body in a detachable fashion using hook and loop material.
Figure 32:
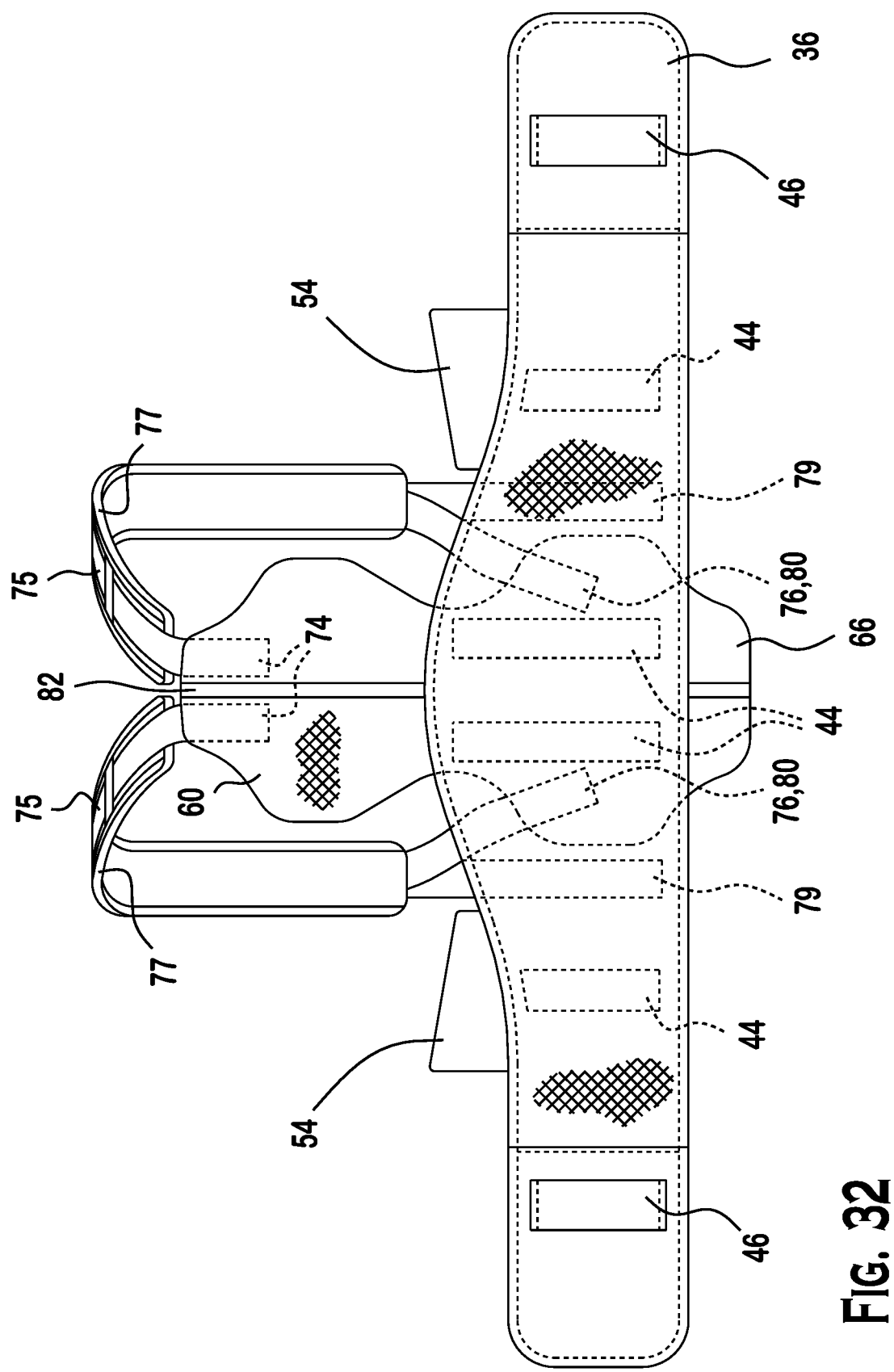
FIG. 32 is a rear elevational view of the body brace of FIG. 30.
Figure 33:
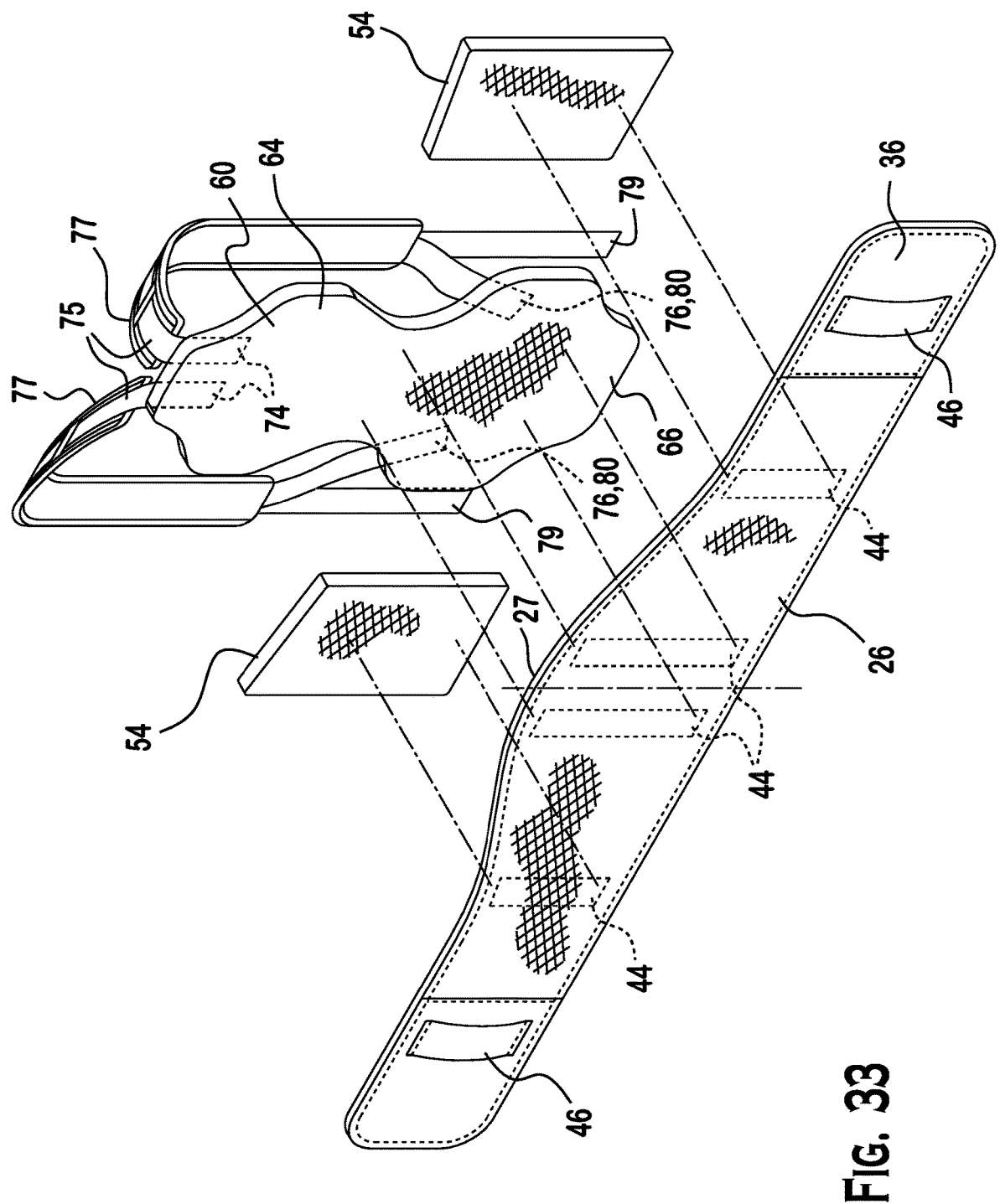
FIG. 33 is an exploded view of the body brace of FIG. 30.

Referring to FIGS. 22 and 32, the shell 60 may have an arcuate upper edge 64 and an arcuate lower edge 68. The arcuate upper edge 64 can be shorter than the arcuate lower edge 68.

It is preferably that the lateral width of the shell increases, then decreases, then increases again as one moves from the arcuate upper edge to the arcuate lower edge such that each laterally facing side of the shell generally has a sideways W-shape. This preferred configuration may provide support at the person's shoulder blades and hips while allowing relative twisting motion therebetween about a longitudinal axis of the shell 60. The sideways W-shape preferably results in the shell 60 having two laterally wide sections positioned vertically one over the other and connected by a narrow lateral section to allow relative twisting therebetween. This preferred hourglass shape can enhance comfort and long term wearability of the body brace.

Figure 21:
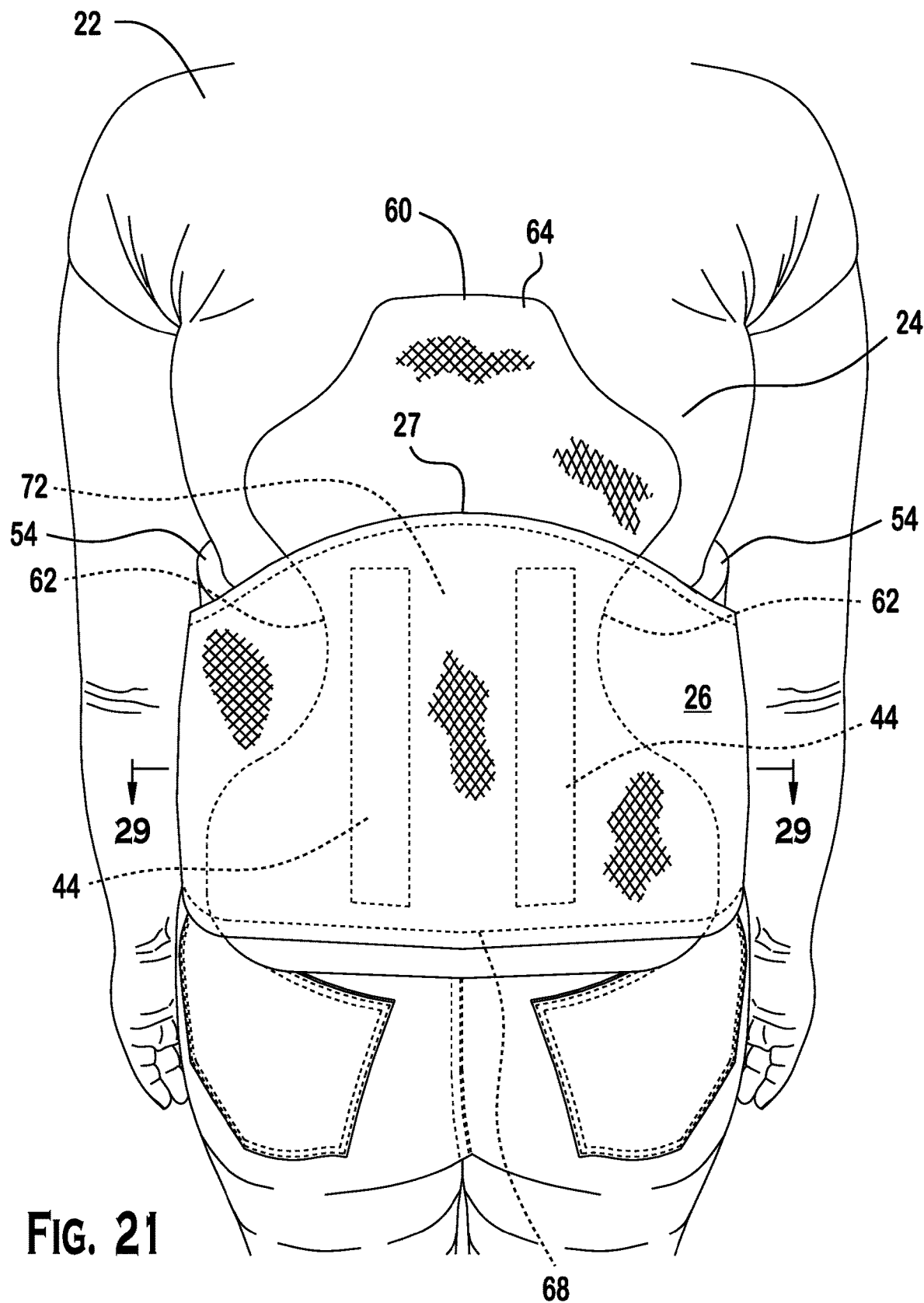
FIG. 21 is a rear perspective view of a preferred second embodiment of the body brace according to the present invention. The body brace is shown being worn by a person on a portion of the person's torso. Those of ordinary skill in the art will appreciate from this disclosure, however, that the body brace may be worn differently and over different parts of the torso by different users, such as being worn as low as the hips and as high as the shoulders, without departing from the scope of the present invention. A shell is preferably positioned between the first brace body and the person. The shell may be attached via hook and loop material to the first brace body to provide optimum support to the back. Additionally, side supports may be positioned between or above a user's waist and the first brace body. It is preferred, but not necessary, that the side supports and the shell are detachably affixed to the first brace body via any suitable attachment mechanism, such as hook and loop material. Alternatively, the shell and side supports can be fixed or permanently attached to the first brace body without departing from the scope of the present invention. It is preferred that the shell extend vertically above an upper edge of the first brace body and extend vertically below a lower edge of the first brace body.

Referring to FIG. 21 the body brace according to the present invention is shown being worn by a person 22 on a portion of the person's torso 24. Those of ordinary skill in the art will appreciate from this disclosure, however, that the body brace may be worn differently and over different parts of the torso by different users, such as being worn as low as the hips and as high as the shoulders, without departing from the scope of the invention. A shell 60 is preferably positioned between the first brace body 26 and the person 22.

The shell may be attached via hook and loop material 44 to the first brace body 26 to provide optimum support to the back of the person. Additionally, side supports 54 may be positioned between or above a person's 22 waist and the first brace body 26. It is preferred, but not necessary that the side supports 54 and the shell 60 are detachably affixed to the first brace body 26 via any suitable attachment mechanism, such as hook and loop material.

Alternatively, the shell 60 and side supports 54 can be fixed or permanently attached to the first brace body 26 without departing from the scope of the present invention. It is preferred, but not necessary, that the shell 60 extend vertically above and upper edge 27 of the first brace body 26 and extend vertically below a lower edge of the first brace body 26. The upper edge preferably forms a gentle convex arc that narrows in width as one moves vertically up along the longitudinal axis of the shell 60.

Referring to FIGS. 22-24, 28, and 29, the side supports 54 are preferably trapezoidal in shape. It is preferred, but not necessary, that the side supports have a generally trapezoidal shape with an upper edge that is beveled (or angled) so as to decrease in height as one moves generally rearwardly along a body after the first brace support is in position. This is preferably to help support the body in maintaining good posture and not leaning forward too much. The shell preferably has an narrow rounded upper edge that scallops down to a wide wing section which may overlay portions of a person's upper back and then has a narrowed connecting region 72 which necks inwardly in an hourglass fashion before expanding again outwardly to form an apron section (or lower section) of the shell.

The body brace may use a shell 60 having a vertical rib which is positioned centrally along a vertical axis (or central longitudinal axis) of the shell 60. This provides some flexibility and further allows the shell 60 to fold in addition to flexing so as to be wrapped around a person's body with increased comfort. The vertical rib preferably divides the shell 60 into two symmetrical wing portions (or halves). Alternatively, the shell 60 can be custom adjusted and curved to precisely fit a person's back. This can be done by heating the shell, placing the shell along a person's back, and molding the shell 60 and then allowing it to cool in position.

Figure 25:
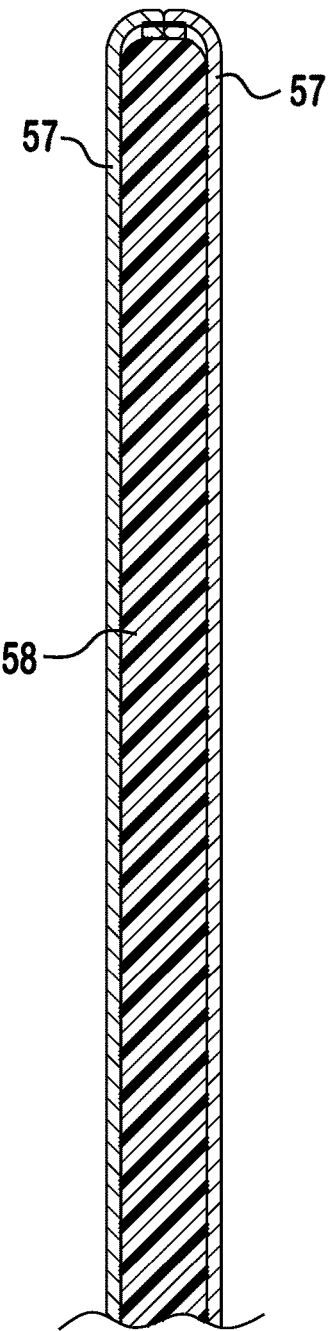
FIG. 25 is a partial cross-sectional view of the shell of FIG. 24 as taken along the lines 25-25 of FIG. 24 illustrating one preferred construction of the shell which includes a plastic and/or polymer core with a fabric, neoprene, or synthetic cover thereover.
Figure 26:
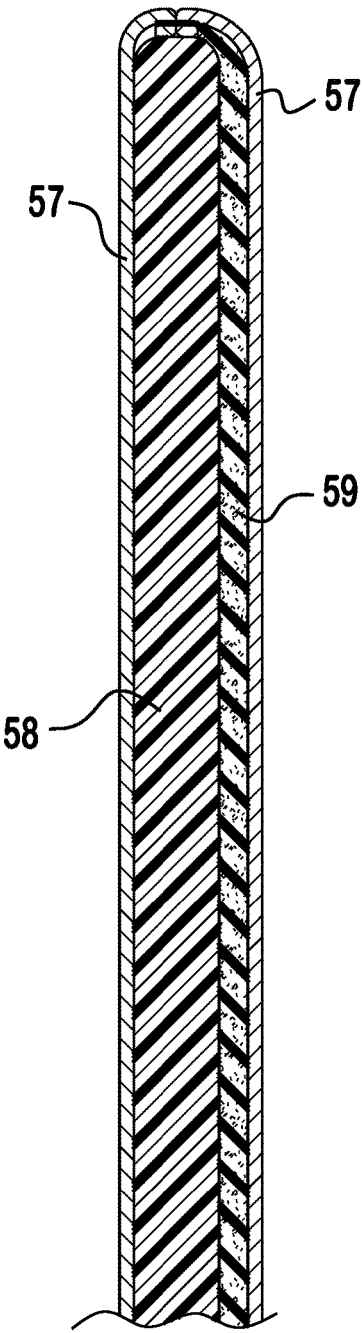
FIG. 26 is a partial cross-sectional view of the shell of FIG. 24 similar to that of FIG. 25 illustrating that the shell may be constructed to include padding and/or foam or the like therein. The padding is shown along a single surface of the shell.
Figure 27:
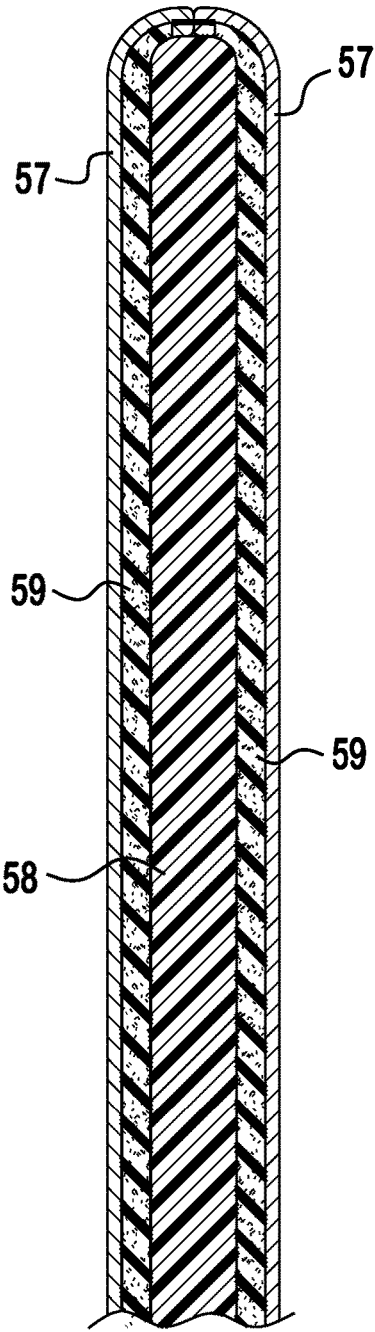
FIG. 27 is a partial cross-sectional view of the shell of FIG. 24 similar to that of FIG. 25 illustrating that the shell may be constructed to include padding and/or foam or the like along both major surfaces of the central plastic/polymer core. Although three preferred constructions of the shell have been shown, those of ordinary skill in the art will appreciate from this disclosure that any suitable construction can be used for the shell without departing from the scope of the present invention.
Figure 28:
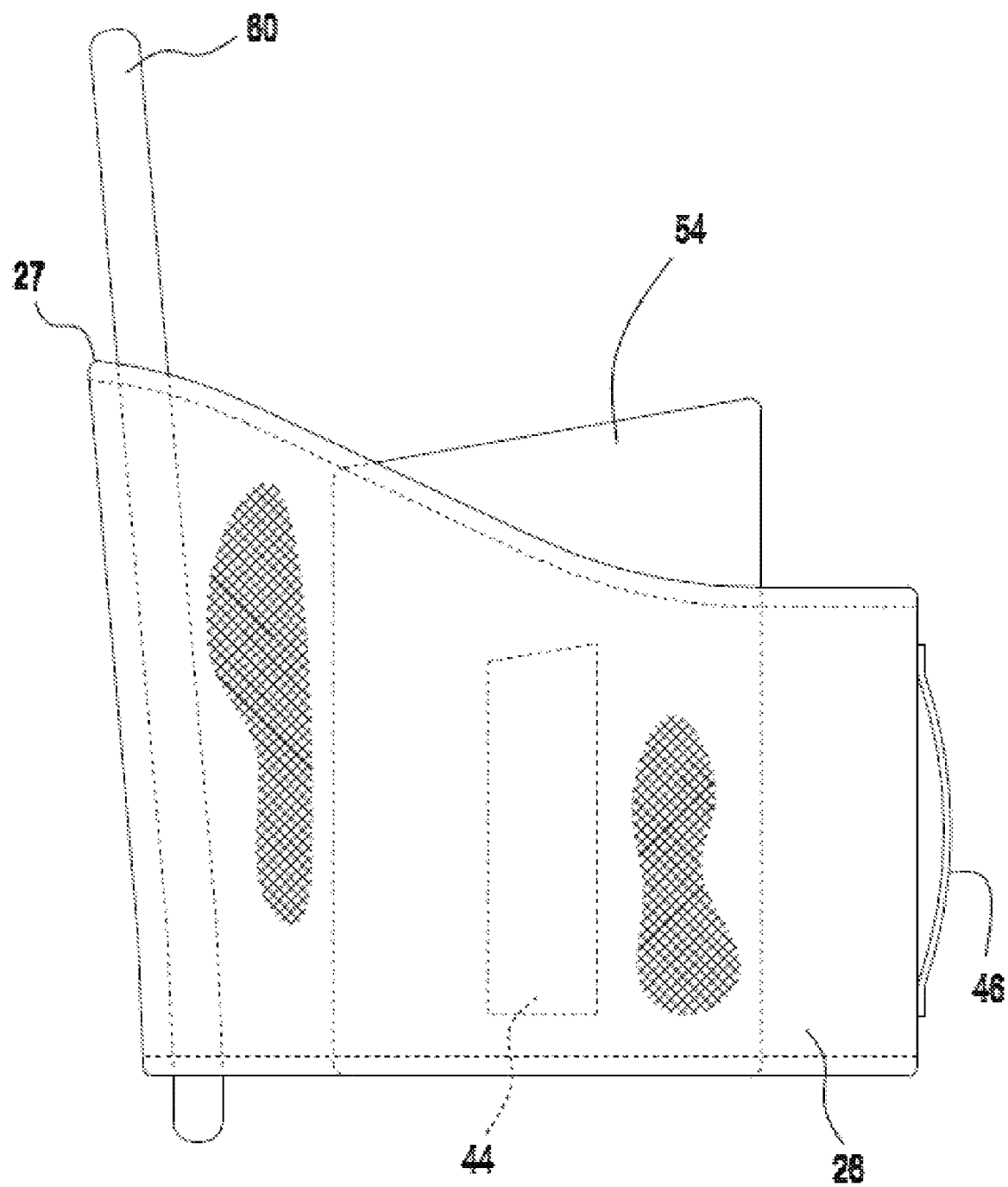
FIG. 28 is a left side elevational view of the body brace of FIG. 21 configured in the wrapped position similar to that in which it is positioned when encircling a person.
Figure 29:
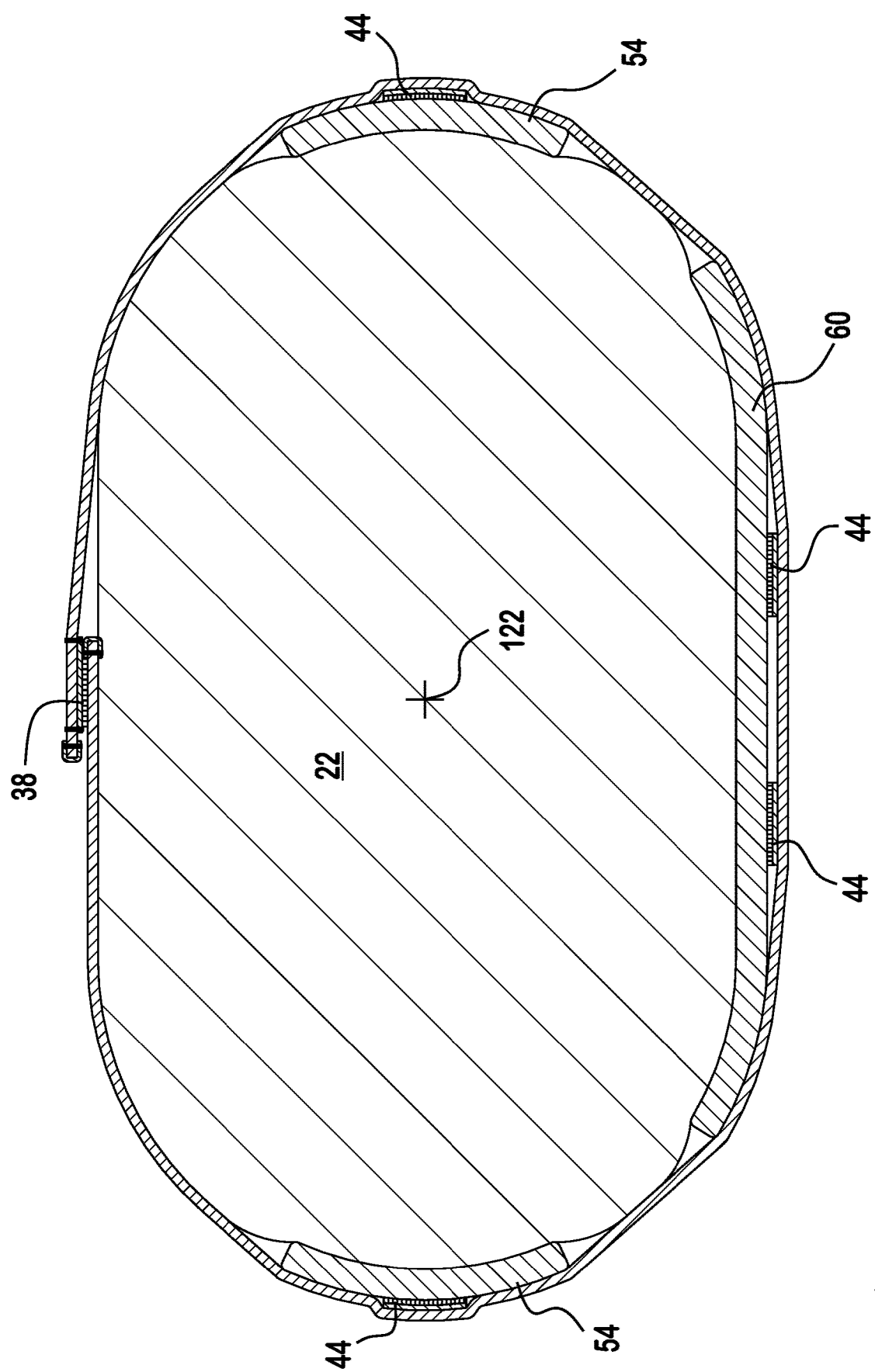
FIG. 29 is a cross-sectional view through the body brace of FIG. 21 taken laterally which illustrates Velcro attachments for the shell and the side supports as well as the front straps of the first brace body.
Figure 30:
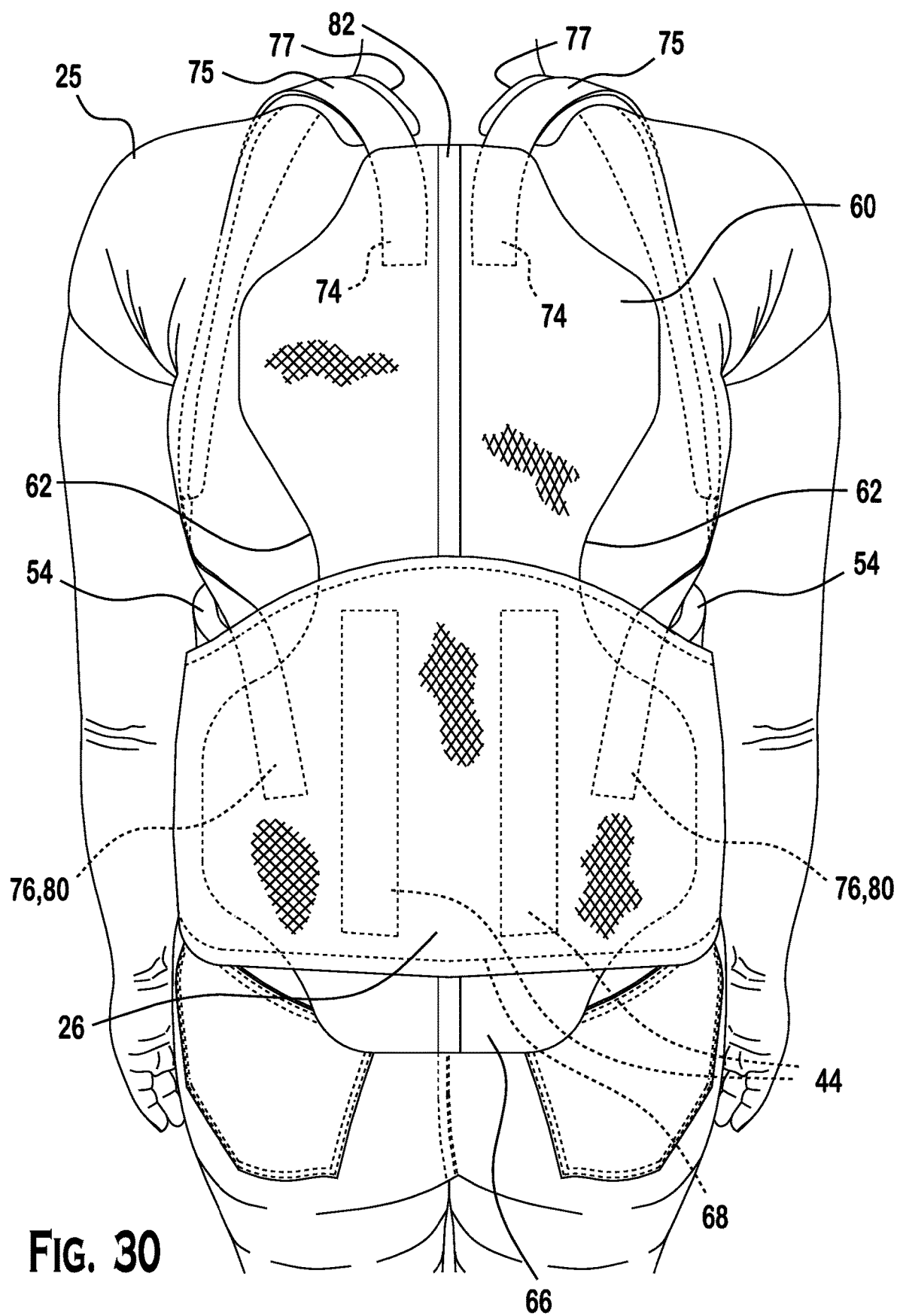
FIG. 30 is a rear perspective view of the body brace of FIG. 21 with shoulder straps attached thereto. The shoulder straps may include padding and can be permanently and/or detachably affixed to any combination of the shell and/or the first brace body.
Figure 31:
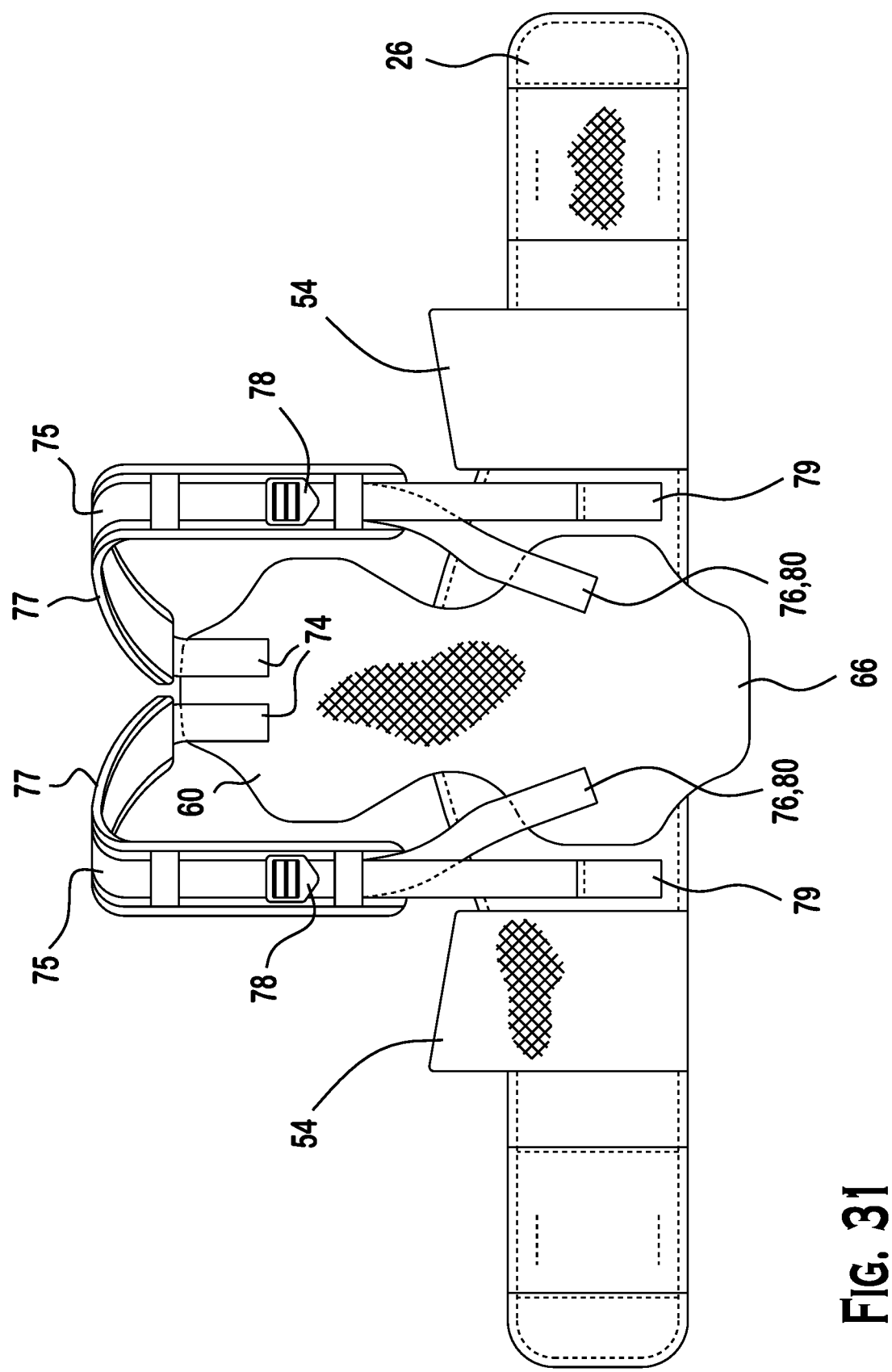
FIG. 31 is a front elevational view of the body brace of FIG. 30 illustrating excess shoulder strap material which may dangle in front as a result of the positioning of the strap adjustments.

It is preferred, but not necessary, that the shell 60 and the side supports 54 are positioned on the first brace body 26 in a detachable fashion using hook and loop material 44. Referring to FIG. 25 the shell may comprise a polymer/plastic and/or composite core 58 with a fabric, neoprene, or synthetic cover 57 thereover. Referring to FIG. 26, the shell 60 may be constructed to include padding and/or foam 59 or the like therein. The padding 59 is shown along a single surface of the shell. Referring to FIG. 27, the shell 60 may be constructed to include padding and/or foam 59 or the like along both major surfaces of the central plastic/polymer core 58. Although three preferred constructions of the shell 60 have been shown, those of ordinary skill in the art will appreciate from this disclosure that any suitable construction can be used for the shell without departing from the scope of the present invention.

Referring to FIGS. 30-34, the body brace 60 may include shoulder straps 75 attached thereto. The shoulder straps may include padding 77 and can be permanently and/or detachably affixed to any combination of the shell 60 and/or the first brace body 26. Excess shoulder strap material 79 may dangle in front as a result of the positioning of the strap adjustments 78.

Figure 35:
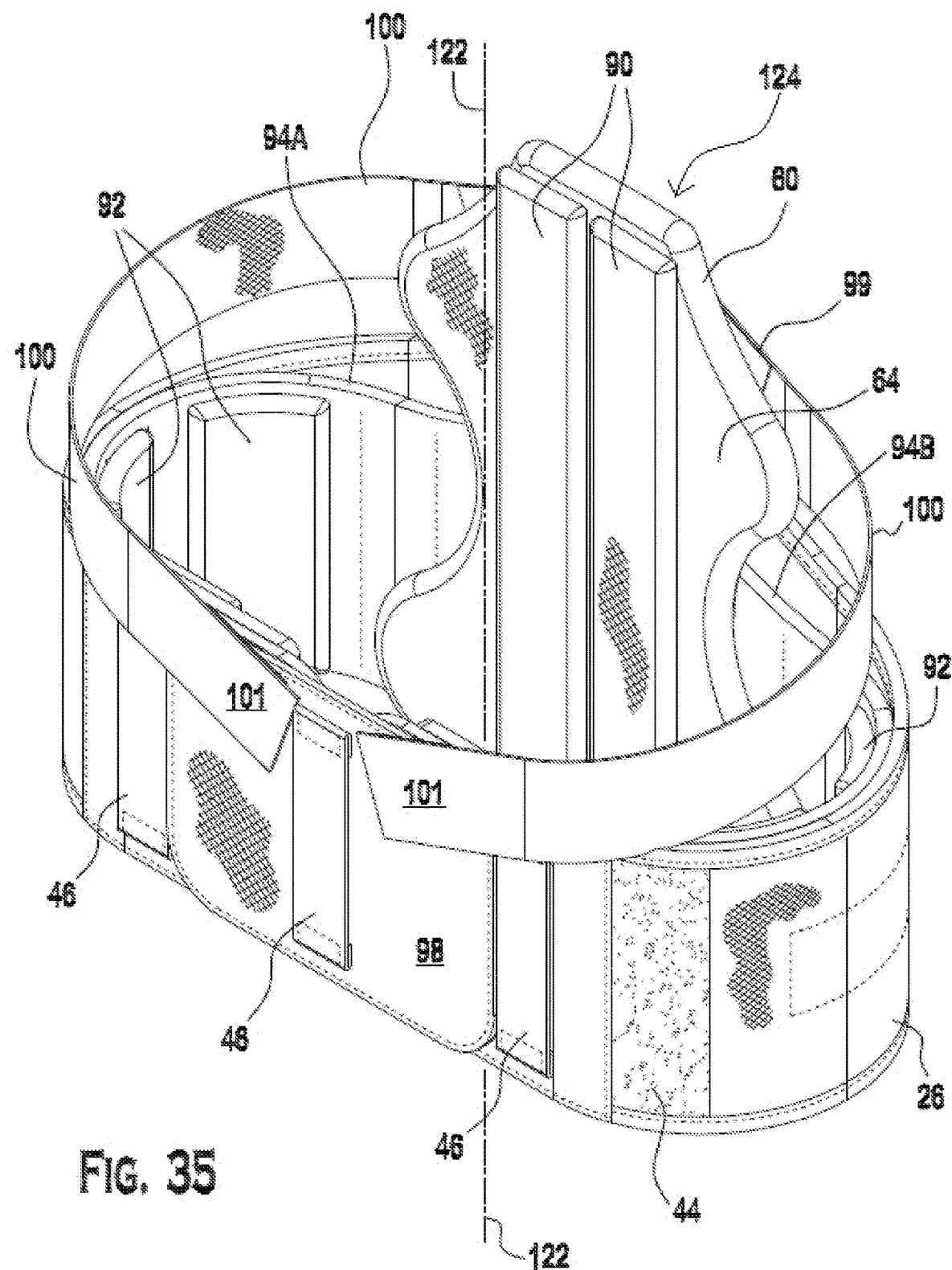
FIG. 35 is a front, top, right, perspective view of a splint according to a first preferred embodiment of a body brace kit that is customizable by the user. Each kit 124 preferably, but not necessarily comes with at least three components. Those of ordinary skill in the art will appreciate from this disclosure that a two piece kit or a single piece adjustable kit can be provided without departing from the scope of the present invention. The first component is preferably a brace body 26. The preferred embodiment of FIG. 35 includes detachable first and second torso support wings attached to the interior face of the brace body with non-protruding side supports attached to the interior of the toro wings on either side so the side supports will contact the torso near the hips of the user. On the exterior face of the brace body there can be an over abdomen connecting member attached to the ends that increases the circumference of the body brace. Hand loops can be provided to assist the user while tightening the brace. Additionally, there may be a shell attached to the interior face of the first and second torso support wings on the outer face which could also have back support members attached on its interior face so that the back support members will contact the back of the torso. An underarm strap can, but is not necessarily, be provided that connects the shell to the over abdomen connecting member.

Unless otherwise described below, one of ordinary skill in the art will appreciate from this disclosure that the components of the kit are generally made of similar material and/or are used in a similar fashion to similar components (even if of other types) mentioned above. Referring to FIG. 35, another embodiment of the present invention is directed to a body brace kit 124 that is completely customizable for use in supporting at least a portion of a torso of a person. Each kit 124 may be individually customizable and preferably, but not necessarily, comes with at least three components. The first component that may come with each kit is the first brace body 26. The other two components of the at least three components that may comprise the kit 124 include: a first torso support wing 94a and a second torso support wing 94b, a lower back support pad 96, a side support member 54, a non-protruding side support member 92, a shell 60, a back support member 90, and/or a chest support member 104.

While each kit 124 is preferably customizable with at least three components, those components may consist of multiples of the same type. For instance, the body brace kit 124 may be comprised of the first brace body 26, and two lower back support pads 96. The first torso wing 94a and the second torso wing 94b are each a component. Thus, a customizable kit 124 may only consist of a first brace body 26 and a first 94a and second 94b torso wing. While each kit preferably, but not necessarily, consists of three elements (or fewer) the components may be combined in any way to suit the specific needs of an individual. For instance, a kit 124 may consist of a brace body 26, a first torso wing 94a, two side support members 54, and a chest support member 104. Those of ordinary skill in the art will appreciate from this disclosure that any combination of element can be used to form a body brace 20 without departing from the scope of the present invention. It is preferred, but not necessary, that the additional components are formed of heat moldable, re-heatable, re-configurable material wrapped in a preferably soft cover which may include padding therein.

Each of the brace body kits 124 may include a first brace body 26 which may fasten about the wearer's front using a first fastening element 36. Preferably, the first and second fastening elements 36 are formed of hook-and-loop material, such as VELCRO®-brand hook-and-loop fastener. However, those of ordinary skill in the art will appreciate from this disclosure that the fastening elements 36 may be formed of any suitable fastening, means such as buttons, snaps, zippers, magnets, and more without exceeding the scope of this disclosure. The brace body 26 may additionally include an abdomen connecting member 98 to extend the length of the band to adjust to cover a larger circumference.

The first brace body 26 may additionally have a hand loop 46 on the outer face of the front side of the brace body. The hand loop provides the user a means to fasten the fastening elements 36 on the ends of the brace body 26 more tightly when securing the brace around the torso. The hand loop may appear on any embodiment that has a brace body 26 and is not limited to the kits 124. The hand loop 46 is not necessarily, but may be, considered one of the elements which make up a kit 124. The hand loops may be detachably fastened to the brace body via hook-and-loop material or the like.

Figure 42:
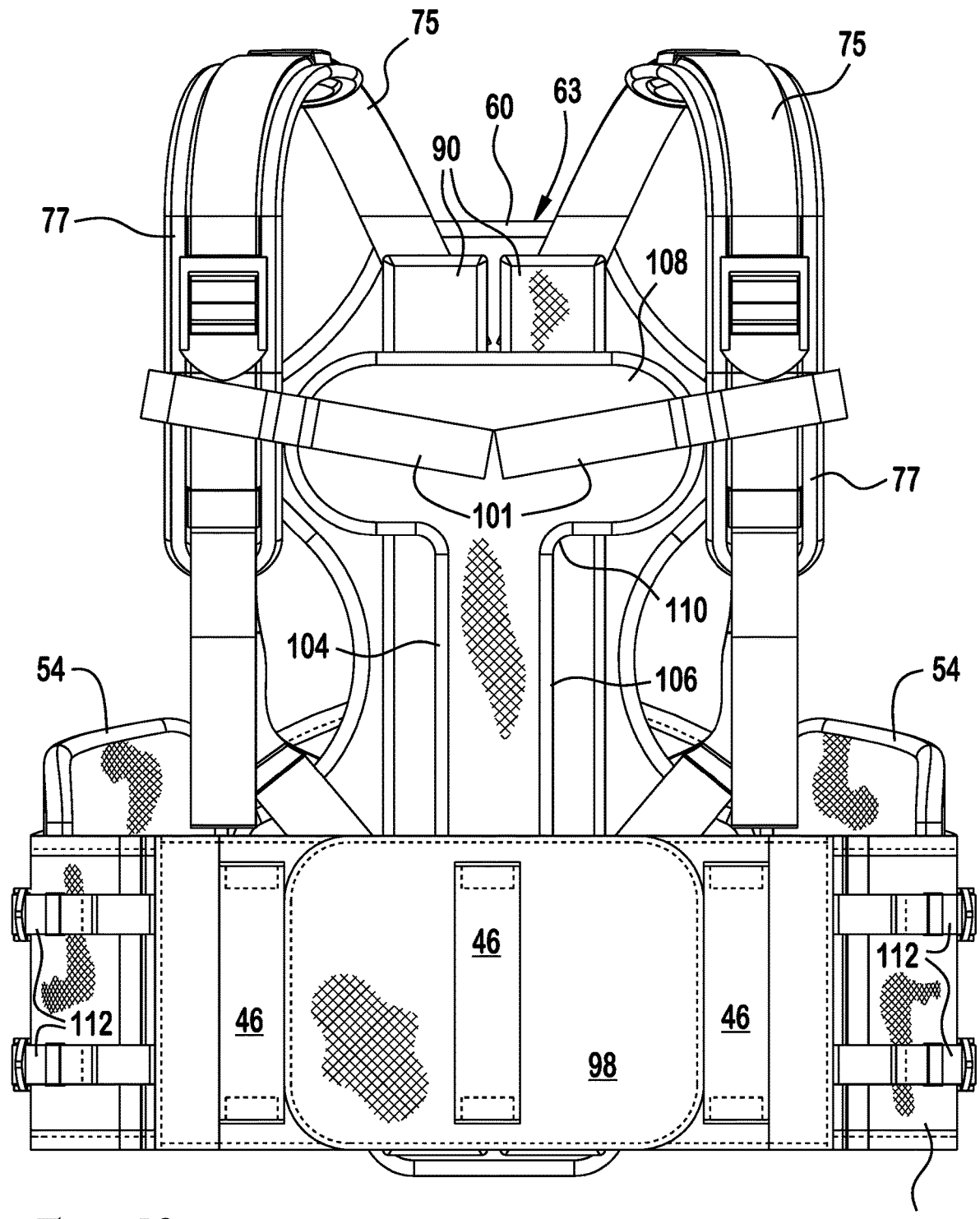
FIG. 42 is a third preferred embodiment of the body brace kit comprising a brace body, two side supports, a chest support and a shell. The shell is connected to the chest support member via shoulder and underarm straps. The brace body has side supports attached to both sides on its inside face and an over abdomen connecting member attached to the two ends for extra circumferential extension. Additionally, there are hand loops on the brace body on either side of the abdomen connecting member and a hand loop centrally located on the over abdomen connecting member. For similar purposes as the hand loops, there are side buckles on the outside of the brace body for the user to tighten the body and further restrict motion.
Figure 43:
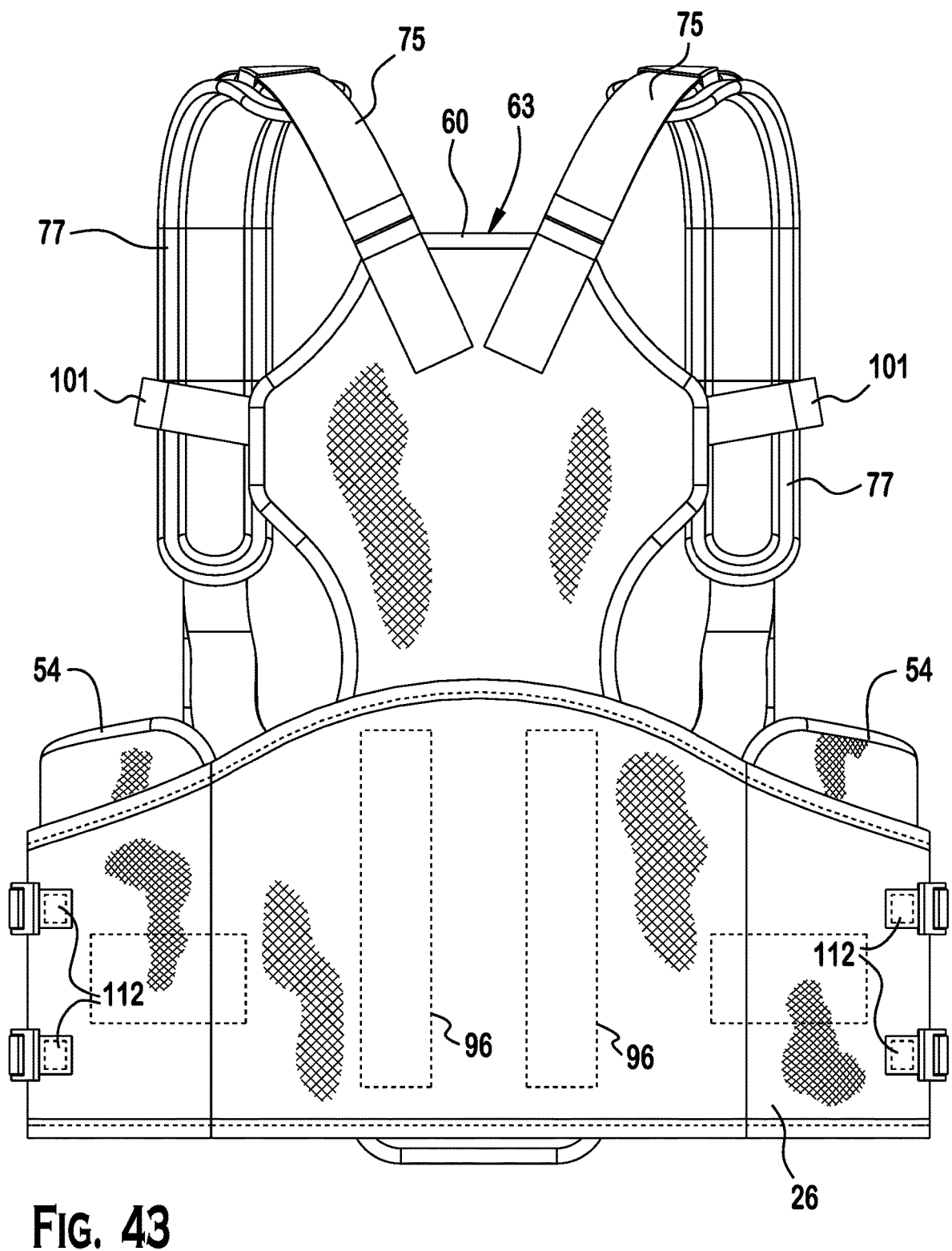
FIG. 43 is a rear elevational view of the body brace kit according to FIG. 42 further illustrating how the over the shoulder straps contact the outside of the upper end of the shell and how the side support protrude above the upper end of the brace body.
Figure 44:
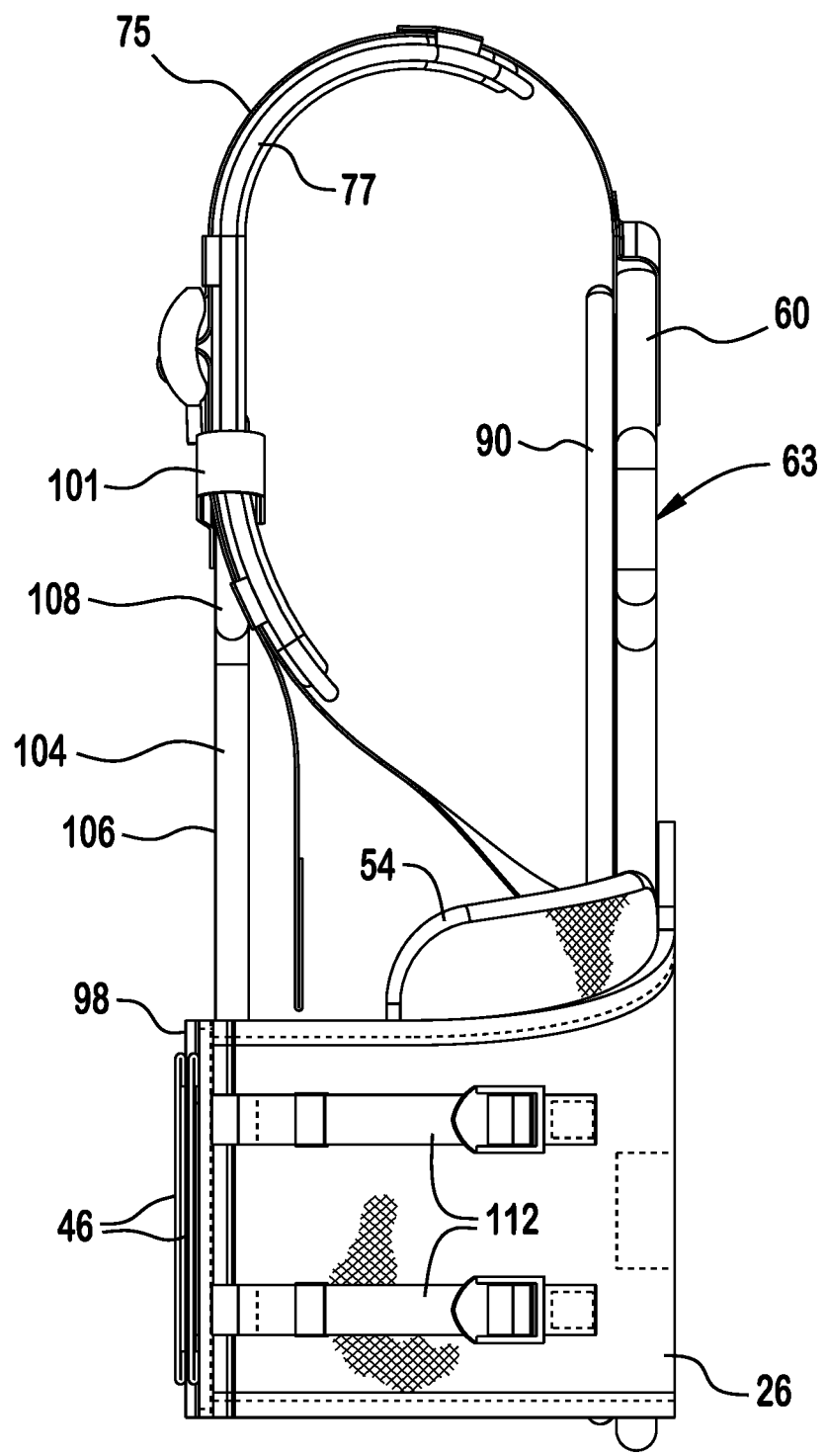
FIG. 44 is a right-side elevational view of the body brace kit according to FIG. 42 illustrating optional side buckles and protruding portion of the side support members. The side buckles are preferred but not necessary.
Figure 45:
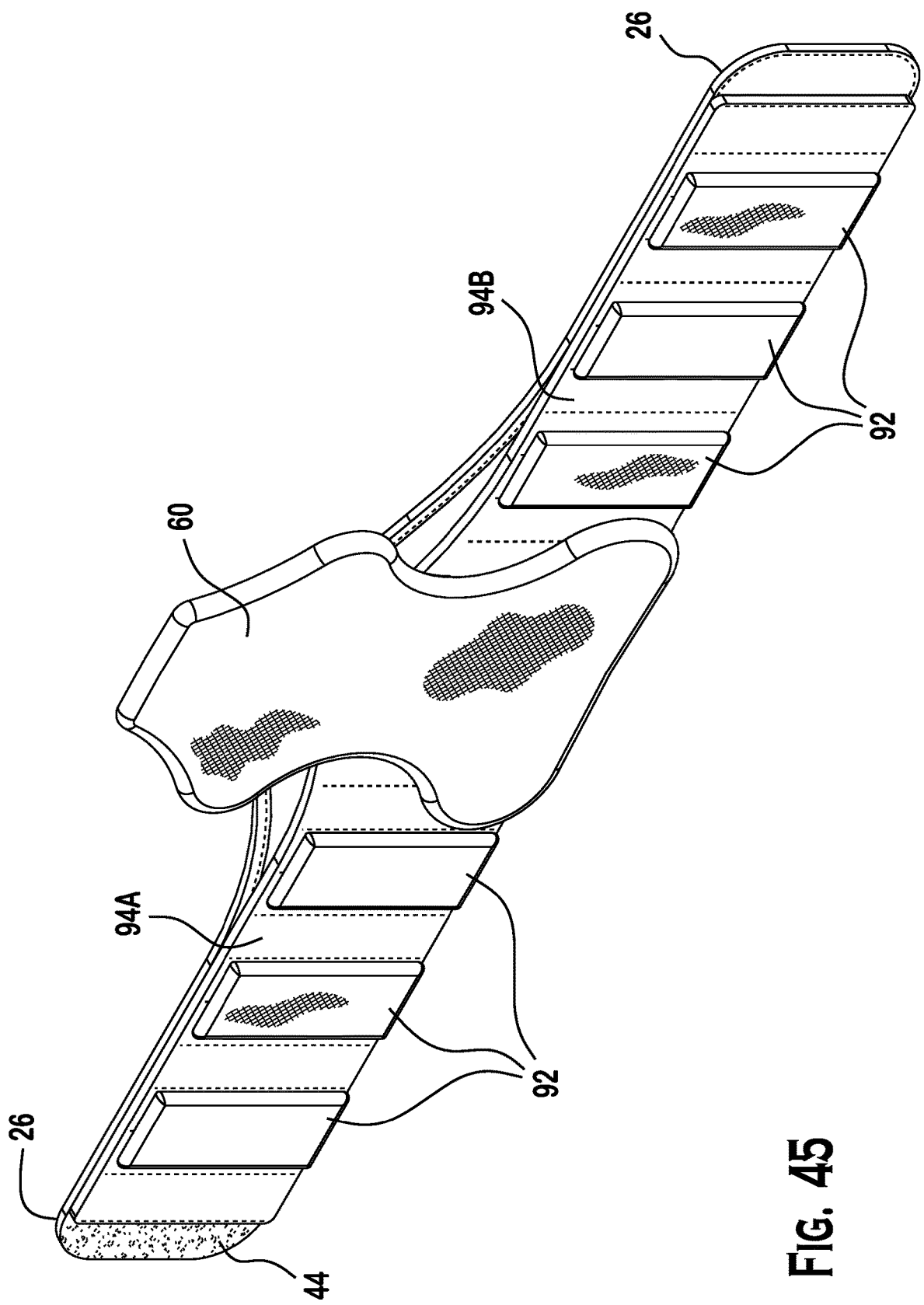
FIG. 45 is a front, top, right, perspective view of a body brace kit according to a fourth preferred embodiment of the body brace kit. This embodiment comprises a first brace body on the outside that has first and second torso wings attached on the inside face. Attached to the first and second torso wings are non-protruding side support members. This embodiment shows clearly the hook and loop material on the outer portion of the ends of the brace body for a connection means.
Figure 46:
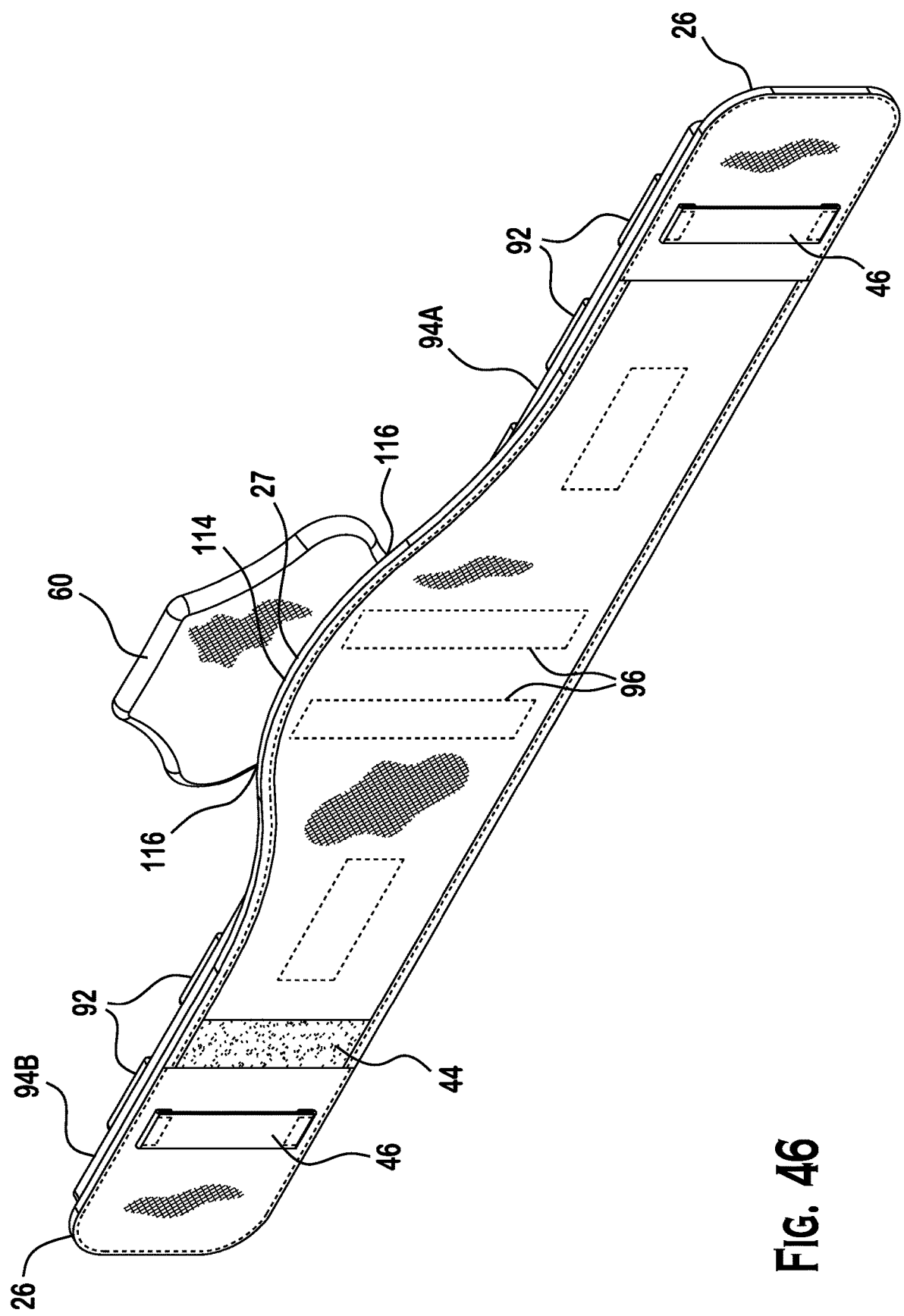
FIG. 46 is a rear, top, left perspective view of the body brace kit in FIG. 45 illustrating the shell is on the interior of the brace body and that they have an intersection point. This figure also illustrates that there are hand loops on the exterior surface of the brace body. The hand loops are preferred but not necessary.
Figure 49:
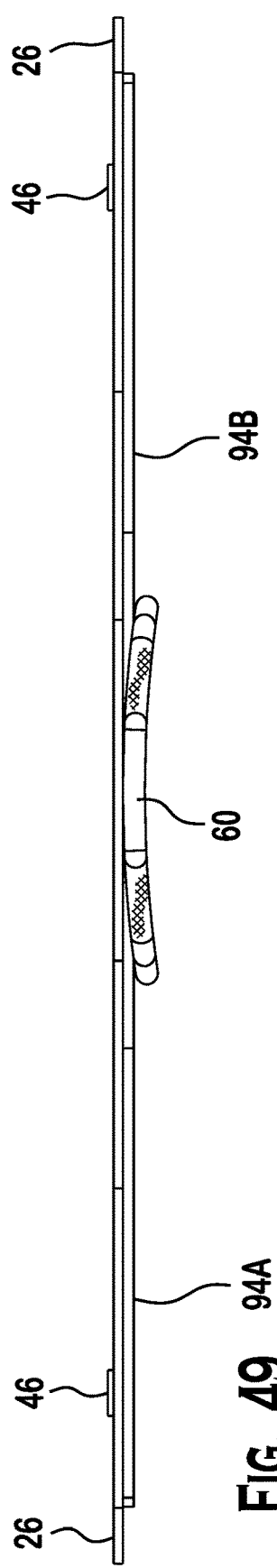
FIG. 49 is a top plan view of the body brace kit according to a fifth preferred embodiment. This kit includes a brace body, first and second torso wings and a shell.
Figure 50:
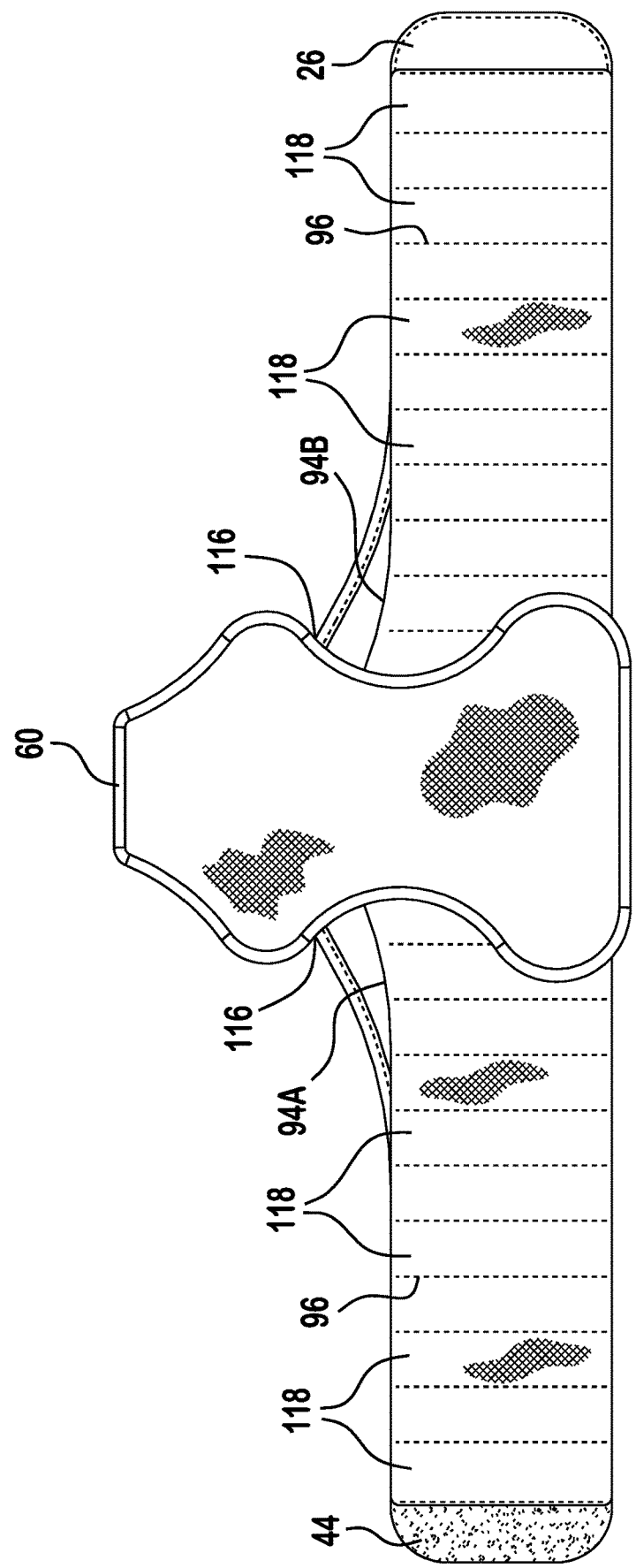
FIG. 50 is a front elevational view of the body brace kit of FIG. 49 illustrating the plurality of encased struts that make up the torso wings.
Figure 51:
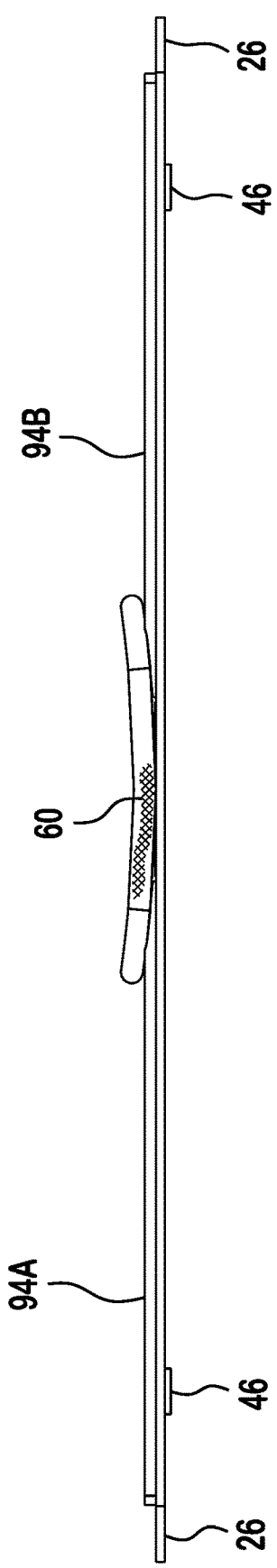
FIG. 51 is a bottom plan view of the body brace kit of FIG. 49 illustrating the varying widths of the elements. The brace body is the widest and will have the greatest circumference. The first and second torso wings are the same length and extend slightly less than the brace body. The shell is centrally located on the back and significantly less wide than the other elements.
Figure 52:
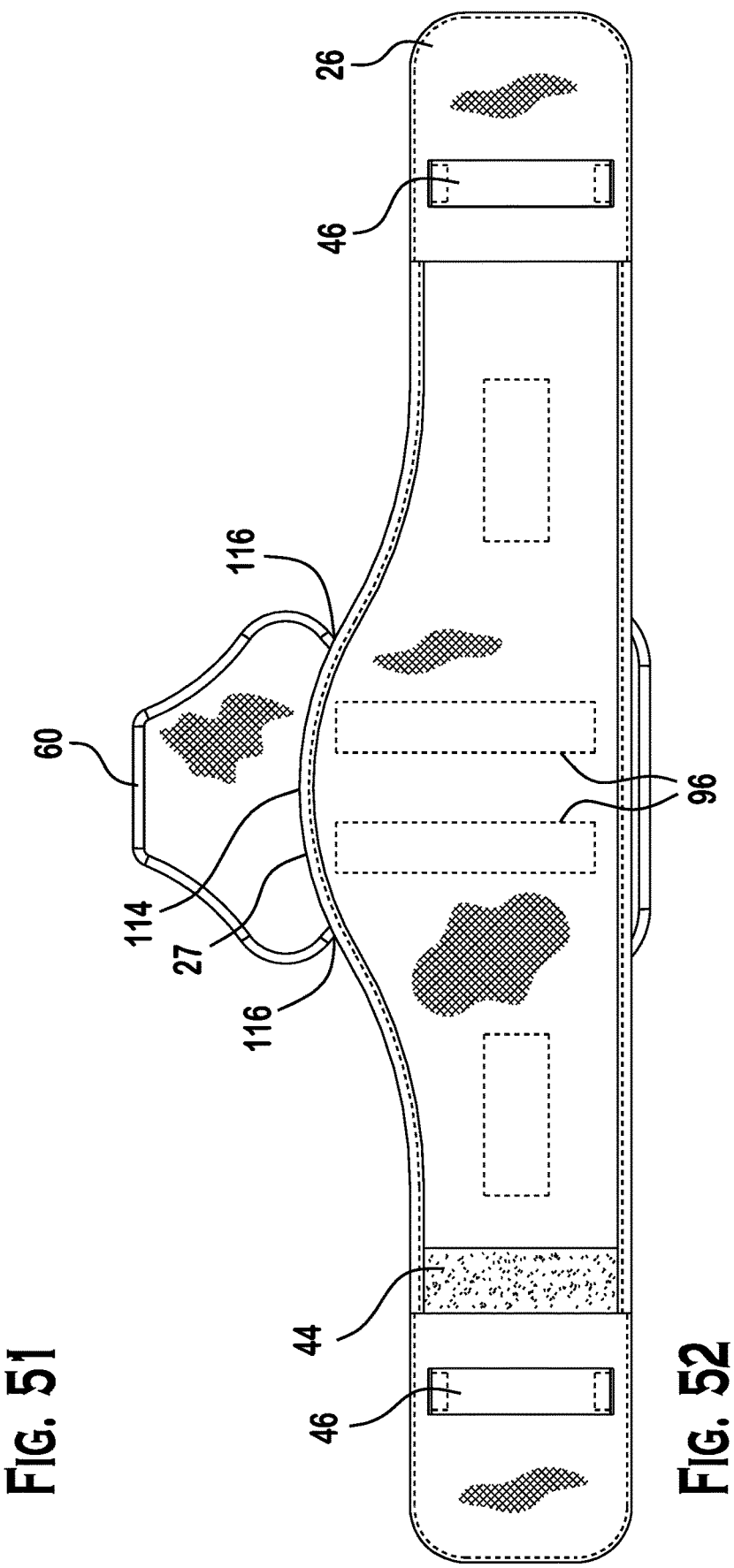
FIG. 52 is a rear elevational view of the body brace kit of FIG. 49 illustrating that the brace body has hand loops near either end for adjustments and tightening.

Referring to FIGS. 42-44, the first brace body 26 may additionally have one or more detachable side buckles 112 on either or both sides Similar to the hand loop 46, the side buckles 112 allow for tightening of the brace body 26. Instead of pulling the ends of the brace body 26 tighter, once the brace body 26 is fastened the side buckles 112 allow for side straps to be pulled to tighten the configuration and create more resistance to movement.

Figure 56:
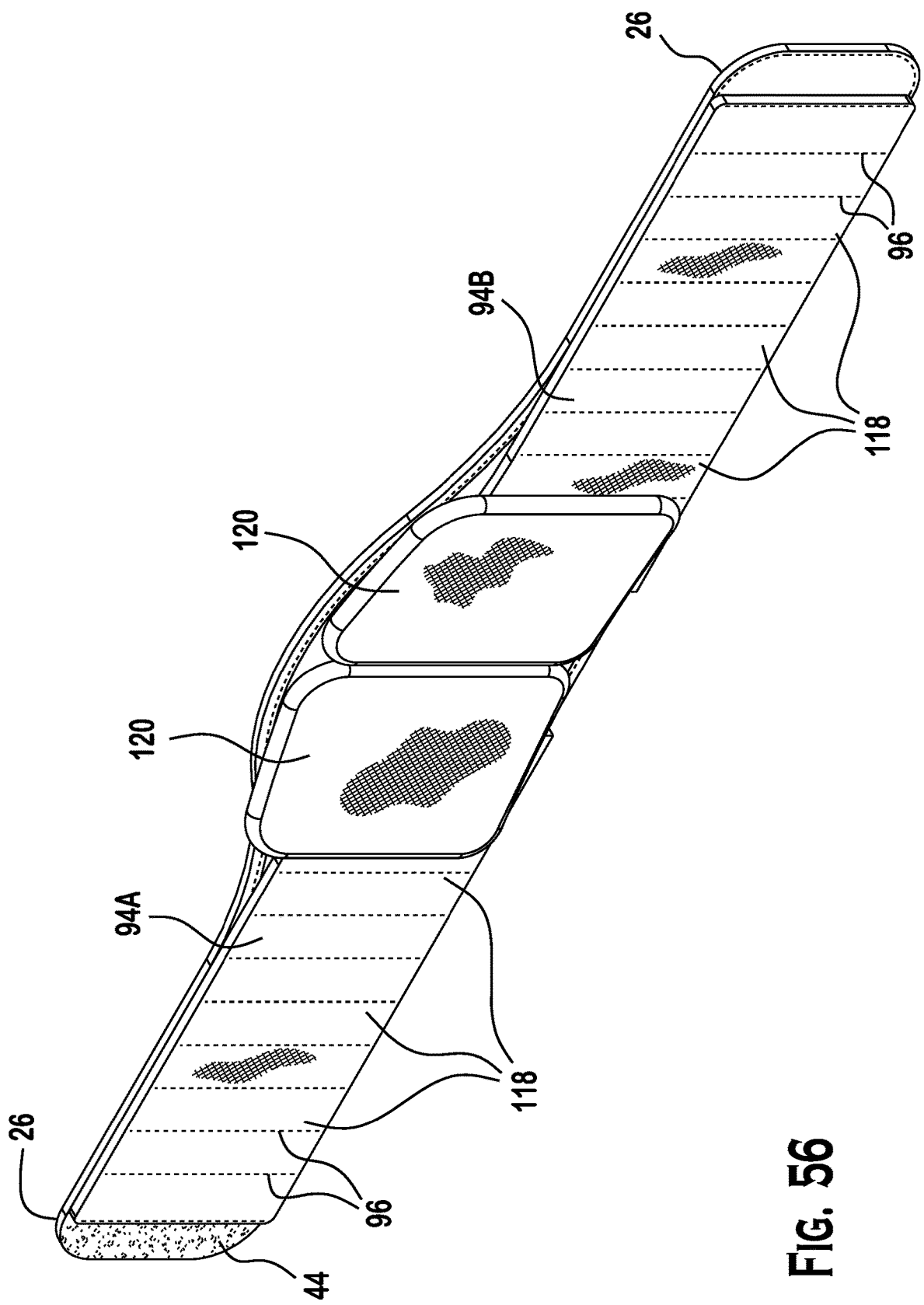
FIG. 56 is a front, top, right, perspective view of a body brace kit according to an seventh preferred embodiment. The kit is comprised an outer brace body, first and second torso wings, and two lower back support pads. It is preferred, but not necessary that the ends of the brace body have hook and loop material for connecting. Those of ordinary skill in the art will appreciate from this disclosure that the ends can be connected by any other suitable means without departing from the scope of the present invention.
Figure 57:
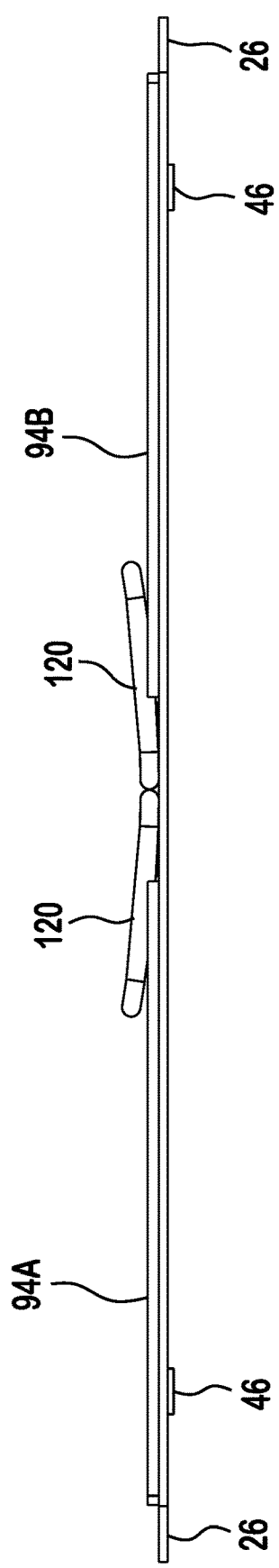
FIG. 57 is a bottom plan view of the body brace kit according to FIG. 56.
Figure 58:
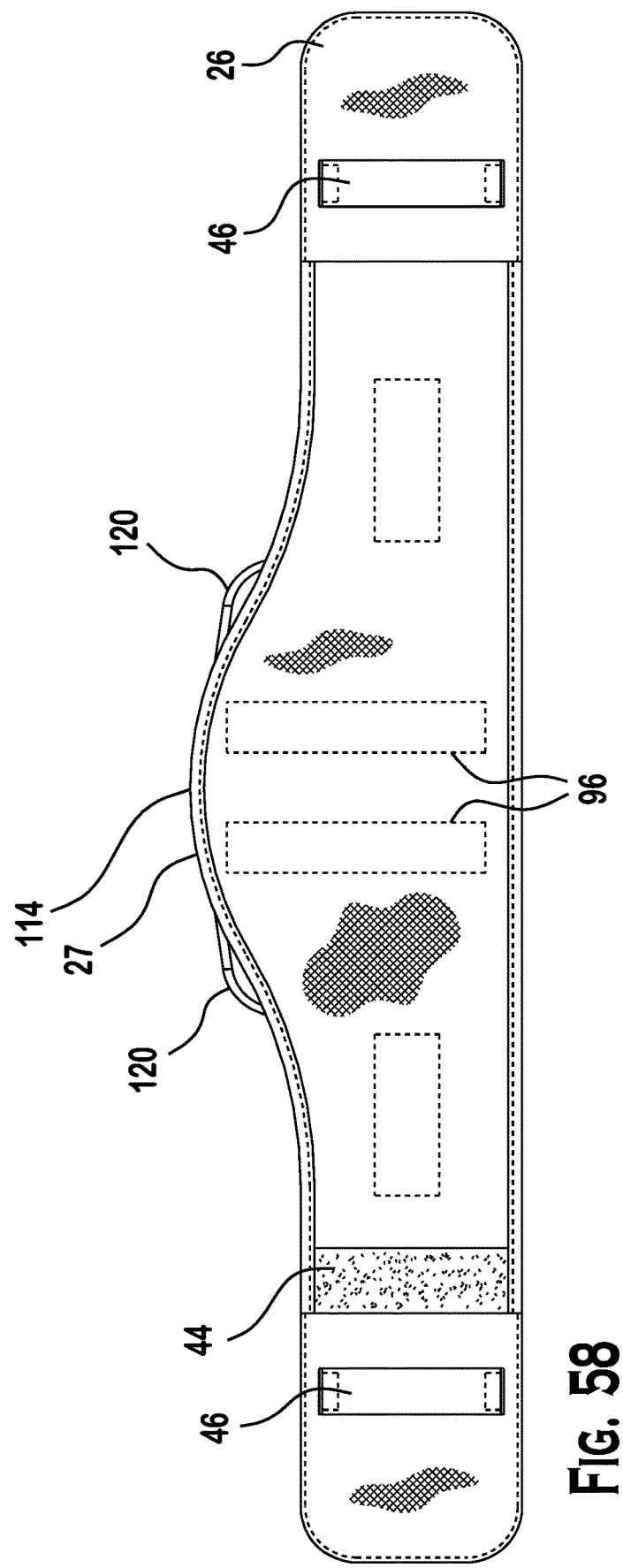
FIG. 58 is a rear elevational view of the body brace kit according to FIG. 56. This Figure illustrates hand loops near both ends of the brace body. The hand loops are preferred, but not necessary.

The possible additional kit 124 components to the brace body 26, of the at least three components will now be explained in greater detail. Referring to FIGS. 56-58 the body brace kit 124 contains a first torso support wing 94a and a second torso support wing 94b. Both the first torso support wing and the second torso support wing 94b may have identical features so they will be described as the torso support wing 94. In embodiments that contain a torso wing 94, the torso wing 94 is detachably connectable to the first brace body such that the torso wing 94 is located between the first brace body 26 and the person when the first brace body 26 is wrapped around the person. More specifically, the torso wing 94 has an exterior face that is adjacent to and in contact with the interior face of the brace body 26. The torso wing 94 provides additional support to the torso of the person to facilitate maintaining the torso in a contoured configuration. Each torso wing 94 preferably comprises a plurality of encased struts 118 aligned generally side-to-side and each preferably having a longitudinal side facing the longitudinal side of an adjacent one of the plurality of encased struts. The encased struts 118 are configured on the torso wing 94 to provide resistance to any lateral bending of the person. The torso wing is preferably formed by a plurality of struts which are configured to allow the torso wing to be flexibly wrapped around the circumference of a person, but providing resistance to bending in any other direction. In a sense, once the wing is wrapped about a person, it becomes a customized wall/cast which does not allow bending of the torso thereafter. It is preferred, but not necessary that the first and second torso support wing fully encircle a person's body so that the entire torso is prevented from bending and so the person is maintained in the desired configuration without otherwise unable to bend along any length of the body/back/torso which is overlapped by the encased struts. The torso wings can be detachably removed and replaced on a person without departing from the scope of the present invention. Alternatively, the torso wing plurality of struts may be configured to allow the covered back/person/torso to bend slightly while providing a biasing/elastic return force which gently encourages the person back into the desired configuration. The wall/cast provided by the support wings may be configured such that part of the wall/cast is formed by the shell and/or the chest support member without departing from the scope of the present invention.

Referring to FIGS. 56-58 the body brace kit 124 includes a lower back support pad 96. In embodiments containing a lower back support pad 96, when the first brace body 26 is wrapped around the person's torso, the lower back support pads 96 may be located adjacent to and along the back of the torso. The lower back support pad 96 may be placed where needed to provide support and cushion to the person. The lower back support pads 96 may be cut smaller depending on the amount of area the individual needs supported on their back.

Referring to FIGS. 42-44 the body brace kit 124 includes a side support member 54, when the first brace body 26 is wrapped around the person's torso, the side support members 54 are located adjacent to and along the side of the torso, near the hips. The side support members 54 are preferably greater in length than a portion of the first brace body 26 so that when in use the side support member preferably protrudes past at least one of a lower edge and an upper edge 27 of the first brace body 26. The side support members 54 may be placed where needed to provide support and cushion to the person. This may include one on either or both sides of the torso.

Referring to FIGS. 45-48 in this preferred embodiment, the body brace kit 124 may include a plurality of non-protruding side support members 92 (depending on the needs of this person there could be any appropriate number). The body brace kit 124 may include one or more non-protruding side support members 92. In embodiments containing a non-protruding side support member 92, they could be the same position as a side support member 54 but are preferably not greater in length than any portion of the first brace body. In FIGS. 45-48 the non-protruding side support members 92 are attached to the interior face of the first and second torso wing 94*a,b*. The non-protruding side support members do not protrude from either the upper 27 or lower edge of the brace body 26. The non-protruding side support members 92 may be placed where needed to provide support and cushion to the person. This may include one on either or both sides of the torso.

While the body brace 20 and the body brace kit 124 are preferably discussed herein as being formed by components which may be detachable from each other, those of ordinary skill in the art will appreciate from this disclosure that the body brace 20 and body brace kit 124 may be formed by components that are affixed to each other and not detachable without departing from the scope of the present invention.

Referring to FIGS. 35-55, the body brace kit 124 may include a shell 60 configured to maintain the person's torso in a contoured configuration and to provide resistance against bending the torso in a manner that does not conform with the contoured configuration. The shell may comprise a polymer core encased in padding.

When attached, the shell 60 may be positioned on the first brace body and configured to contact a greater portion of a back of the person than the first brace body 26. The shell is preferably shaped so that the lateral width of the shell increases, then decreases, then increases again as one moves from the arcuate upper edge to the arcuate lower edge such that each lateral side has a sideways W-shape. The shell may be further configured to have a lateral width of that increases, then decreases, then increases again as one moves from the arcuate upper edge to the arcuate lower edge such that support is provided at the person's shoulder blades and hips while allowing relative twisting motion therebetween.

Figure 53:
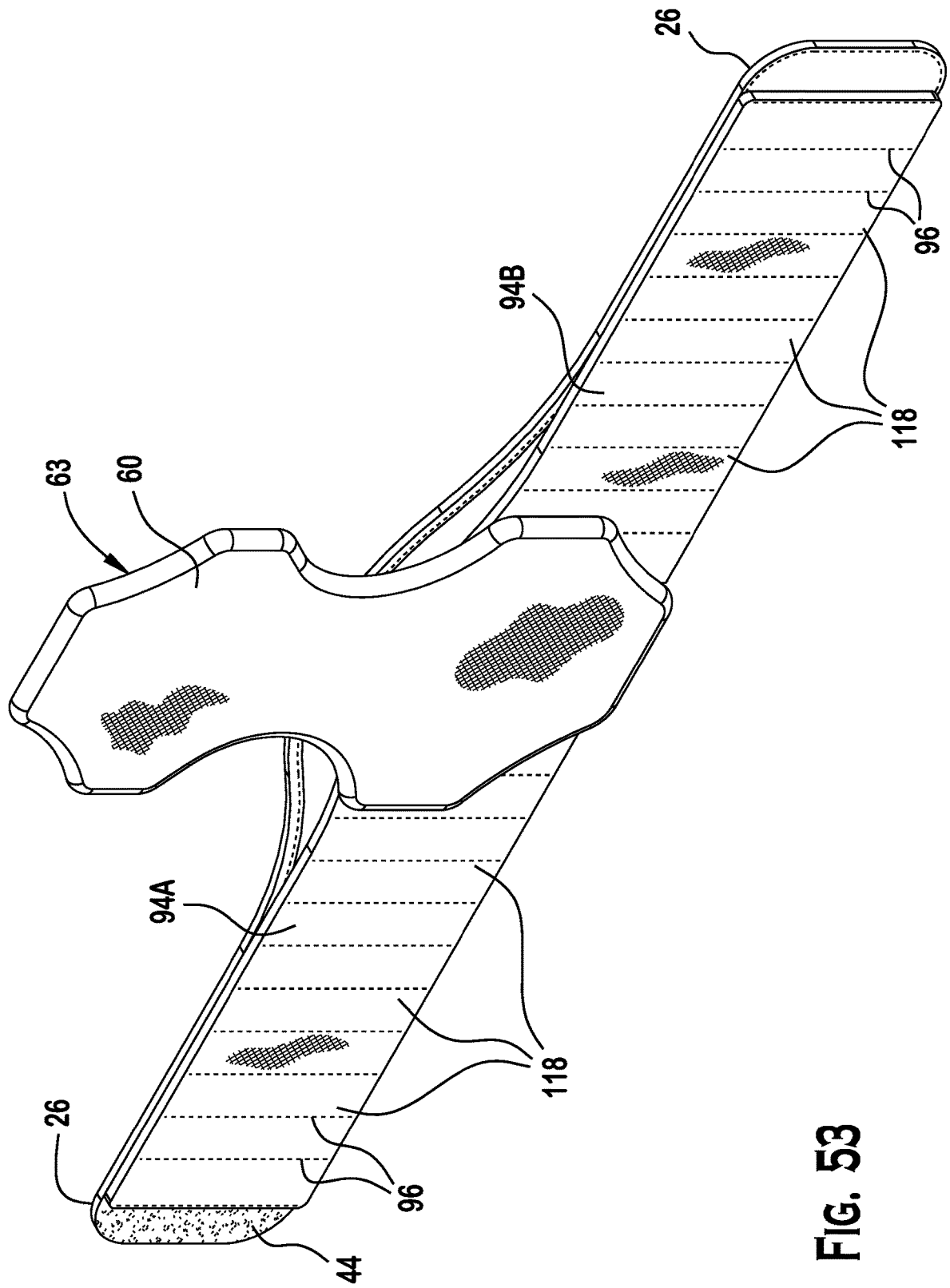
FIG. 53 is a front, top, right, perspective view of a body brace kit according to a sixth preferred embodiment. Specifically, this consists of a brace body, first and second torso wings and an enlarged shell to cover a greater area of the back than in previous embodiments.
Figure 54:
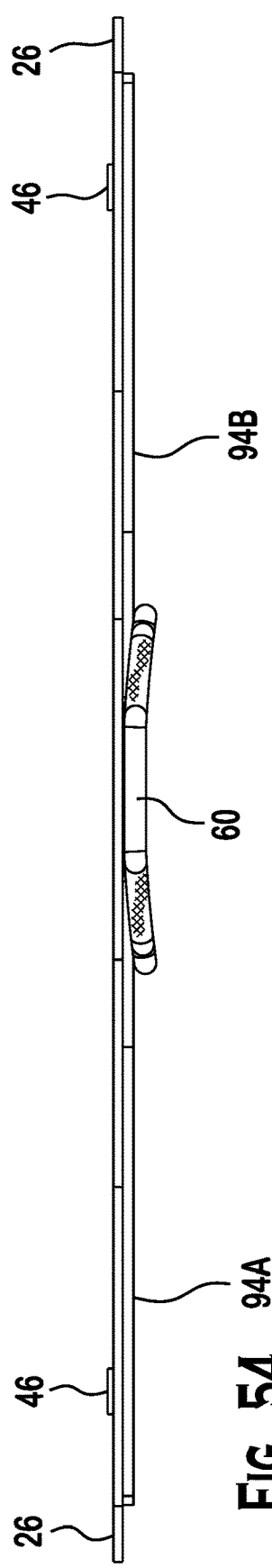
FIG. 54 is a top plan view of the body brace kit according to FIG. 53 illustrating the varying widths of the elements. The brace body is the widest and will have the greatest circumference. The first and second torso wings are the same length and extend slightly less than the brace body. The shell is centrally located on the back and significantly less wide than the other elements. The kit may include shells of multiple sizes to allow a person or physician to alter the shell based on the area of trauma or the size of the person.
Figure 55:
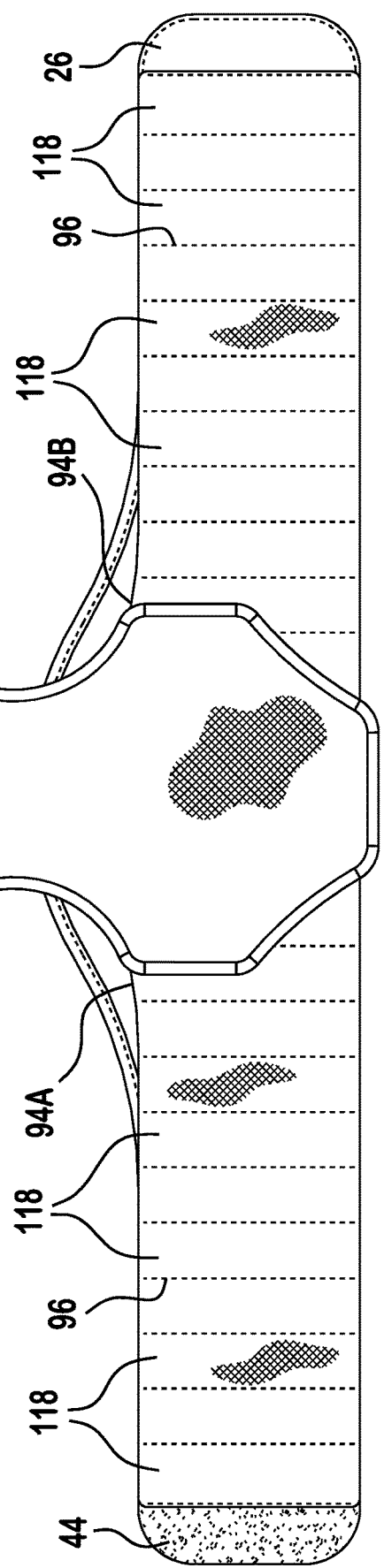
FIG. 55 a front elevational view of the body brace kit according to FIG. 53 illustrating the increased size of the shell. This also illustrates the encased struts of the torso wings and illustrates that the brace body extends beyond the torso wings.

The shell may come in a number of different sizes. A kit 124 may be ordered with a medium sized shell 61 or a large sized shell 63. FIGS. 53 and 55 illustrate the large shell 63 size. Heating and cooling may be implemented to manipulate the configuration of the shell 60. Additionally, the shell 60 may be trimmed to be best configured to the individual's support needs.

Referring to FIGS. 35, 37, 38 and 56-59 the body brace kit 124 may include a back-support member 90 detachably positioned on a side of the shell 60 which faces the person's back as shown in FIG. 35. In FIG. 35 the back-support members 90 are attached to the shell on both side of the central in-use vertical axis 122 and they extend in a direction parallel to that axis. Alternatively, when no shell is present detachably positioned on either the first and second torso wings 94*a,b* (when present) as shown in FIG. 56 or the brace body 26 as shown in FIG. 59. The length of the back-support members 90 can be customizable by the user or they can be the entire length of the shell.

Figure 40:
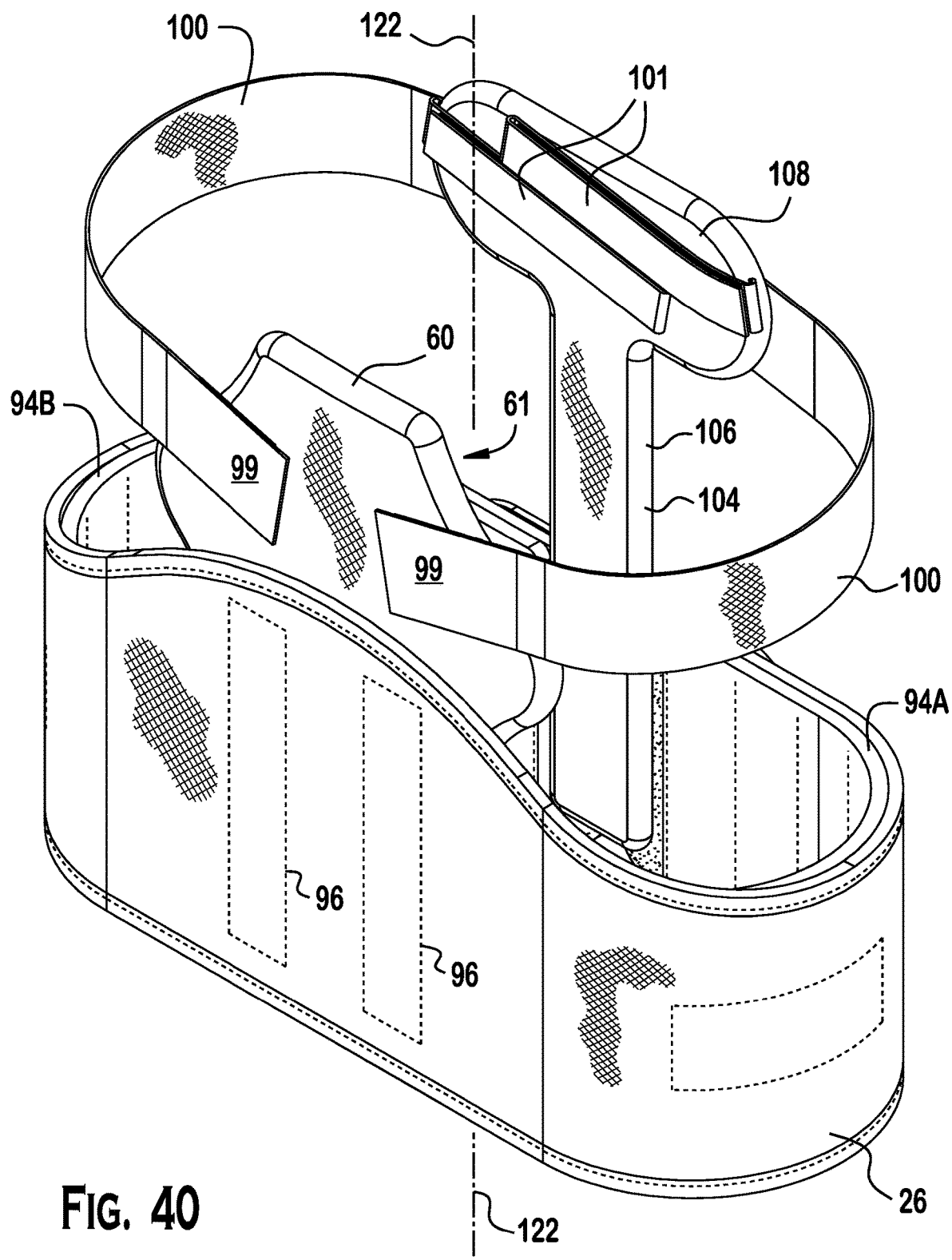
FIG. 40 is a rear, top, left perspective view of a new preferred embodiment of the body brace kit. The kit in FIG. 40 consist of a brace body with hand loops, a chest support and a shell. The chest support is attached to the shell via an underarm strap that has front end attached to the chest support and back ends attached to the shell. There is also first and second torso wings attached to the brace body on the inside face of the brace body.
Figure 41:
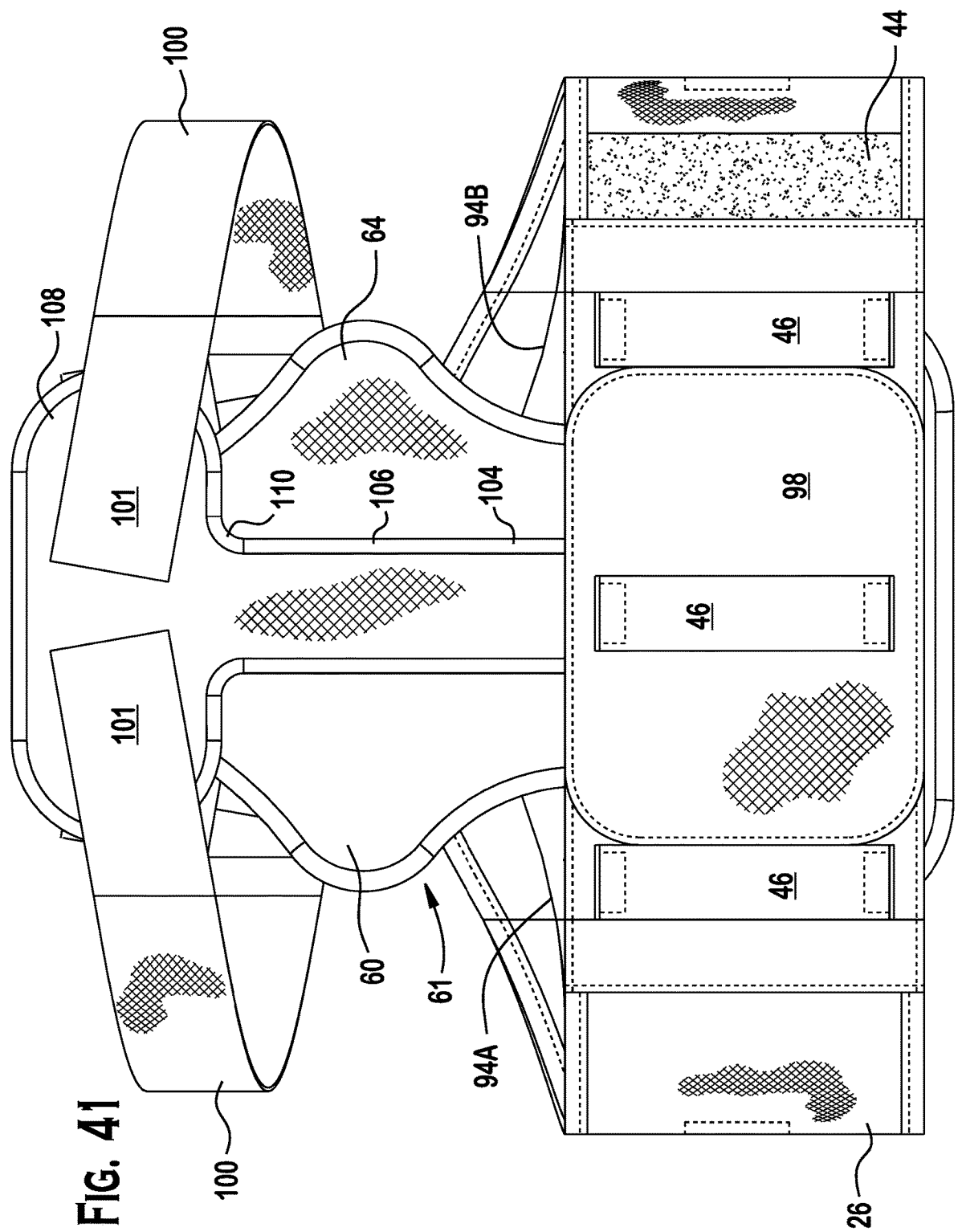
FIG. 41 is a front elevational view of the body brace kit of FIG. 40. This figure more clearly illustrates the chest support. The chest support may have two elements, a stem, and a crossbar. The area where the stem and crossbar connect is preferably a curved interface.

Referring to FIG. 40 the body brace kit 124 may include a chest support member 104 attachable to the first brace body 26 and preferably configured to contact a greater portion of the chest of the person than the first brace body 26. The chest support member 104 may be configured to maintain the chest in a second contoured configuration and to provide resistance against bending in a manner that does not conform with the second contoured configuration. The contoured configuration of the torso/back may be the same as the second contoured configuration of the chest without departing from the scope of the present invention.

The chest support member 104 may be comprised of a stem 106 and crossbar 108. The stem 106 attaches to the inner face of the brace body 26 so that the chest support member is located between the torso and the brace body 26. The stem 106 is configured in a long rectangular shape to extend upwards, the length of the torso. The stem and crossbar are attached at a curved interface 110 at the top of the stem 106 and the lower side of the crossbar 108. The crossbar 108 is the upper portion of the chest support member 104 and extends width wise across the chest. In some embodiments extending around the crossbar 10, as seen in FIG. 40, there are adjustable underarm straps 100. Those of ordinary skill in the art will appreciate from this disclosure that the chest support member 104 may have any shape without departing from the scope of the present invention.

Referring to FIGS. 35, 36, and 38-42 the underarm straps 100 have front ends 101 and back ends 99. The back end may be fastened via hook and loop material 40 to the shell 60 or attached by any other suitable method. The underarm strap front ends 101 may be fastened via hook and loop material to the crossbar 108 of the chest support member 104 or attached by any other suitable means. Alternatively, in kits that do not require a chest support member 104 the underarm straps front ends are attachable to the brace body 26 or to the over abdomen connecting member 98 as in FIG. 35.

Any of the components of the body brace kit 124, except for the first body brace, may be both detachably attachable to the first brace body, and shape adjustable via heating and cooling too. These changes may allow for each body brace kit 124 to provide a contoured configuration(s) customized for the person.

In one preferred embodiment the body brace kit 124 consists of two lower back support pads 96 in addition to the brace body 26. In an embodiment that builds on the previous preferred embodiment, FIG. 56 illustrates a body brace kit 124 that consists of a brace body 26 on the outside when wrapped around the torso adjacent and attached to first and second torso wings 94ab adjacent to and attached on the inner face to the outer face of the lower back support pads 96, which contact the back side of the torso. This illustrates that embodiments of the kit may consist of more than three elements.

In another preferred embodiment the body brace kit is comprised of the brace body 26, the shell 60, and at least one side support member 54. An example of this preferred embodiment is shown in FIG. 43 where there are two side supports 54. There are additionally shown shoulder 75 and underarm straps 100, as well as side buckles 112.

An additional preferred embodiment of the kit 124 includes the first brace body 26, the shell 60, and the chest support member 104. This combination is shown in FIG. 40 wherein the chest support member 104 and shell 60 are held together by underarm straps 100 to provide greater stability.

It is recognized by those skilled in the art that changes may be made to the above described methods without departing from the broad inventive concept thereof. It is understood, therefore, that this invention is not limited to the particular embodiments disclosed, but is intended to cover all modifications which are within the spirit and scope of the invention as defined by the above specification, the appended claims and/or shown in the attached drawings.

What is claimed is:

1. A body brace kit that is customizable for use in supporting at least a portion of a torso of a person, comprising:
   wherein the body brace kit comprises at least three components, one of the at least three components being a first brace body configured to wrap around the at least a portion of the torso of the person to provide support to the torso and generally define a central in-use axis;
   wherein the at least three components further comprise at least two components from the following list of detachable members:
   (1) a first torso support wing comprising:
      a first plurality of encased struts aligned generally side-to-side and each having a longitudinal side facing the longitudinal side of an adjacent one of the first plurality of encased struts, the first torso support wing being configured to encircle at least a part of the torso of a person to provide resistance against lateral bending of the person;
   (2) a second torso support wing comprising:
      a second plurality of encased struts aligned generally side-to-side and each having a longitudinal side facing the longitudinal side of an adjacent one of the second plurality of encased struts, the second torso support wing being configured to encircle at least a second part of the torso of the person to provide resistance against lateral bending of the person;
   (3) a lower back support pad, configured to be located along a back of the person when used with the first brace body wrapped around the person;
   (4) a side support member configured to be located along a side of the torso when used with the first brace body wrapped around the person, the side support member being greater in length than a portion of the first brace body so that when in use the side support member protrudes past at least one of a lower edge and an upper edge of the first brace body;
   (5) a non-protruding side support member, configured to be located along a side of the torso when used with the first brace body wrapped around the person, the non-protruding side support member not being greater in length than a portion of the first brace body so that when in use the non-protruding side support member does not protrude past either one of the lower edge and the upper edge of the first brace body;
   (6) a shell positionable on the first brace body and configured to contact a greater portion of the back of the person than the first brace body, the shell being configured to maintain the back in a contoured configuration and to provide resistance against bending in a manner that does not conform with the contoured configuration;
   (7) a back support member, configured to be detachably positioned on a side of the shell which faces the person's back; and
   (8) a chest support member positionable on the first brace body and configured to contact a greater portion of a chest of the person than the first brace body, the chest support being configured to support the chest of the person and to provide resistance against bending; and
   wherein all of the at least three components, except for the first body brace, are: (1) detachably attachable to the first brace body; and (2) can be adjusted via heating and cooling thereof to allow a shape to be changed to provide the contoured configuration customized for the person,
   wherein all of the at least three components, except for the first brace body, can after being configured in the contoured configuration can be reconfigured via reheating and cooling thereof to allow the shape to be changed to provide a new contoured configuration,
   wherein the at least three components comprise: the first brace body, the first torso support wing, and the second torso support wing, wherein the at least three components further comprise the shell, and
wherein the at least three components further comprise the chest support member.

2. The body brace kit of claim 1, wherein the at least three components further comprise the non-protruding side support member.

3. The body brace kit of claim 1, wherein the at least three components further comprise the side support member.

4. A body brace kit that is customizable for use in supporting at least a portion of a torso of a person, comprising:
wherein the body brace kit comprises at least three components, one of the at least three components being a first brace body configured to wrap around the at least a portion of the torso of the person to provide support to the torso and generally define a central in-use axis;
wherein the at least three components further comprise at least two components from the following list of detachable members:
(1) a first torso support wing comprising:
a first plurality of encased struts aligned generally side-to-side and each having a longitudinal side facing the longitudinal side of an adjacent one of the first plurality of encased struts, the first torso support wing being configured to encircle at least a part of the torso of a person to provide resistance against lateral bending of the person;
(2) a second torso support wing comprising:
a second plurality of encased struts aligned generally side-to-side and each having a longitudinal side facing the longitudinal side of an adjacent one of the second plurality of encased struts, the second torso support wing being configured to encircle at least a second part of the torso of the person to provide resistance against lateral bending of the person;
(3) a lower back support pad, configured to be located along a back of the person when used with the first brace body wrapped around the person;
(4) a side support member configured to be located along a side of the torso when used with the first brace body wrapped around the person, the side support member being greater in length than a portion of the first brace body so that when in use the side support member protrudes past at least one of a lower edge and an upper edge of the first brace body;
(5) a non-protruding side support member, configured to be located along a side of the torso when used with the first brace body wrapped around the person, the non-protruding side support member not being greater in length than a portion of the first brace body so that when in use the non-protruding side support member does not protrude past either one of the lower edge and the upper edge of the first brace body;
(6) a shell positionable on the first brace body and configured to contact a greater portion of the back of the person than the first brace body, the shell being configured to maintain the back in a contoured configuration and to provide resistance against bending in a manner that does not conform with the contoured configuration;
(7) a back support member, configured to be detachably positioned on a side of the shell which faces the person's back; and
(8) a chest support member positionable on the first brace body and configured to contact a greater portion of a chest of the person than the first brace body, the chest support being configured to support the chest of the person and to provide resistance against bending; and
wherein all of the at least three components, except for the first body brace, are: (1) detachably attachable to the first brace body; and (2) can be adjusted via heating and cooling thereof to allow a shape to be changed to provide the contoured configuration customized for the person,
wherein all of the at least three components, except for the first brace body, can after being configured in the contoured configuration can be reconfigured via reheating and cooling thereof to allow the shape to be changed to provide a new contoured configuration,
wherein the at least three components comprise: the first brace body, the shell, and the chest support member, and
wherein the at least three components further comprise the non-protruding side support member.

5. A body brace kit that is customizable for use in supporting at least a portion of a torso of a person, comprising:
wherein the body brace kit comprises at least three components, one of the at least three components being a first brace body configured to wrap around the at least a portion of the torso of the person to provide support to the torso and generally define a central in-use axis;
wherein the at least three components further comprise at least two components from the following list of detachable members:
(1) a first torso support wing comprising:
a first plurality of encased struts aligned generally side-to-side and each having a longitudinal side facing the longitudinal side of an adjacent one of the first plurality of encased struts, the first torso support wing being configured to encircle at least a part of the torso of a person to provide resistance against lateral bending of the person;
(2) a second torso support wing comprising:
a second plurality of encased struts aligned generally side-to-side and each having a longitudinal side facing the longitudinal side of an adjacent one of the second plurality of encased struts, the second torso support wing being configured to encircle at least a second part of the torso of the person to provide resistance against lateral bending of the person;
(3) a lower back support pad, configured to be located along a back of the person when used with the first brace body wrapped around the person;
(4) a side support member configured to be located along a side of the torso when used with the first brace body wrapped around the person, the side support member being greater in length than a portion of the first brace body so that when in use the side support member protrudes past at least one of a lower edge and an upper edge of the first brace body;
(5) a non-protruding side support member, configured to be located along a side of the torso when used with the first brace body wrapped around the person, the non-protruding side support member not being greater in length than a portion of the first brace body so that when in use the non-protruding side support member does not protrude past either one of the lower edge and the upper edge of the first brace body;
(6) a shell positionable on the first brace body and configured to contact a greater portion of the back of the person than the first brace body, the shell being configured to maintain the back in a contoured configuration and to provide resistance against bending in a manner that does not conform with the contoured configuration;

(7) a back support member, configured to be detachably positioned on a side of the shell which faces the person's back; and (8) a chest support member positionable on the first brace body and configured to contact a greater portion of a chest of the person than the first brace body, the chest support being configured to support the chest of the person and to provide resistance against bending; and wherein all of the at least three components, except for the first body brace, are: (1) detachably attachable to the first brace body; and (2) can be adjusted via heating and cooling thereof to allow a shape to be changed to provide the contoured configuration customized for the person, wherein all of the at least three components, except for the first brace body, can after being configured in the contoured configuration can be reconfigured via reheating and cooling thereof to allow the shape to be changed to provide a new contoured configuration, wherein the at least three components comprise: the first brace body, the shell, and the chest support member, and wherein the body brace kit further comprises a plurality of straps each having a first strap end positionable on the shell and a second strap end which is positionable on either the first brace body and the chest support member.

* * * * *